(12) United States Patent
Barrow et al.

(10) Patent No.: US 7,968,571 B2
(45) Date of Patent: Jun. 28, 2011

(54) 2,4,6-SUBSTITUTED PYRIDYL DERIVATIVE COMPOUNDS USEFUL AS BETA-SECRETASE INHIBITORS FOR THE TREATMENT OF ALZHEIMER'S DISEASE

(75) Inventors: James C. Barrow, Harleysville, PA (US); Georgia B. McGaughey, Harleysville, PA (US); Philippe G. Nantermet, Lansdale, PA (US); Hemaka A. Rajapakse, Wyncote, PA (US); Harold G. Selnick, Ambler, PA (US); Shaun R. Stauffer, Schwenksville, PA (US); Joseph P. Vacca, Telford, PA (US); Shawn J. Stachel, Perkasie, PA (US); Craig A. Coburn, Royersford, PA (US); Matthew G. Stanton, Boston, MA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 1125 days.

(21) Appl. No.: 11/547,994

(22) PCT Filed: Apr. 20, 2005

(86) PCT No.: PCT/US2005/013480
§ 371 (c)(1),
(2), (4) Date: Oct. 10, 2006

(87) PCT Pub. No.: WO2005/103043
PCT Pub. Date: Nov. 3, 2005

(65) Prior Publication Data
US 2008/0015233 A1    Jan. 17, 2008

Related U.S. Application Data

(60) Provisional application No. 60/563,612, filed on Apr. 20, 2004, provisional application No. 60/630,539, filed on Nov. 23, 2004, provisional application No. 60/653,037, filed on Feb. 15, 2005.

(51) Int. Cl.
*A61K 31/443* (2006.01)
*C07D 413/04* (2006.01)

(52) U.S. Cl. ................................. 514/340; 546/269.4

(58) Field of Classification Search ............... 546/269.4; 514/340
See application file for complete search history.

(56) References Cited

U.S. PATENT DOCUMENTS

| 4,518,601 | A | 5/1985 | Kristiansen et al. |
| 7,109,217 | B2 | 9/2006 | Coburn et al. |
| 2006/0058278 | A1 | 3/2006 | Coburn et al. |
| 2006/0149092 | A1 | 7/2006 | Nantermet et al. |
| 2006/0161020 | A1 | 7/2006 | Coburn et al. |
| 2007/0293497 | A1 | 12/2007 | Nantermet et al. |

FOREIGN PATENT DOCUMENTS

| WO | WO 03/057721 | 7/2003 |
| WO | WO 03/106405 | 12/2003 |
| WO | WO 2004/022523 | 3/2004 |
| WO | WO 2004/050619 | 6/2004 |
| WO | WO2004/089911 | 10/2004 |
| WO | WO2004/089911 A | 10/2004 |
| WO | WO 2005/005374 | 1/2005 |
| WO | WO 2005/018545 | 3/2005 |
| WO | WO 2005/032471 | 4/2005 |
| WO | WO 2005/051914 | 6/2005 |
| WO | WO 2005/065195 | 7/2005 |
| WO | WO 2005/103020 | 11/2005 |

OTHER PUBLICATIONS

C. Coburn et al., "Identification of a Small Molecule Nonpeptide Active Site Beta-Secretase Inhibitors . . . ,", J. Med. Chem., vol. 47, pp. 6117-6119 (2004).
S. Stachel et al., "Structure-Based design of Potent and Selective Cell-Permeable Inhibitors of Human Beta-Secretase (BACE-1)," J. Med. Chem., vol. 47, pp. 6447-6450 (2004).
S. Stachel et al., "Conformationally biased P3 amide replacements of B-secretase inhibitors," Biorganic & Medicinal Chemistry Letters, vol. 16, pp. 641-644 (2006).
Supplementary European Search Report for PCT/US2005/042087 dated Aug. 18, 2010; 5 pages.
Nantermet, P.; et. al.; "Evolution of Tertiary Carbinamine BACE-1 Inhibitors Aβ Reduction in Rhesus CSF upon Oral Dosing", ChemMedChem; 2009; 4, pp. 37-40.
Zhu, H.; et. al.; "Rapid P1 SAR of brain penetrant tertiary carbinamine derived BACE inhibitors", Biiorganic and Medicinal Chemistry Letters, 20 2010 1779-1782.
International Search Report for PCT/US05/013480 filed Apr. 20, 2005 mailed on Jul. 20, 2005; 3 pages.
Written Opinion for PCT/US05/013480 filed Apr. 20, 2005 mailed on Jul. 20, 2005; 4 pages.
International Search Report for PCT/US05/042087 filed Nov. 18, 2005 mailed on Jul. 14, 2006; 3 pages.
Written Opinion for PCT/US05/042087 filed Nov. 18, 2005 mailed on Jul. 14, 2006; 4 pages.
Supplementary European Search Report for PCT/US2005/042087 dated Aug. 18, 2010; 5 pages.

*Primary Examiner* — Patricia L Morris
(74) *Attorney, Agent, or Firm* — Keith D. MacMillan; Gerard M. Devlin

(57) ABSTRACT

The present invention is directed to 2,4,6-substituted pyridyl derivative compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

12 Claims, No Drawings

2,4,6-SUBSTITUTED PYRIDYL DERIVATIVE COMPOUNDS USEFUL AS BETA-SECRETASE INHIBITORS FOR THE TREATMENT OF ALZHEIMER'S DISEASE

CROSS-REFERENCE TO RELATED APPLICATIONS

This application claims priority under 35 U.S.C. §119(e) from U.S. provisional applications Ser. Nos. 60/563,612, filed Apr. 20, 2004; 60/630,539, filed Nov. 23, 2004; and 60/653,037, filed Feb. 15, 2005.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to a class of novel 2,4,6-substituted pyridine derivative compounds which are useful as inhibitors of the β-secretase enzyme, and to the treatment of diseases in which the β-secretase enzyme is involved, such as Alzheimer's Disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and SAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to 2,4,6-substituted pyridyl derivative compounds useful as inhibitors of the β-secretase enzyme, and are useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

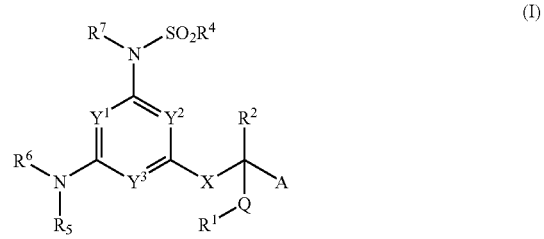

wherein:
X is selected from the group consisting of

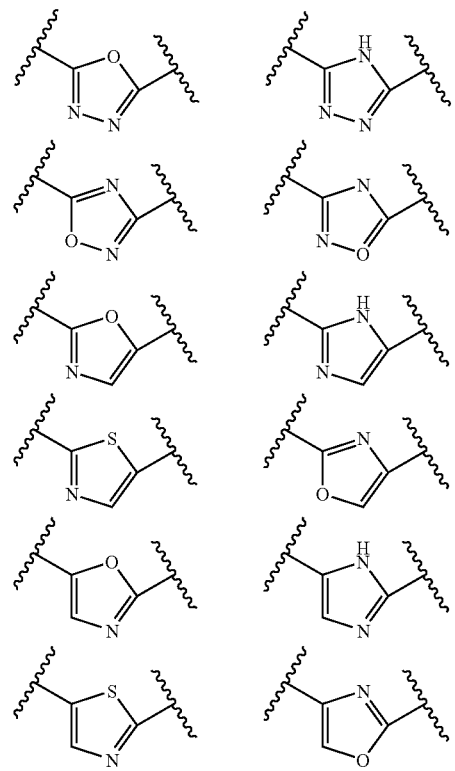

-continued

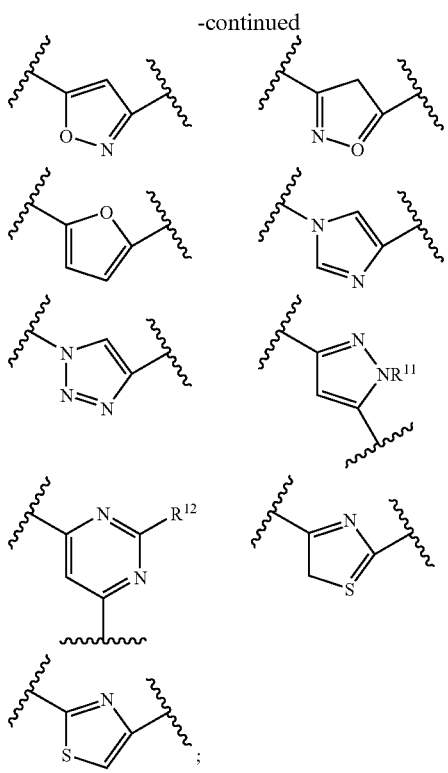

wherein R[11] and R[12] are independently selected from the group consisting of
(a) hydrogen,
(b) —$C_{1-10}$ alkyl,
(c) $C_{2-10}$ alkenyl,
(d) $C_{2-10}$ alkynyl,
(e) —$C_{3-12}$ cycloalkyl, and
(f) aryl selected from the group consisting of phenyl and napthyl;
wherein said alkyl, cycloalkyl, alkenyl, alkynyl or aryl is unsubstituted or substituted with one or more
  (i) halo,
  (ii) —OH,
  (iii) —CN,
  (iv) —$C_{1-10}$ alkyl
  (v) —$C_{3-12}$ cycloalkyl, and
  (vi) —O—$C_{1-10}$ alkyl,
$Y^1$ is N, and $Y^2$ and $Y^3$ are each CH, or, or
$Y^2$ is N, and $Y^1$ and $Y^3$ are each CH, or
$Y^3$ is N, and $Y^1$ and $Y^2$ are each CH;
A is selected from the group consisting of
(1) hydrogen,
(2) —$C_{1-10}$ alkyl, and
(3) —$C_{2-10}$ alkenyl,
wherein said alkyl or alkenyl is unsubstituted or substituted with one or more
  (a) halo,
  (b) —$C_{3-12}$ cycloalkyl,
  (c) —OH,
  (d) —CN,
  (e) —O—$C_{1-10}$ alkyl,
  (f) phenyl, or
  (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
and said phenyl and heteroaryl is unsubstituted or substituted with one or more
  (i) halo,
  (ii) —OH,
  (iii) —CN,
  (iv) —O—$C_{1-10}$ alkyl,
  (v) —$C_{1-10}$ alkyl, or
  (vi) —$C_{3-12}$ cycloalkyl;
Q is —$C_{0-3}$ alkyl, wherein said alkyl is unsubstituted or substituted with one or more
  (1) halo,
  (2) —$C_{3-12}$ cycloalkyl,
  (3) —OH,
  (4) —CN,
  (5) —O—$C_{1-10}$ alkyl, and
  (6) —$C_{1-10}$ alkyl;
$R^1$ is (1) aryl selected from the group consisting of phenyl and napthyl,
  (2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
  (3) —$C_{1-10}$ alkyl, and
  (4) $C_{3-8}$ cycloalkyl, said cycloalkyl optionally fused to a $C_{6-10}$ aryl group,
wherein said alkyl, cycloalkyl, aryl or heteroaryl is unsubstituted or substituted with one or more
  (a) halo,
  (b) —$C_{1-10}$ alkyl, wherein said alkyl is unsubstituted or substituted with halogen,
  (c) —OH,
  (d) —CN,
  (e) —O—$C_{1-10}$ alkyl,
  (f) —$C_{3-12}$ cycloalkyl, and
  (g) —$NR^8R^9$;
$R^2$ is selected from the group consisting of
  (1) —OH, and
  (2) —$NR^8R^9$, wherein $R^8$ and $R^9$ are selected from the group consisting of
    (a) hydrogen,
    (b) $C_{1-10}$ alkyl, and
    (c) $C_{0-6}$ alkyl-$C_{6-10}$ aryl,
or when $R^2$ is $NR^8R^9$, and $R^8$ and A are hydrogen, then Q, $R^1$ and $R^9$ may be linked together to form the group —$CH_2CH_2CH_2$—,
or when $R^2$ is $NR^8R^9$, then Q, $R^1$ and A may be linked together to form a 4 or 5 carbon alkyl chain, wherein one or more of the carbon atoms in the alkyl chain may be replaced with an N, O or S atom, or an $SO_2$ group;
$R^4$ is selected from the group consisting of
  (1) —$C_{1-10}$ alkyl, or
  (2) —$C_{3-12}$ cycloalkyl,
wherein said alkyl and cycloalkyl is unsubstituted or substituted with one or more
  (a) halo,
  (b) —OH,
  (c) —CN,
  (d) —O—$C_{1-10}$ alkyl,
  (e) —$C_{1-10}$ alkyl,
  (f) —$C_{3-12}$ cycloalkyl, (g) aryl selected from the group consisting of phenyl and napthyl, or
(h) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
and said aryl and heteroaryl is unsubstituted or substituted with one or more
(i) halo,
(ii) —OH,
(iii) —CN,
(iv) —O—$C_{1-10}$ alkyl,
(v) —$C_{3-12}$ cycloalkyl, or
(vi) —$C_{1-10}$ alkyl;

$R^7$ is selected from the group consisting of
(1) hydrogen,
(2) —$C_{1-10}$ alkyl, and
(3) aryl selected from the group consisting of phenyl and naphthyl;
wherein said alkyl and aryl is unsubstituted or substituted with one or more
(a) halo,
(b) —OH,
(c) —CN,
(d) —O—$C_{1-10}$ alkyl,
(e) —$C_{3-12}$ cycloalkyl,
(f) aryl selected from the group consisting of phenyl and napthyl, or
(g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl;
wherein said cycloalkyl, aryl or heteroaryl is unsubstituted or substituted with one or more
(i) halo,
(ii) —OH,
(iii) —CN,
(iv) —O—$C_{1-10}$ alkyl,
(v) —$C_{3-12}$ cycloalkyl, or
(vi) aryl selected from the group consisting of phenyl and napthyl;
or $R^4$ and $R^7$ may be linked to form a —$CH_2CH_2CH_2$— group;
$R^5$ and $R^6$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkyl-$C_{3-12}$ cycloalkyl;
wherein said alkyl, cycloalkyl, alkenyl or alkynyl is unsubstituted or substituted with one or more
(a) halo,
(b) —OH,
(c) —CN,
(d) —$C_{1-10}$alkyl
(e) —$C_{3-12}$ cycloalkyl,
(f) —O—$C_{1-10}$ alkyl,
(g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl,
wherein said heteroaryl may be unsubstituted or substituted with halogen;
(h) phenyl, or
(i) —$NR^8R^9$;
or $R^5$ and $R^6$ are joined together with the nitrogen atom to which they are attached to form a 4-6 membered ring, which is unsubstituted or substituted with one or more
(a) —$C_{1-10}$ alkyl,
(b) —$C_{3-12}$ cycloalkyl,
(c) —$(CH_2)_n$-phenyl,
(d) —$C_{2-10}$ alkenyl, or
(e) —$C_{2-10}$ alkynyl,
wherein said alkyl, alkenyl and alkynyl is unsubstituted or substituted with one or more
(i) halo,
(ii) —OH,
(iii) —CN,
(iv) —O—$C_{1-10}$ alkyl, or
(v) —$C_{3-12}$ cycloalkyl;
and said cycloalkyl and phenyl is unsubstituted or substituted with one or more
(i) halo,
(ii) —$C_{1-10}$ alkyl,
(iii) —OH,
(iv) —CN,
(v) —$C_{3-12}$ cycloalkyl, or
(vi) —O—$C_{1-10}$ alkyl;
n is 0, 1, 2, 3 or 4;
and pharmaceutically acceptable salts thereof, and individual enantiomers and diastereomers thereof.

In a preferred embodiment, $Y^1$ is N and $Y^2$ and $Y^3$ are each CH.

In one embodiment, the invention is directed to compounds of formula (I) wherein $R^1$ is phenyl, unsubstituted or substituted, and Q is preferably $CH_2$. Preferably, $R^1$ is unsubstituted phenyl.

In other embodiments, $R^1$ is heteroaryl. Preferred $R^1$ heteroaryl groups include pyridyl (2-pyridyl, 3-pyridyl or 4-pyridyl), thienyl (preferably 2-thienyl or 3-thienyl), thiazole and indynyl.

In other embodiments, $R^1$ is $C_{1-12}$ alkyl or a $C_{3-8}$ cycloalkyl group. Preferred $C_{1-12}$ alkyl $R^1$ groups include $C_{1-6}$ alkyl (preferably unsubstituted $C_{1-6}$ alkyl, including methyl and isopropyl.) Preferred $C_{3-8}$ cycloalkyl groups include cyclopropyl, cyclopentyl and cyclohexyl, preferably unsubstituted. Two of the ring carbon atoms from the cycloalkyl group may be linked to form a $C_{6-12}$ aryl. An exemplary fused group of this embodiment is:

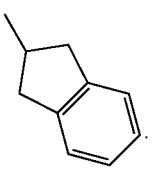

In another embodiment, the invention is directed to compounds of formula (I) wherein $R^2$ is $NR^8R^9$, and preferably both $R^8$ and $R^9$ are hydrogen.

In another embodiment of compounds of formula (I), when $R^2$ is $NR^8R^9$ and $R^8$ and A are each hydrogen, then Q, $R^1$ and $R^9$ may be linked together to form the group —CH$_2$CH$_2$CH$_2$—, thereby forming a pyrrolidinyl group.

In another embodiment of compounds of formula (I), when $R^2$ is $NR^8R^9$, then Q, $R^1$ and A are linked together to form a 4 or 5 carbon alkyl chain, wherein one or more of the carbon atoms in the alkyl chain may be replaced with an N, O or S atom, or an SO$_2$ group.

In another embodiment of compounds of formula (I), $R^2$ is OH.

In another embodiment of the compounds of formula (I), A is C$_{1-10}$ alkyl, unsubstituted or substituted (preferably unsubstituted), preferably C$_{1-6}$ alkyl, unsubstituted or substituted (preferably unsubstituted), and even more preferably methyl.

In alternative embodiments, A may be hydrogen.

In another embodiment of the compounds of formula (I), $R^5$ and $R^6$ are joined together with the nitrogen atom to which they are both linked to form a pyrrolidine ring.

In another embodiment of the compounds of formula (I), $R^4$ and $R^7$ are C$_{1-10}$ alkyl, preferably C$_{1-6}$ alkyl. More preferably, $R^4$ is methyl or isopropyl and $R^7$ is methyl.

In one embodiment of the compounds of formula (I), X is an oxadiazole selected from the group consisting of

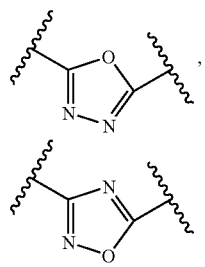 , 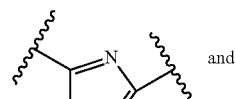 and

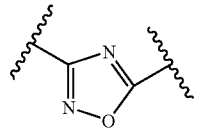

In another embodiment of the compounds of formula (I), X is an oxazole selected from the group consisting of

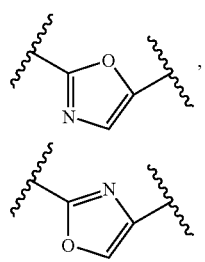

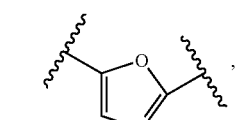

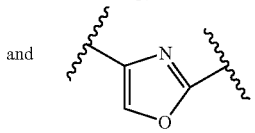

In another embodiment of the compounds of formula (I), X is a thiazole selected from the group consisting of

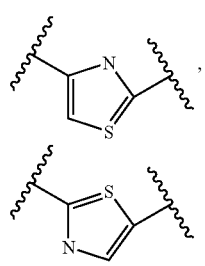

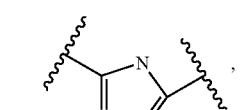

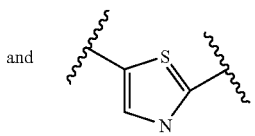

In still additional embodiments of the compounds of formula (I), X is 1,2,4-triazine

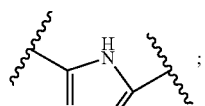

furan

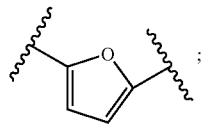

pyrazole

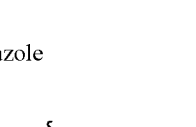

; or pyrimidine

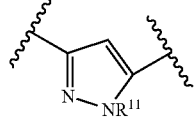

In another embodiment, the invention is directed to compounds of formula (II)

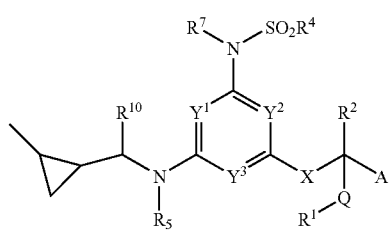

(II)

wherein A, X, $Y^1$, $Y^2$, $Y^3$, Q, $R^1$, $R^2$, $R^4$, $R^5$ and $R^7$ are as defined above, and $R^{10}$ is hydrogen or C$_{1-6}$ alkyl, and pharmaceutically acceptable salts thereof, and individual enantiomers and diastereomers thereof.

In a preferred embodiment of the compounds of formula (II), $Y^1$ is N and $Y^2$ and $Y^3$ are each CH. In one embodiment of the compounds of formula (II), $R^1$ is phenyl and Q is CH$_2$. Preferably, $R^1$ is unsubstituted phenyl.

In another embodiment, the invention is directed to compounds of formula (II) wherein $R^2$ is $NR^8R^9$, and preferably both $R^8$ and $R^9$ are hydrogen.

In another embodiment of compounds of formula (II), $R^2$ is OH.

In another embodiment of the compounds of formula (II), $R^{10}$ is hydrogen. In an alternative embodiment, $R^{10}$ is $C_{1-6}$ alkyl, preferably methyl, ethyl or isopropyl.

In another embodiment of the compounds of formula (II), A is $C_{1-10}$ alkyl, preferably $C_{1-6}$ alkyl, more preferably methyl.

In another embodiment of the compounds of formula (II), $R^4$ and $R^7$ are $C_{1-10}$ alkyl, preferably $C_{1-6}$ alkyl. More preferably, $R^4$ is methyl or isopropyl and $R^7$ is methyl.

In another embodiment of the compounds of formula (II), $R^5$ is hydrogen or, $C_{1-10}$ alkyl, wherein said $C_{1-10}$ alkyl is substituted or unsubstituted with one or more:
(1) halo (preferably fluoro),
(2) —OH,
(3) —CN,
(4) phenyl,
(5) —O$C_{1-10}$ alkyl, or
(6) —NR$^8$R$^9$ (preferably $R^8$ and $R^9$ are each $C_{1-10}$ alkyl).

In compounds of formula (II), preferred $R^5$ groups include hydrogen, methyl, benzyl and —$C_{1-10}$alkyl-NR$^8$R$^9$, wherein $R^8$ and $R^9$ are each $C_{1-10}$ alkyl.

In one embodiment of the compounds of formula (II), X is an oxadiazole selected from the group consisting of

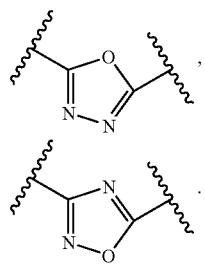 ,  and

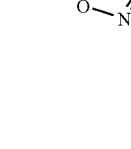 .

In another embodiment of the compounds of formula (II), X is an oxazole selected from the group consisting of

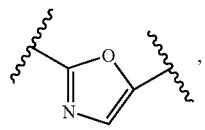 , 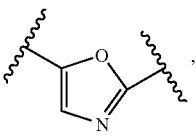 ,

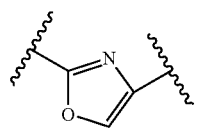 and 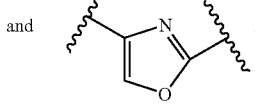 .

In another embodiment of the compounds of formula (II), X is a thiazole selected from the group consisting of

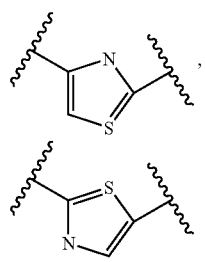 , 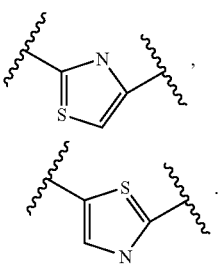 ,

In still additional embodiments of the compounds of formula (II), X is 1,2,4-triazine

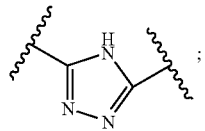 ;

furan

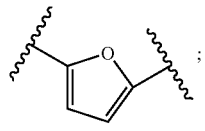 ;

pyrazole

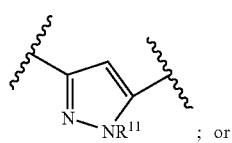 ; or pyrimidine

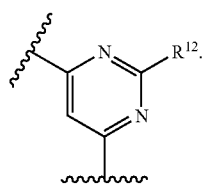 .

When $R^{10}$ is hydrogen, a preferred enantiomeric configuration of compounds of formula (II) are compounds having a trans-S,S configuration at the methyl-cyclopropyl-methyl moiety, as depicted below in formula (IIA):

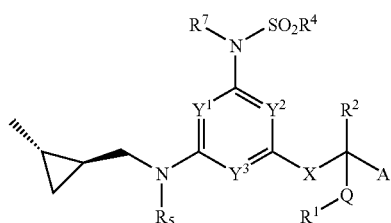

(IIA)

In another embodiment, the invention is directed to compounds of formula (III)

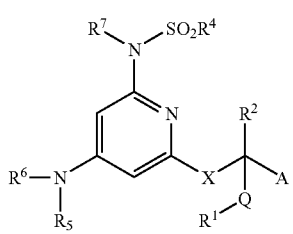

(III)

wherein A, X, Q, $R^1$, $R^2$, $R^4$, $R^5$, $R^6$ and $R^7$ are as defined above, and $R^{10}$ is hydrogen or $C_{1-6}$ alkyl, and pharmaceutically acceptable salts thereof, and individual enantiomers and diastereomers thereof.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated monocyclic, polycyclic or bridged cyclic hydrocarbon radical having the number of carbon atoms designated (e.g., $C_{3-12}$ cycloalkyl means a cycloalkyl group having from three to twelve carbon atoms). Preferred cycloalkyl groups include $C_{3-8}$ cycloalklyl groups, especially $C_{3-8}$ monocyclic cycloalkyl groups. Exemplary monocyclic cycloalkyl groups include cyclopropyl, cyclobutyl, cyclopentyl, cyclohexyl and the like. Exemplary bridged cycloalkyl groups include adamantly and norbornyl.

As used herein, the term "aryl," by itself or as part of another substituent, means an aromatic or cyclic radical having the number of carbon atoms designated (e.g., $C_{6-10}$ aryl means an aryl group having from six to ten carbons atoms). Preferred aryl groups for use in the invention include phenyl and naphthyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). Exemplary heteroaryl groups for use in the invention include furyl, pyranyl, benzofuranyl, isobenzofuranyl, chromenyl, thienyl, benzothiophenyl, pyrrolyl, pyrazolyl, imidazolyl, pyridyl, pyrazinyl, pyrimidinyl, pyridazinyl, indolyl, indazolyl, benzimidazolyl, quinolyl, indynyl and isoquinolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or at a ring heteroatom (i.e., a nitrogen, oxygen or sulfur), which has a valence which permits attachment. Preferably, the attachment is at a ring carbon atom.

Some of the compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

In the compounds of formulas (I) to (III), the carbon atom to which $R^2$, A and Q are bonded is typically a chiral carbon. As a result, the compounds of formulas (I)-(III) may be present as racemates, or in the stereochemically pure (R) or (S) forms. The isomeric forms for compounds of formula (I) are depicted below:

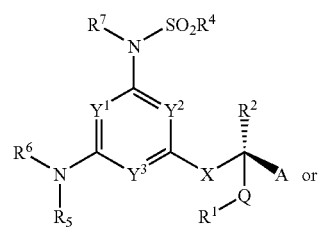

-continued

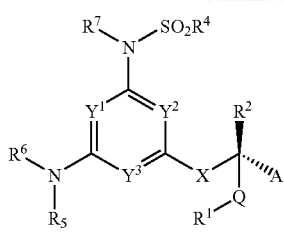

The first configuration depicted above (which is typically the (R) configuration, e.g. when A is $CH_3$, $R^2$ is $NH_2$, Q is $—CH_2—$ and $R^1$ is phenyl) is preferred.

The compounds claimed in this invention can be prepared according to the following general procedure methods (Schemes 1-25), and the specific examples 1-94.

In Scheme 1, an amino acid derivative of type 1 is converted to the corresponding hydrazinyl amide 3 via a two step sequence. To access commercially unavailable amino acid derivatives, a two step alkylation of glycine Schiff base 4 can be used. Schiff base deprotection, Boc protection and ester hydrolysis provides an alternate route to compound 2. The alkylation of 4 for the synthesis of 5 may be performed in an enantioselective manner as described in the literature (see K. Maruoka et al, *J. Am. Chem. Soc.* 2000, 122, 5228-5229 and M. North et al, *Tetrahedron Lett.* 2003, 44, 2045-2048).

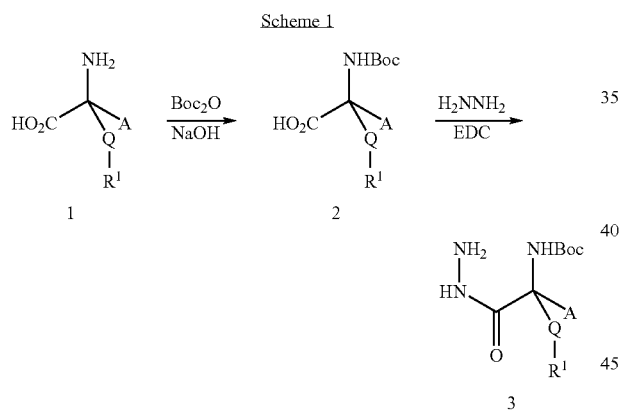

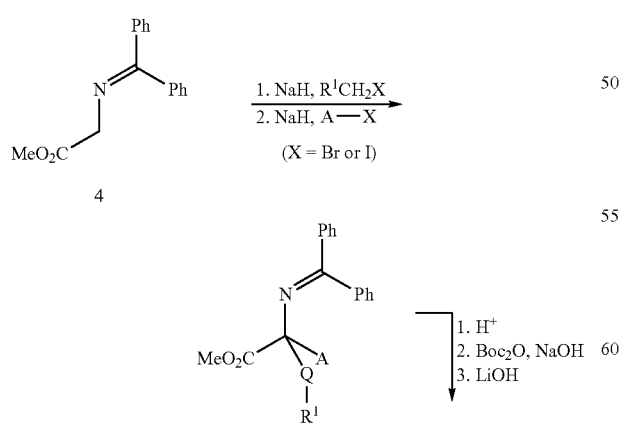

-continued

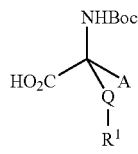

In Scheme 2, N-protected amino acid 2 is converted to carboxamide 6a (or thiocarboxamide 6b), then dehydrated to give nitrile 7. Treatment of 7 with $NH_2OH—HCl$ under mildly basic conditions affords hydroxyamidate 8.

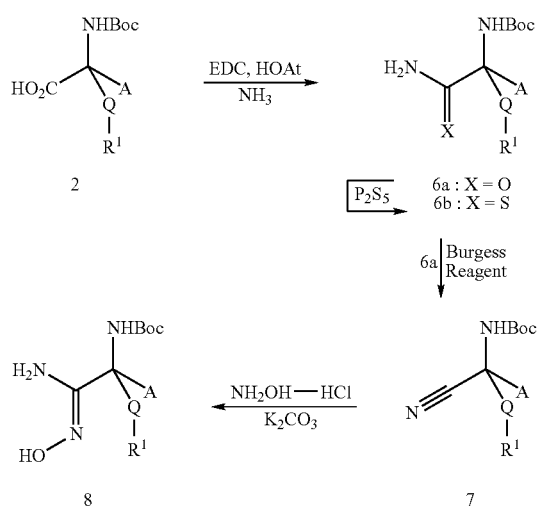

In Scheme 3, reduction of amino acid 1 with in-situ generated $BH_3$ affords the corresponding amino alcohol, which can then be N-protected to afford compound 9. Oxidation of 9 affords aldehyde 10, which can then be transformed to imine 11 under mild conditions.

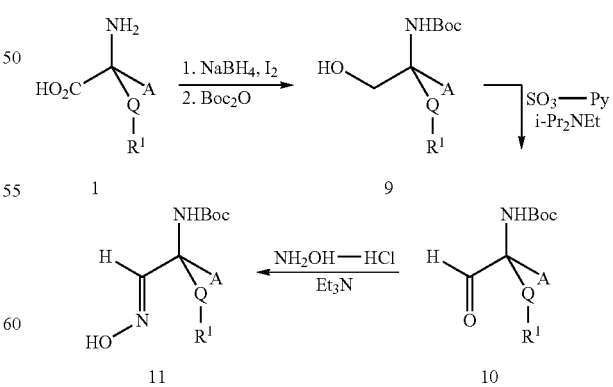

Synthesis of amino alcohol 12 is shown in Scheme 4. Epoxidation of 10, followed by opening with ammonia affords amino alcohol 12.

Scheme 4

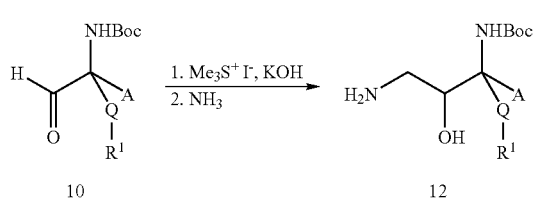

Scheme 5 illustrates the preparation of the regioisomeric aminoalcohol 13: Synthesis of the Ellman derivative of aldehyde 10, addition of vinyl Grignard, ozonolysis and reductive workup, followed by Ellman auxiliary removal.

Scheme 5

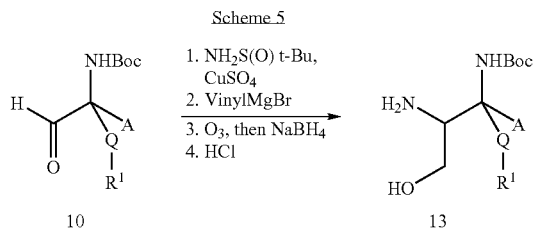

Scheme 6 depicts the preparation of bromoketone 14, via the diazoketone derived from acid 2.

Scheme 6

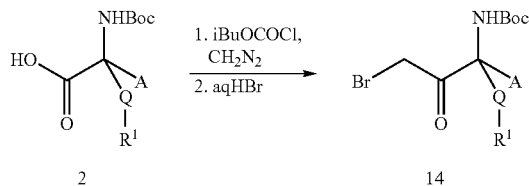

Scheme 7 describes the preparation of intermediates 15-18, to be used in the elaboration of various heterocycles.

Alternatively, one of the chloro groups can be left intact to allow for $R^5R^6N$ introduction late, after the heterocycle X has been constructed (intermediates 15'-18'). Note that, if needed, the second chloro group can also be left intact for replacement with —$(R^7)N$—$SO_2R^4$ after the heterocycle X has been constructed.

Scheme 7

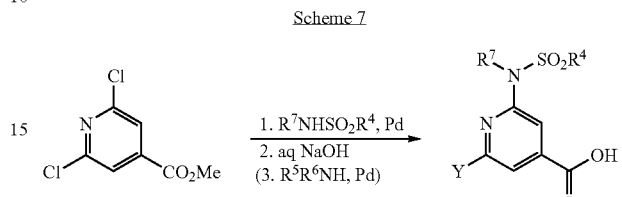

Schemes 8-21 describe the preparation of various heterocycles X. Synthesis of the 1,3,4 oxadiazoles of type 19 could be accomplished by coupling acids 15 with hydrazinyl amide 3, followed by cyclodehydration with Burgess reagent, and Boc deprotection (Scheme 8).

Scheme 8

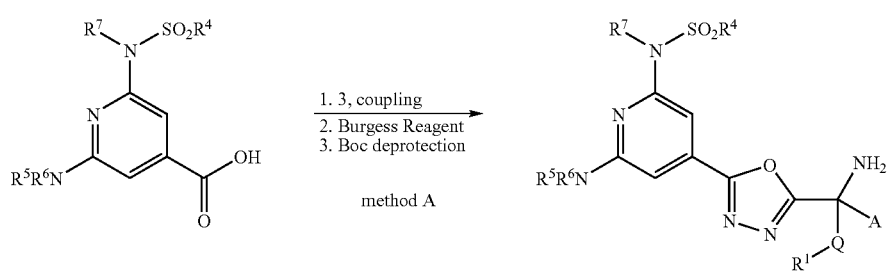

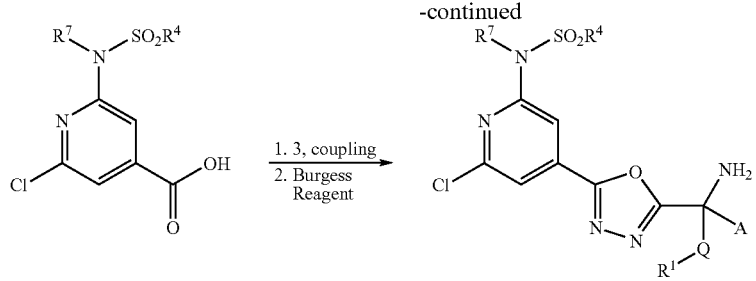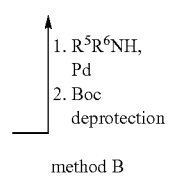

Alternatively, acyl-hydrazides can be directly derived from acids of type 15 to allow the late incorporation of various aminoacid derivatives in the oxadiazole ring. Finally late introduction of the $R^1$ group can be performed from Schiff bases of type 45 (Scheme 8A).

Scheme 8A

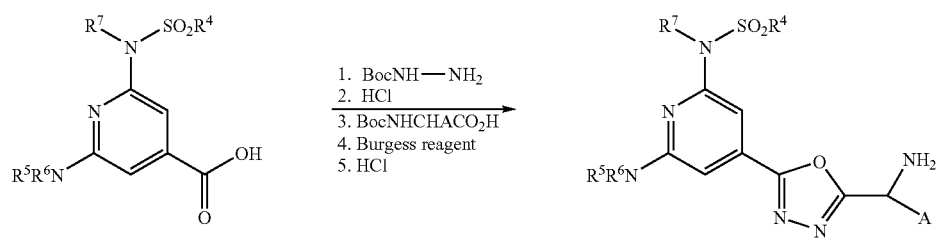

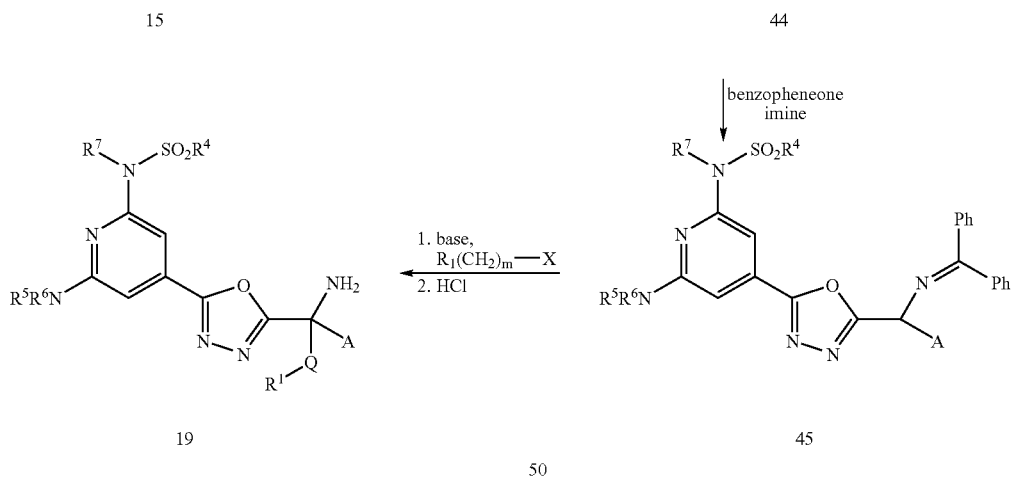

The synthesis of one of the two possible 1,2,4 oxadiazoles is shown in Scheme 9. Coupling acids 15 with hydroxyamidate 11, followed by cyclodehydration under basic conditions and Boc deprotection affords oxadiazole 20.

Scheme 9

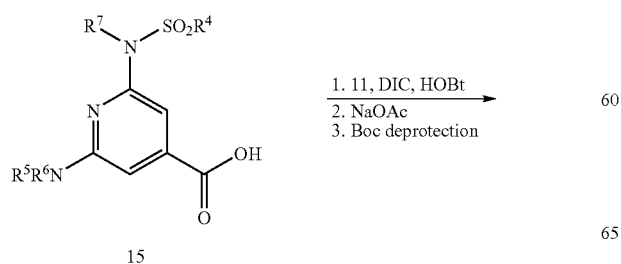

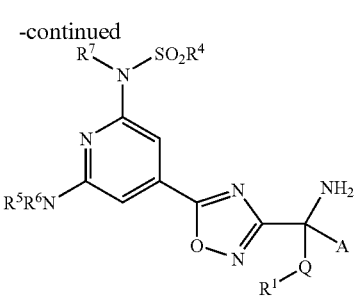

The synthesis of the other possible 1,2,4 oxadiazoles can be achieved from nitrile 17. A sequence similar to that described above affords oxadiazole 21 (Scheme 10).

Scheme 10

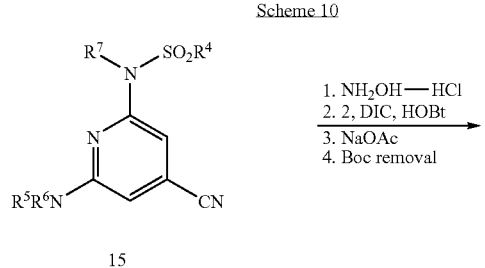

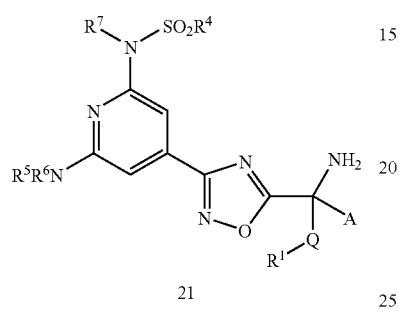

The synthesis of 1,2,4 triazole 22 is described in Scheme 11. Transformation of nitrile 17 to the corresponding imidate under basic conditions, followed by refluxing with hydrazinyl amide 3 and Boc deprotection affords the requisite heterocycle.

Scheme 11

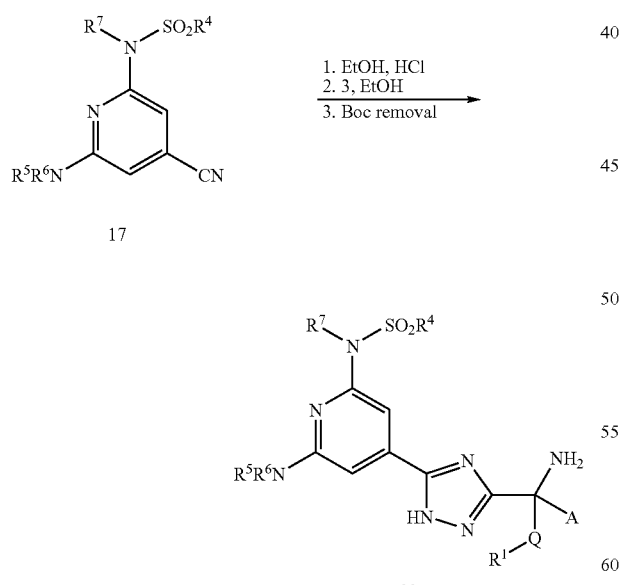

Imidazole 24 is prepared as described in Scheme 12. Coupling of 12 with formic acid and oxidation, followed by ring closure affords imidazole 23. Transformation of bromide 16 to the corresponding boronic acid via lithium halogen exchange, palladium mediated coupling with imidazole 23, and Boc deprotection completes the reaction sequence to compound 24.

Scheme 12

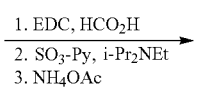

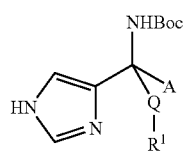

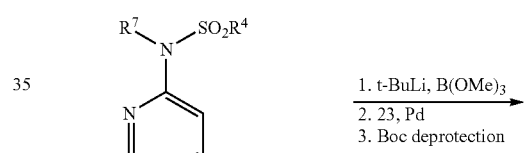

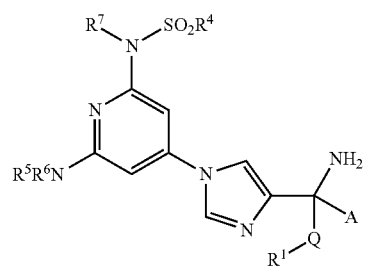

The synthesis of 1,2,3-triazole 26 is described in Scheme 13. Aryl azide formation via a diazonium intermediate obtained from aniline 18, followed by cycloaddition with an appropriate electron deficient alkyne affords 25. Ellman sulfinyl imine formation, nucleophile addition, followed by chiral axiliary cleavage complete the synthesis of 26.

Scheme 13
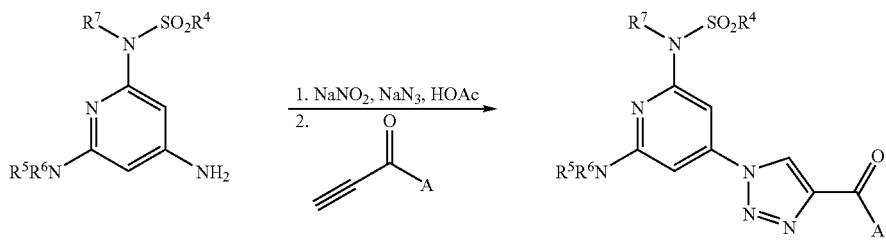
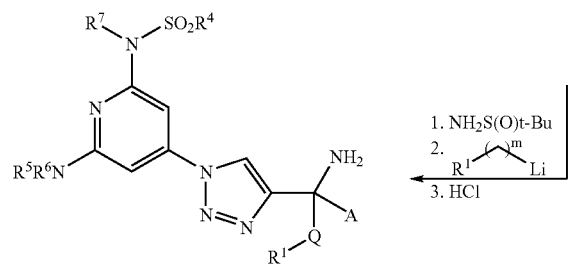
The synthesis of oxazoles 27, thiazoles 28 and imidazoles 29 is shown in Scheme 14. Reduction of acid 15, oxidation to the aldehyde, epoxidation, epoxide opening with ammonia, followed by coupling the resulting amino alcohol with acid 2 and oxidation affords a common intermediate ketoamide. Cyclodehydration under the described conditions gives access to 27, 28 or 29.
Scheme 14
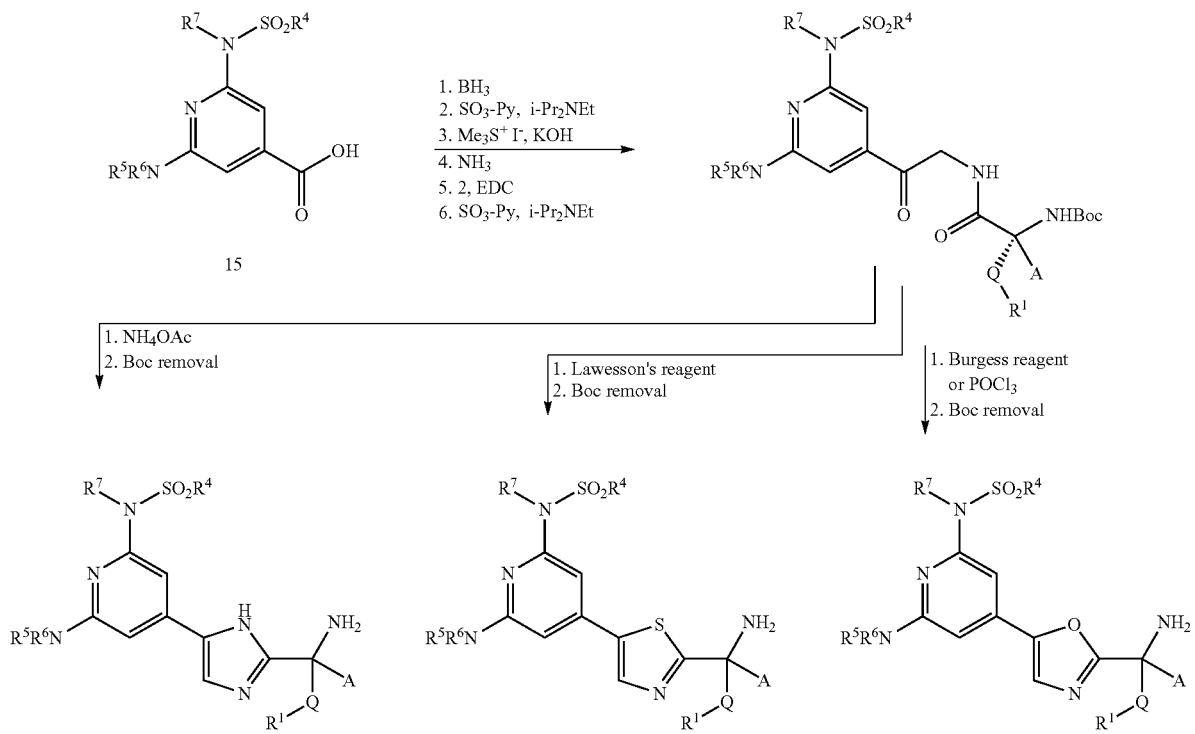

A second series of regioisomeric oxazoles and thiazoles can be synthesized from aryl bromide 16, as described in Scheme 15. Cross coupling, Sharpless asymmetric amination and coupling with acid 2 gives a common intermediate amide-aldehyde. Application of conditions described above provides oxazole 30, thiazole 31, as well as an alternate route to imidazole 29.

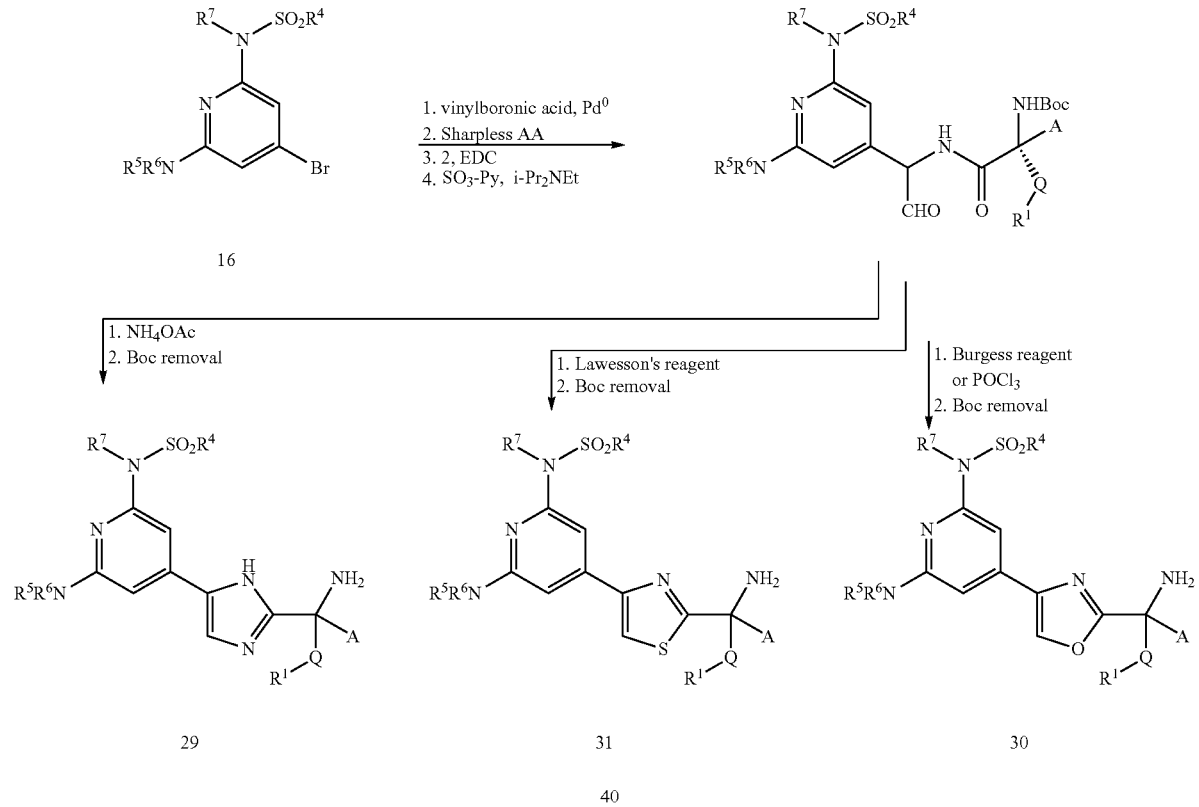

Scheme 16 shows an alternative mode of preparation for heterocycles 29-31. Acid 15 is converted to the corresponding bromoketone, via the intermediate diazoketone. Displacement with carboxamide 6a and cyclization, followed by Boc removal affords oxazole 30. Displacement with thiocarboxamide 6b and cyclization, followed by Boc removal affords thiazole 31. Displacement with acid 2 and cyclization in the presence of an ammonia source, followed by Boc removal affords imidazole 29.

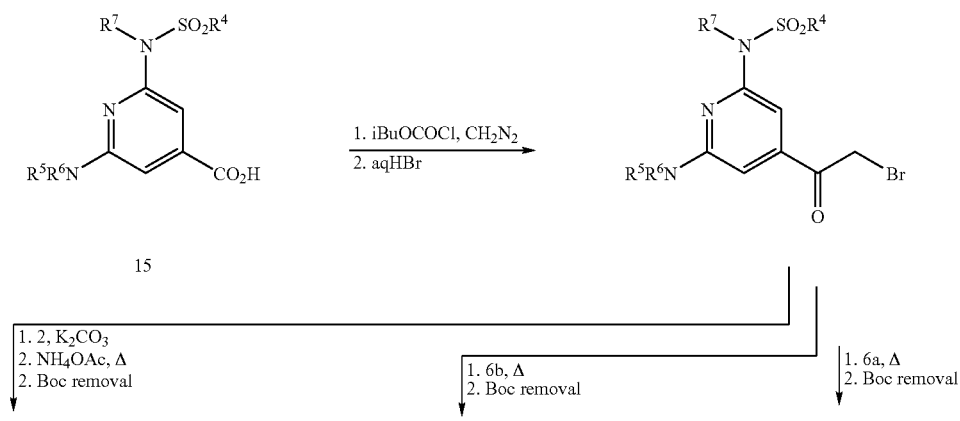

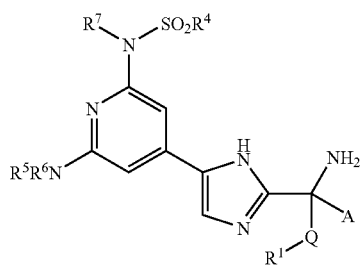

29

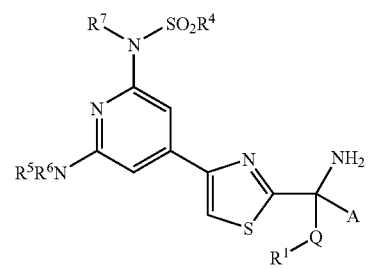

31

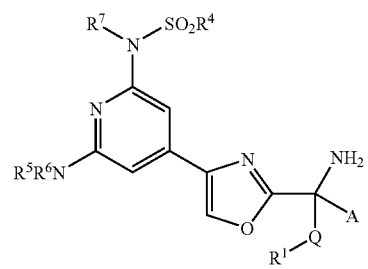

30

Shown below in Scheme 17 is the synthesis of a third series of regioisimeric oxazoles 32, thiazoles 33 and imidazoles 34. Coupling acid 15 with amino alcohol 12, cyclodehydration under the appropriate conditions followed by Boc deprotection provides the desired compounds.

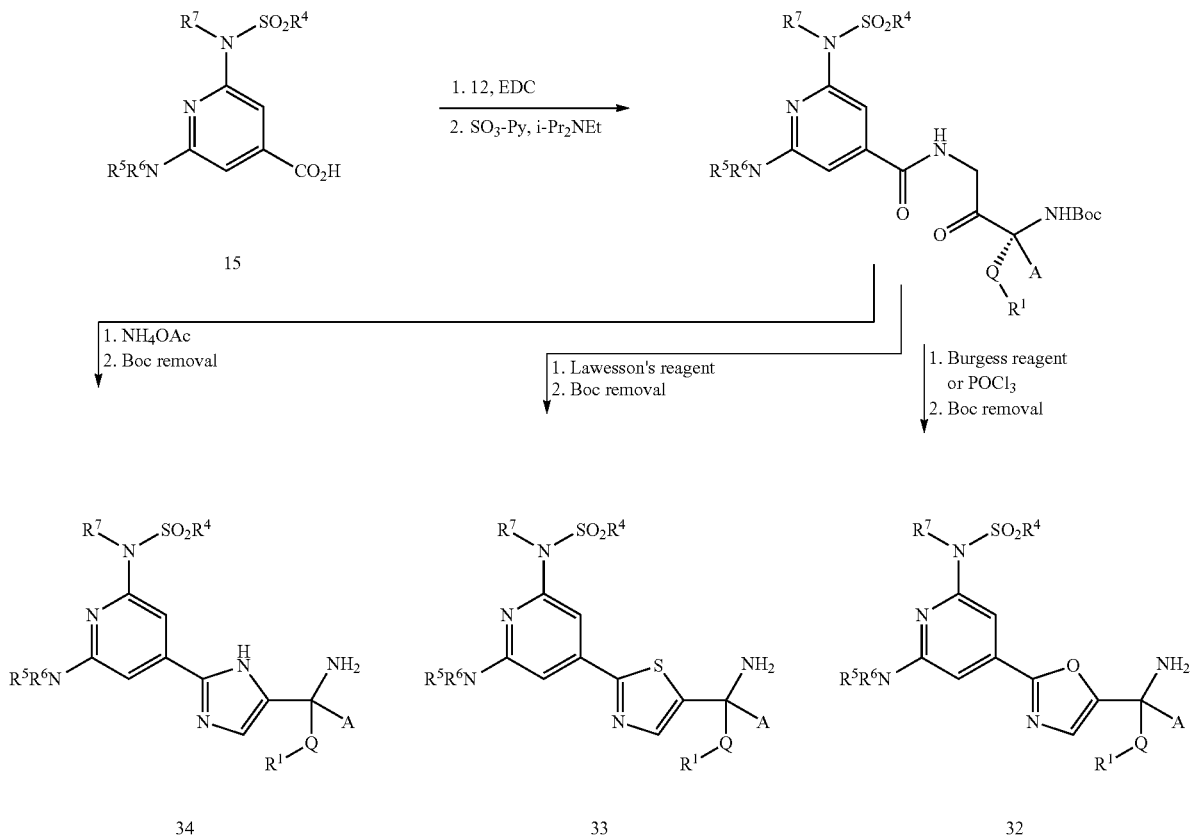

The synthesis of a fourth possible permutation of oxazoles 35, thiazoles 36 is shown in Scheme 18. EDC coupling of aminoalcohol 13 with the acid 15 gives a common intermediate aldehyde-amide. Cyclodehydration under the appropriate conditions will give the desired five membered heterocycle.

Scheme 18

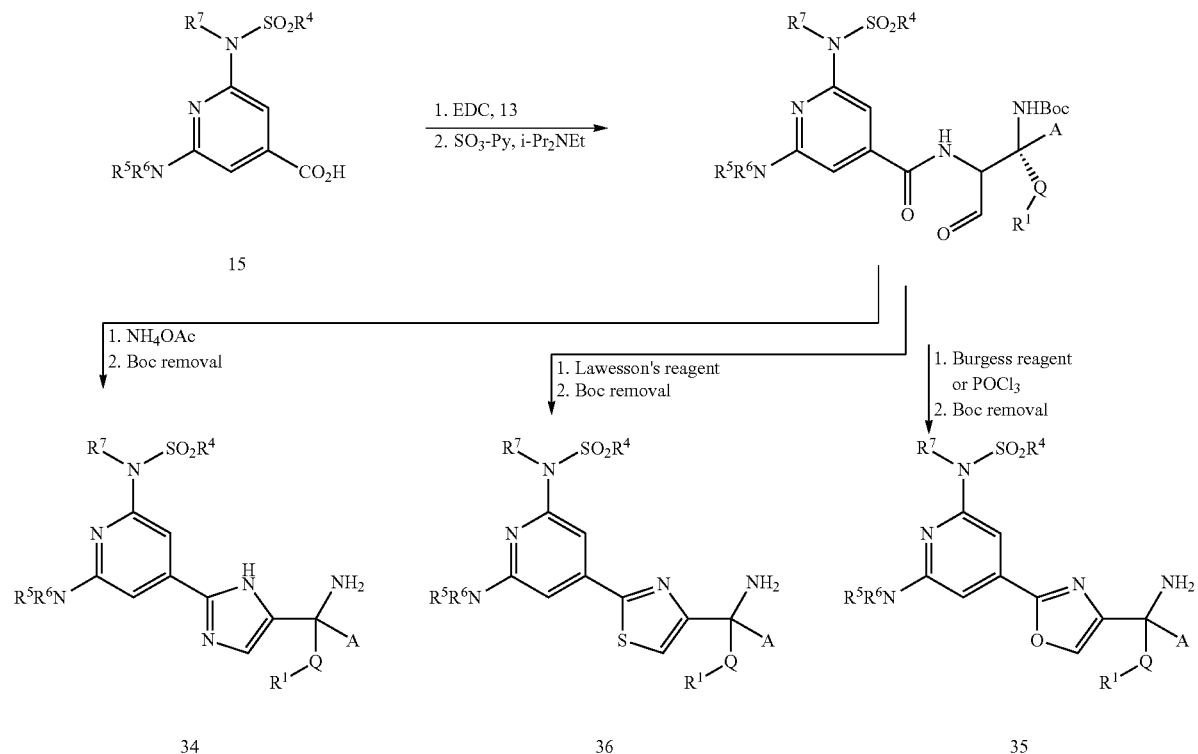

Scheme 19 shows an alternative mode of preparation for heterocycles 34-36. Displacement of bromoketone 14 with acid 15, cyclization in the presence of an ammonia source, followed by Boc removal affords imidazole 34. Displacement with carboxamide 37 and cyclization, followed by Boc removal affords oxazole 35. Displacement with thiocarboxamide 38 and cyclization, followed by Boc removal affords thiazole 36.

Scheme 19

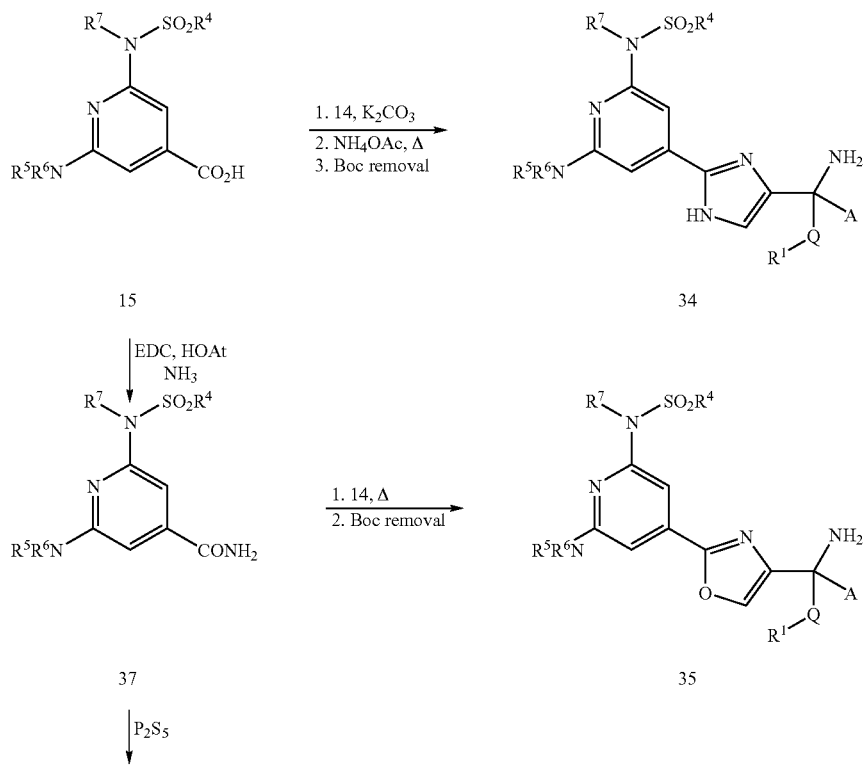

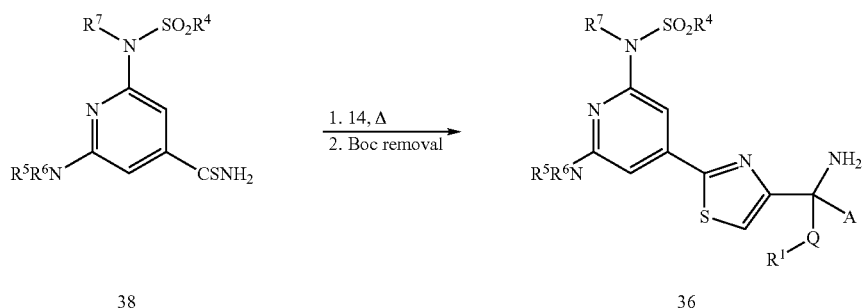

Isoxazoles of type 40 can be prepared as described in Scheme 20. Cross coupling of aryl bromide 16 with TMS acetylene and deprotection gives 39. Cycloaddition with the nitrile oxide derivative prepared from the in-situ oxidation of 11, followed by Boc deprotection gives 40.

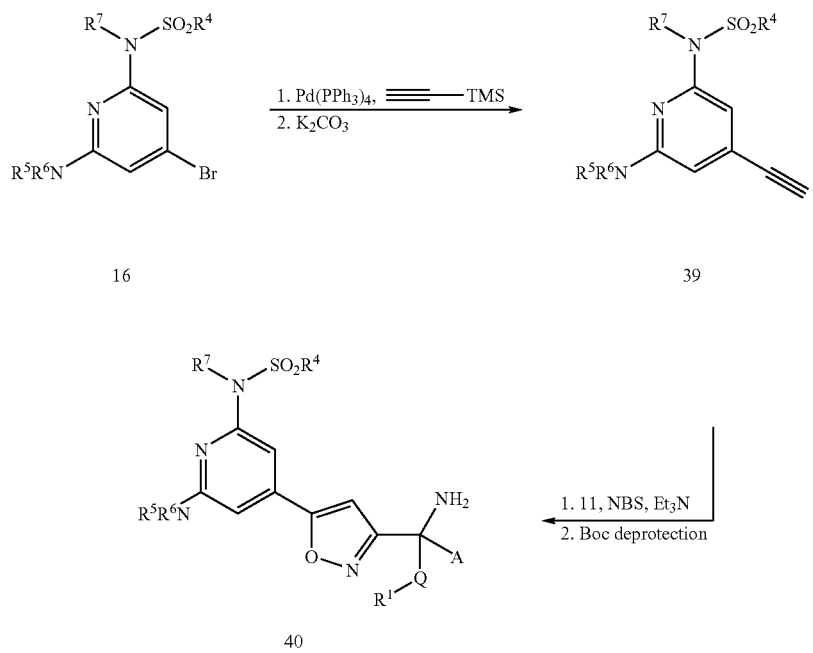

The synthesis of the second isoxazole regioisomer can be accomplished using a sequence similar to that described in Scheme 20. Aldehyde 10 can be elaborated to alkyne 41 utilizing Corey-Fuchs methodology. Acid reduction, oxidation and hydroxy imidate formation gives 42. In situ nitrile oxide generation from 41 and cycloaddition, followed by Boc group removal affords isoxazole 43.

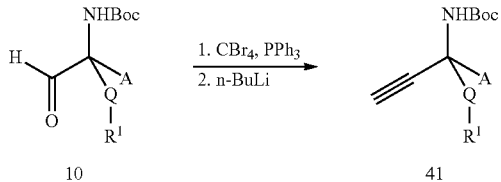

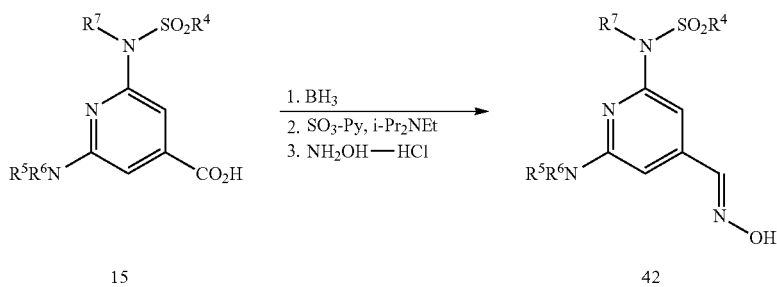
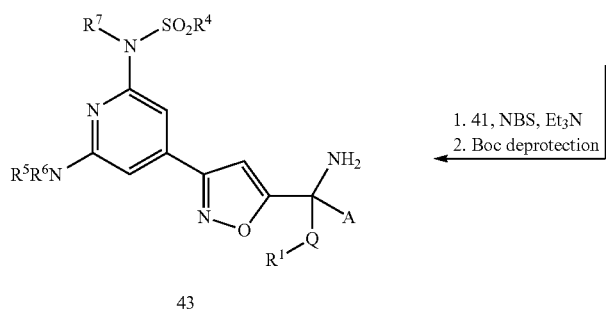
Scheme 22 describes the preparation of intermediates 49, to be used in the elaboration of oxadiazoles of type 50. Carboxylic acid 48 can also be used for the elaboration of various heterocycles as described in previous schemes.
Scheme 22
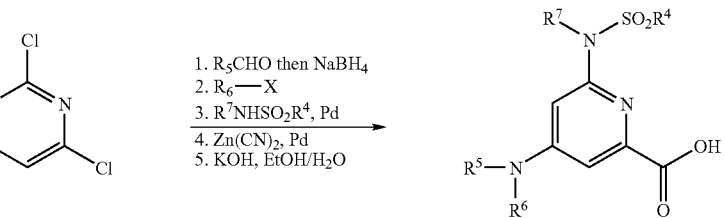
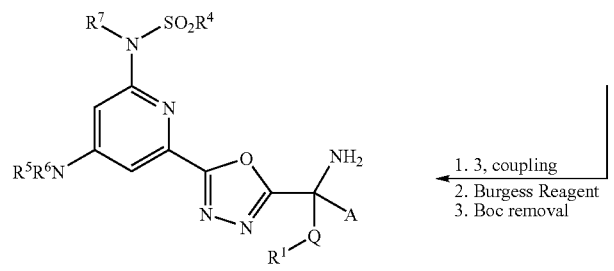

Scheme 23 depicts the synthesis of compounds of the invention having a pyrazole or pyrimidine X group.
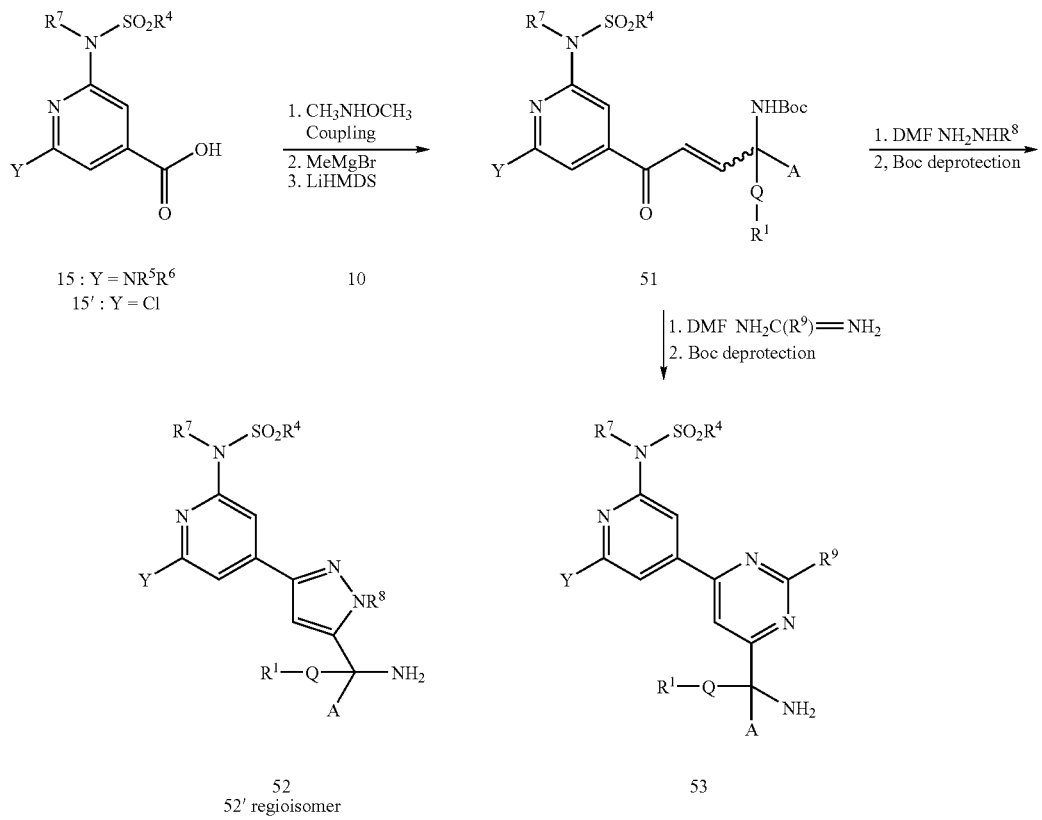
Scheme 24 describes the preparation of intermediates 54, to be used in the elaboration of oxadiazoles of type 55. Carboxylic acid 54 can also be used for the elaboration of various heterocycles as described in previous schemes.
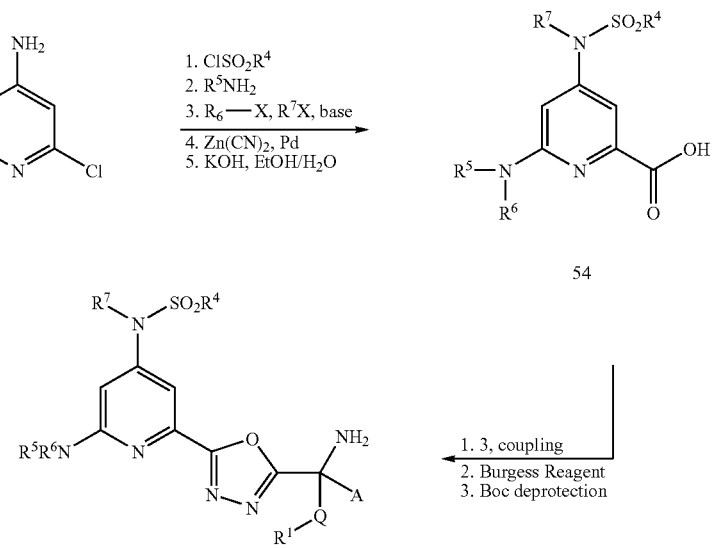

Scheme 25 depicts the synthesis of compounds of type 58. Diazotization of commercial 2-chloro-4-amino-6-chloropyridine and iodination followed by Suzuki cross-coupling provides furan aldehyde 56. Grignard addition followed by oxidation and subsequent organometallic addition provides intermediate alcohol 57. Incorporation of $R^4$ and $R^7$ as before, followed by Ritter reaction, $R^5$ and $R^6$ installation and azide reduction provides final structures of type 58.

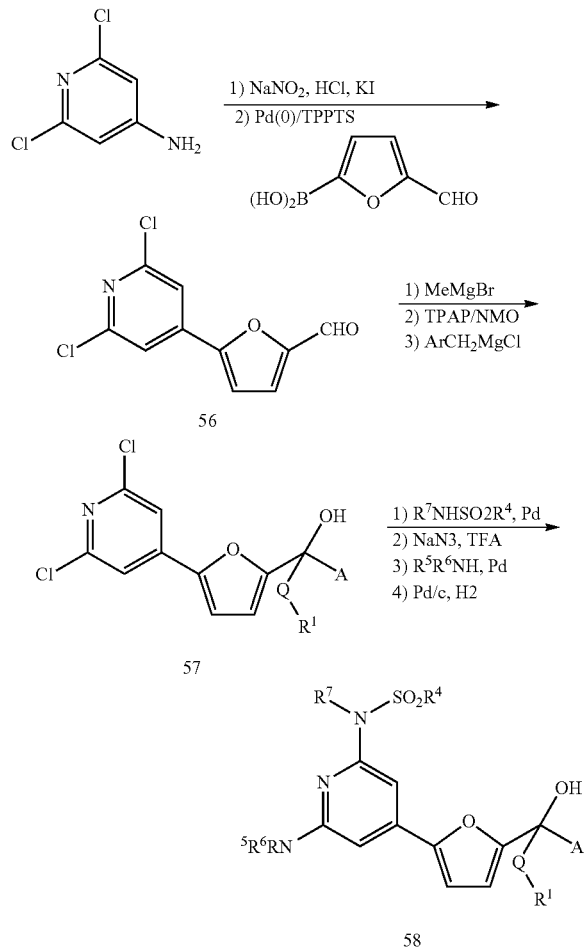

Scheme 25

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, trifluoroacetic, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; tau phosphorylation inhibitors; blockers of Aβ oligomer formation; p25/CDK5 inhibitors; FMG-CoA reductase inhibitors; NSAID's including ibuprofen; vitamin E; anti-amyloid antibodies; NK1/NK3 receptor antagonists; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; P-450 inhibitors such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is employed using a biotinylated BACE substrate. The Km of the substrate is greater than 100 μM and can not be determined due to the limit of solubility of the substrate. A typical reaction contains approximately 0.1 nM enzyme, 0.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and is then stopped by the addition of 25 μL of 1 M Tris-HCl, pH 8.0. The resulting enzymatic product is assayed by adding a ruthenylated antibody which specifically recognizes the C-terminal residue of the product. Streptavidin coated magnetic beads are added into the solution and the samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared starting from 100 μM with three fold series dilution) are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction is proceeded for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, solutions of inhibitor in DMSO (12 concentrations of the inhibitors are prepared and the concentration rage is dependent on the potency predicted by ECL) are included in the reaction mixture (final DMSO concentration is 10%). All experiments are conducted at rt using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in one or both of the aforementioned assays, generally with an $IC_{50}$ from about 1 nM to 100 μM. Such a result is indicative of the intrinsic activity of the compounds in use as inhibitors of the beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

Intermediate I: R-N-(tert-butoxycarbonyl)-α-methylphenylalaninhydrazamide (Scheme 1)

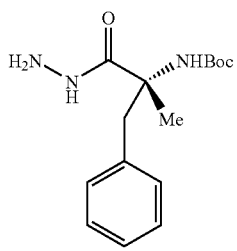

Step A: Boc Protection

To a slurry of D-α-methyl phenylalanine (1.00 g, 5.58 mmol) in 20 mL dioxane was added 3N NaOH (7.4 mL, 22.32 mmol) and $Boc_2O$ (1.28 g, 5.86 mmol). The reaction was allowed to proceed for 14 h. The pH was lowered to ~1 by adding 1N HCl dropwise, diluted with water, and extracted aqueous with EtOAc (3x). Dried combined organics over $Na_2SO_4$, filtered and concentrated to obtain the desired product as a white foam. This was used without further purification. $^1$H NMR ($d_4$-MeOH) δ 7.25-7.17 (m, 3H), 7.12 (d, J=6.6 Hz, 2H), 3.27 (d, J=13.4 Hz, 1H), 3.15 (d, J=13.4 Hz, 1H), 1.45 (s, 9H), 1.39 (s, 3H). LCMS [(M-Boc)+H]$^+$=180

Step B: Hydrazinyl Amide Formation

To a solution of R-N-Boc-α-methyl phenylalanine from step A (1.50 g, 5.37 mmol) in 25 mL $CH_3CN$ was added EDC (1.75 g, 9.13 mmol), followed by hydrazine (0.421 mL, 13.43 mmol). A white precipitate formed immediately, and the solution gradually turned clear over 1 h. The reaction was allowed to proceed at rt overnight, when it was quenched by the addition of saturated aqueous $NaHCO_3$ solution, and diluted with EtOAc. The layers were separated, and the aqueous layer was washed with fresh EtOAc (3x). The combined organic layers were dried over $Na_2SO_4$, filtered and concentrated to afford a white foam, which was used without further purification. $^1$H NMR ($d_4$-MeOH) δ 7.27-7.20 (m, 3H), 7.11 (d, J=7.7 Hz, 2H), 3.30 (d, J=13.5 Hz, 1H), 3.02 (d, J=13.5 Hz, 1H), 1.46 (s, 9H), 1.31 (s, 3H). LCMS [[(M-Boc)+H]$^+$=194

Intermediate II: R-N-(tert-butoxycarbonyl)-α-methylphenylalaninamide (Scheme 2)

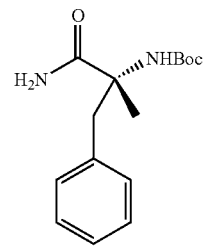

To a solution of N-Boc-D-alpha-methyl phenylalanine (2.04 g, 7.30 mmol) in 26 mL $CH_2Cl_2$ was added EDC (1.54 g, 8.03 mmol), followed by HOAt (0.845 g, 6.21 mmol). After 30 min at rt, 15 mL DMF was added, the reaction was cooled to −10° C., and gaseous ammonia was bubbled through the reaction for 50 min. The reaction was quenched by the addition of satd. aqueous $NaHCO_3$ and diluted with EtOAc. The layers were separated, and the aqueous layer was washed with fresh EtOAc (2x). The combined organics were washed with aqueous 3M LiCl and brine, dried over $Na_2SO_4$, filtered and concentrated. The residue was purified by normal phase chromatography (0->6% MeOH($CH_2Cl_2$)) to afford the desired carboxamide as a white solid. $^1$H NMR ($d_4$-MeOH) 87.96 (br s, 1H), 7.28-7.13 (m, 3H), 7.12 (d, J=7.4 Hz, 2H), 6.39 (br s, 1H), 5.81 (br s, 1H), 3.32 (d, J=13.7 Hz, 1H), 3.10 (d, J=13.7 Hz, 1H), 1.44 (s, 9H), 1.40 (s, 3H). LCMS [(M-Boc)+H]$^+$=179.

Intermediate III: tert-butyl (3R-amino-1-benzyl-2RS-hydroxy-1-methylpropyl)carbamate (Schemes 3, 4)

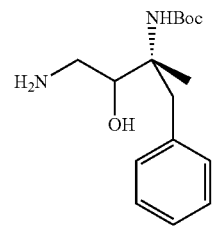

Step A: Reduction

To a solution of D-alpha-methyl-phenylalanine (1.74 g, 9.71 mmol) in 30 mL THF at rt was added $NaBH_4$ (0.92 g 24.27 mmol) in one portion. The solution was cooled to 0° C. Iodine (2.46 g, 9.71 mmol) in 5 mL THF was added dropwise over 30 min. After the addition was complete, the reaction was heated to reflux for 2 days. The reaction was then cooled to 0° C. and quenched by the addition of methanol until the bubbling subsided. The reaction mixture was acidified by the addition of 6N HCl until pH 1, stirred at 50° C. for 30 min and concentrated in vacuo. Purification using ion exchange chromatography (SCX cartridge) afforded 2R-amino-2-methyl-3-phenylpropan-1-ol as a white solid. $^1$H NMR (400 MHz, $CDCl_3$) δ 7.35-7.18 (m, 5H), 3.36 (A of AB, d, J=10.4 Hz, 1H), 3.31 (B of AB, d, J=10.4 Hz, 1H), 2.70 (s, 2H), 1.04 (s, 3H).

Step B: Boc Protection

A solution of 2R-amino-2-methyl-3-phenylpropan-1-ol (4.14 g, 25 mmol) and ditertbutyldicarbonate (7.1 g, 32.5 mmol) was stirred at rt for 16 h, concentrated in to provide tert-butyl (1-benzyl-2R-hydroxy-1-methylethyl)carbamate), as a white solid. $^1$H NMR (400 MHz, CDCl$_3$) δ 7.35-7.15 (m, 5H), 4.48 (br s, 1H), 4.17 (br s, 1H), 3.76-3.62 (m, 2H), 3.19 (A of AB, d, J=13.6 Hz, 1H), 2.81 (B of AB, d, J=13.6 Hz, 1H), 1.47 (s, 9H), 1.07 (s, 3H).

Step C: Oxidation

To a solution of tert-butyl (1-benzyl-2R-hydroxy-1-methylethyl)carbamate (6.7 g, 25.2 mmol) in DCM (100 mL) and DMSO (25 mL) was added triethylamine (10.5 mL, 75.7 mmol) and sulfurtrioxide-pyridine (10 g, 63.1 mmol). The reaction mixture was stirred at rt for 3.5 h, diluted with EtOAc, washed with 10% KHSO$_4$, saturated NaHCO$_3$, water, brine and aq LiCl, dried over sodium sulfate, concentrated in vacuo and purified by flash chromatography (silica, 0-20% EtOAc/hexanes) to provide tert-butyl (1-benzyl-1-methyl-2R-oxoethyl)carbamate as a white solid. $^1$H NMR (400 MHz, CDCl$_3$) δ 9.53 (s, 1H), 7.35-7.22 (m, 3H), 7.12-7.00 (m, 2H), 4.84 (br s, 1H), 3.17 (A of AB, d, J=13.6 Hz, 1H), 3.08 (B of AB, d, J=13.6 Hz, 1H), 1.51 (s, 9H), 1.27 (s, 3H).

Step D: Epoxidation

To a solution of N-(tert-butyl (1-benzyl-1-methyl-2R-oxoethyl)carbamate (1 g, 3.80 mmol) in acetonitrile (15 mL) was added 6 drops water, trimethylsulfonium iodide (775 mg, 3.80 mmol) and potassium hydroxide (511 mg, 9.11 mmol). The reaction was stirred at 60° C., sealed, for 1.5 h, additional trimethylsulfonium iodide (775 mg, 3.80 mmol) and potassium hydroxide (511 mg, 9.11 mmol) were added and the reaction was stirred at 60° C., sealed, for 3 h. The reaction mixture was diluted with EtOAc, washed with sat'd aq NaHCO$_3$, brine, dried over sodium sulfate, and concentrated in vacuo to provide tert-butyl (1-methyl-1-oxiran-2R-yl-2-phenylethyl)carbamate as an oil. MS (ES, M+H) 278.

Step E: Epoxide Opening

A solution of tert-butyl (1-methyl-1-oxiran-2R-yl-2-phenylethyl)carbamate (986 mg, 3.56 mmol) in EtOH (35 mL) and NH$_4$OH (35 mL) was stirred at 60° C., sealed, for 16 h, concentrated in vacuo and purified by flash chromatography (silica, 0-30% (10% NH$_4$OH/MeOH)/CH$_2$Cl$_2$) to provide tert-butyl (3R-amino-1-benzyl-2RS-hydroxy-1-methylpropyl)carbamate as a thick oil. $^1$H NMR (400 MHz, CD$_3$OD, 1:1 diastereomeric mixture) δ 7.30-7.14 (m, 5H), 4.01 (br d, J=9.2 Hz, 0.5 H), 3.54 (dd, J=10.0, 2 Hz, 0.5 H), 3.39 (br s, 0.5H), 3.36 (br s, 0.5H), 2.94-2.56 (m, 4H), 1.47 (s, 9H), 1.03 (s, 1.5 H), 0.99 (s, 1.5H).

Intermediate IV: N 2-[(tert-butoxcycarbonyl)amino]-2-methyl-3pyridin -4-ylpropanoic acid (Scheme 1)

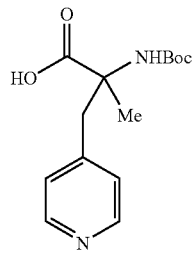

Step A: Schiff Base Formation

To a solution of alanine methyl ester hydrochloride (10.0 g, 71.6 mmol) in 100 mL CH$_2$Cl$_2$ was added benzophenone imine (12.0 mL, 71.6 mmol). A white ppt gradually came out of solution as the reaction was allowed to proceed at rt for 15 h. The reaction was diluted with H$_2$O and CH$_2$Cl$_2$, and the layers were separated, the organic layer was washed with brine, dried over Na$_2$SO$_4$, filtered and concentrated to afford methyl-N-(diphenylmethylene)alaninate as a viscous oil which was used without further purification. $^1$H NMR (CDCl$_3$, 400 MHz) δ 7.62 (m, 2H), 7.47-7.29 (m, 6H), 7.19-7.16 (m, 2H), 4.16 (q, J=6.8 Hz, 1H), 3.7 (s, 3H), 1.40 (d, J=6.8 Hz, 3H).

Step B: Alkylation

To a solution of methyl N-(diphenylmethylene)alaninate from Step A (9.78 g, 36.6 mmol) in 60 ml DMF at 0° C. was added a 1M solution of sodium bis(trimethylsilyl)amide in THF (45.72 ml, 45.72 mmol) over a 20 min period. After 30 min, a solution of 4-picolyl chloride hydrochloride (3.00 g, 18.29 mmol) in 40 ml DMF was added to the reaction via cannula over a 25 min period. The reaction was warmed to rt and stirred for 5 h. The reaction was quenched with saturated aqueous NH$_4$Cl and extracted with EtOAc (3×). The combined organic layers were washed with 3M LiCl (2×) and brine, dried over Na$_2$SO$_4$, filtered, and concentrated in vacuo. Purification by silica gel chromatography (0-40% EtOAc/hexanes) afforded methyl 2-[(diphenylmethylene)amino]-2-methyl-3-pyridin-4-ylpropanoate as a white solid (5.28 g, 81%). LCMS [M+H]=359.2. $^1$H NMR (d$_4$-MeOH) δ 8.51 (dd, J=4.5, 1.5 Hz, 2H), 7.56 (dd, J=8.4, 1.4 Hz, 2H), 7.40-7.37 (m, 4H), 7.34-7.30 (m, 2H), 7.26-7.23 (m, 2H), 7.10-7.07 (m, 2H), 3.33 (A of AB, d, J=13.0 Hz, 1H), 3.27 (s, 3H), 3.18 (B of AB, d, J=12.9 Hz, 1H), 1.32 (s, 3H).

Step C: Removal of Schiff Base

To a suspension of methyl 2-[(diphenylmethylene)amino]-2-methyl-3-pyridin-4-ylpropanoate from Step B (5.28 g, 14.73 mmol) in 75 ml of 1:1 MeOH/THF was added 6N HCl (3.68 ml, 22.10 mmol). The reaction was concentrated in vacuo after stirring for 1.5 h at rt. Purification using ion exchange chromatography (SCX cartridge) afforded methyl 2-amino-2-methyl-3-pyridin-4-ylpropanoate as a yellow oil (2.76 g, 97%). LCMS [M+H]=195.3. $^1$H NMR (d$_4$-MeOH) δ 8.43 (dd, J=4.6, 1.6 Hz, 2H), 7.24 (dd, J=4.6, 1.5 Hz, 2H), 3.70 (s, 3H), 3.09 (A of AB, d, J=12.9 Hz, 1H), 2.90 (B of AB, d, J=13.0 Hz, 1H), 1.39 (s, 3H).

Step D: Boc Protection

To a suspension of methyl 2-amino-2-methyl-3-pyridin-4-ylpropanoate from Step C (2.76 g, 14.21 mmol) in 70 ml THF at 0° C. was added di-tert-butyl dicarbonate (4.03 g, 18.47 mmol). After 30 min, the reaction was warmed to rt and allowed to proceed over night. The reaction was diluted with EtOAc and washed with saturated aqueous NH$_4$Cl, water, and brine. The organic layer was dried over Na$_2$SO$_4$, filtered, and concentrated in vacuo. Purification on silica gel chromatography (0-60% EtOAc/CH$_2$Cl$_2$) afforded methyl 2-[(tert-butoxycarbonyl)amino]-2-methyl-3-pyridin-4-ylpropanoate as a yellow solid (3.22 g, 77%). LCMS [M+H]=295.2. $^1$H NMR (400 MHz, d$_4$-MeOH) δ 8.43 (d, J=5.1 Hz, 2H), 7.21 (d, J=5.9 Hz, 2H), 3.73 (s, 3H), 3.44 (A of AB, d, J=13.2 Hz, 1H), 3.12 (B of AB, d, J=13.2 Hz, 1H), 1.46 (s, 9H), 1.30 (s, 3H).

Step E: Saponification

To a solution of methyl 2-[(tert-butoxycarbonyl)amino]-2-methyl-3-pyridin-4-ylpropanoate from Step D (0.25 g, 0.85 mmol) in 4.25 ml of 1:1 MeOH/THF was added 3N NaOH (0.43 ml, 1.27 mmol). The reaction was allowed to proceed at 50° C. for 1 h, at which point it was cooled to rt and quenched with 6N HCl (0.21 ml, 1.27 mmol). The reaction was concentrated in vacuo to yield 2-[(tert-butoxycarbonyl)amino]-2-methyl-3-pyridin-4-ylpropanoic acid NaCl as a white solid. LCMS [M+H]=281.3. $^1$H NMR (400 MHz, d$_4$-MeOH) δ 8.44 (d, J=5.3 Hz, 2H), 7.28 (d, J=5.9 Hz, 2H), 3.43 (A of AB, d, J=12.6 Hz, 1H), 3.33 (B of AB, d, J=12.3 Hz, 1H), 1.47 (s, 9H), 1.41 (s, 3H).

Intermediate V:
N-(tert-butoxycarbonyl)-2,5-dimethylnorleucine
(Scheme 1)

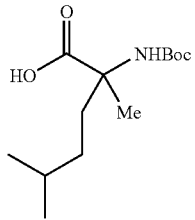

N-(tert-butoxycarbonyl)-2,5-dimethylnorleucine was prepared from isobutyl iodide and the alanine Schiff based as described for the preparation of intermediate IV.

Intermediate A:
N-benzyl-1-(2-trans-methylcyclopropyl)methanamine

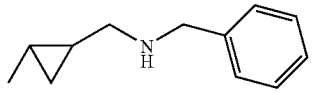

Step A: Coupling

In a 2 L flask trans-crotonoic acid (15.0 g, 174 mmol), benzyl amine (20.5 g, 192 mmol) and DIPEA (36.7 g, 192 mmol) were dissolved in 700 mL of dichloromethane. To this solution at rt EDC-HCl (36.7 g, 192 mmol) was added as a solid portionwise and stirred overnight. The reaction mixture was poured onto 10% aq. KHSO$_4$ (250 mL). The layers were separated and washed once again with 10% aq. KHSO$_4$. The organic layer was subsequently washed with H$_2$O (200 mL) followed by brine (150 mL), dried over Na$_2$SO$_4$ and concentrated to dryness to white crystals of (2E)-N-benzylbut-2-enamide: $^1$H NMR (400 MHz, CDCl$_3$) δ 7.28 (m, 5H), 6.85 (sext, J=6.8 Hz, 1H), 5.78 (dd, J=15.2, 1.6 Hz, 2H), 4.47 (d, J=5.6 Hz, 2H), 1.82 (dd, J=7.2, 1.6 Hz, 3H).

Step B: Cyclopropanation

In an Erlenmeyer flask containing Et$_2$O (300 mL) and aq. 40% KOH (11 mL) with vigorous stirring was added 1-methyl-3-nitro-1-nitrosoguanidine (11.1 g, 67 mmol) portionwise over 5 min. at rt. Upon complete addition stirring was ceased and the aq. layer frozen in a −78° bath. The ether layer was decanted into an Erlenmeyer with KOH pellets. The contents allowed to stand for 5 min., decanted into a third flask with KOH pellets and then poured onto a Et$_2$O/THF solution (200 mL/50 mL) containing (2E)-N-benzylbut-2-enamide (3.0 g, 17.1 mmol from step A). Pd(OAc)$_2$ (180 mg, 0.9 mmol) was subsequently added and the reaction allowed to warm to rt and stir for 1 h. Nitrogen was bubbled through the reaction for 10 min. The mixture was washed with H$_2$O (150 mL). The organic layer was isolated and subsequently dried over Na$_2$SO$_4$. Solvent removal and purification by flash chromatography on SiO$_2$ (EtOAc/hexanes) gave N-benzyl-trans-2-methylcyclopropanecarboxamide (83%): $^1$H NMR (400 MHz, CDCl$_3$) δ 7.28 (m, 5H), 5.81 (br s, 1H), 4.43 (dd, J=5.6, 2.4 Hz, 2H), 1.37 (m, 1H), 1.17 (m, 1H), 1.07 (d, J=6.0 Hz, 3H), 1.04 (overlapping m, 1H), 0.56 (m, 1H).

Preparative chiral HPLC is optionally performed to afford the preferred enantiomer trans-S,S. In the following intermediates and examples, either the preferred enantiomer trans-S,S or the racemic mixture trans-S,S and trans-R,R were used without discrimination. For simplification, the methyl-cyclopropyl-methyl moiety is drawn as trans-racemic.

Step C: Reduction

A 500 mL flask charged with N-benzyl-trans-2-methylcyclopropanecarboxamide (from step B, 3.9 g, 20.6 mmol) in THF (80 mL). BH$_3$-THF (1.0 M, 105 mL, 105 mmol) was added dropwise via an addition funnel. Upon complete addition (10 min.) the mixture was refluxed for 5 h. The mixture was allowed to cool to rt and quenched carefully with MeOH (15 mL). The mixture was concentrated to dryness, dissolved in dichloromethane and washed with 3M KOH. The organic layer was isolated, washed with brine, then dried over Na$_2$SO$_4$ and concentrated to dryness. The crude material was treated with 1N HCl in dioxane for 1 h at 50° C. The mixture was concentrated to give hydrochloride salt as a white solid. The solid was dissolved in sat. aq. NaHCO$_3$ (80 mL) and extracted with CHCl$_3$ (2×150 mL). The combined organic layers were washed with brine, dried over Na$_2$SO$_4$ and the solvent removed via rotorary evaporation to give after drying in vacuo N-benzyl-1-(2trans -methylcyclopropyl)methanamine as an off-white semi-solid (quant.): $^1$H NMR (400 MHz, CDCl$_3$) δ 7.28 (m, 5H), 3.80 (s, 2H), 2.50 (d, J=6.8 Hz, 2H), 2.4 (br s, 1H), 1.02 (d, J=6.0 Hz, 3H), 0.69 (m, 1H), 0.52 (m, 1H), 0.23 (m, 2H).

Intermediate B:
N-methyl-1-(2-trans-methylcyclopropyl)methanamine

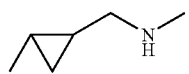

To a solution of N-benzyl-1-(2-trans-methylcyclopropyl)methanamine (8 g, 45.6 mmol, intermediate A) in DCE (240 mL) and MeOH (120 mL) was added formaldehyde (34 mL, 456 mmol, 37% aqueous) and NaBH(OAc)$_3$ (19.3 g, 91 mmol). The reaction mixture was stirred at rt for 1 h, treated with sat'd aq NaHCO$_3$, concentrated near dryness, diluted with water and extracted with EtOAc (3×). The combined organic layer was washed with brine, dried over sodium sulfate, treated with HCl (50 mL, 50 mmol, 1M Et$_2$O), and concentrated in vacuo to afford N-benzyl-methyl-1-(2trans-methylcyclopropyl)methanamine as the hydrochloride which was hydrogenated in the presence of 20% Pd(OH)$_2$/C (616 mg), in EtOH (400 mL), at 60° C., under 1 atm H$_2$ for 2 h. Filtration and concentration in vacuo provided N-methyl-1-(2-trans-methylcyclopropyl)methanamine as the hydrochloride. $^1$H NMR (400 MHz, CD$_3$OD) δ 2.88 (d, J=7.3 Hz, 2H), 2.69 (s, 3H), 1.09 (d, J=5.7 Hz, 3H), 0.78-0.70 (m, 2H), 0.52-0.50 (m, 1H), 0.50-0.40 (m, 1H).

Intermediate C: 2-{benzyl[(2-methylcyclopropyl) methyl]amino}-6-[methyl(methylsulfonyl)amino] isonicotinic acid (Scheme 7)

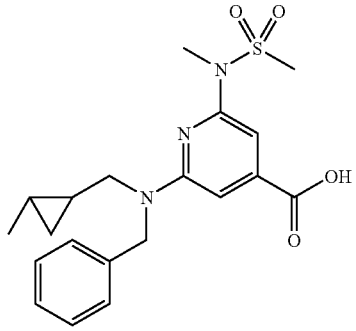

Step A: Sulfonamide Incorporation

Methyl 2,6-dichloroisonicotinate (5.0 g, 24.3 mmol), methyl(methylsulfonyl)amine (3.18 g, 29.12 mmol), potassium phosphate (7.22 g, 34.0 mmol), Xantphos (0.87 g, 1.50 mmol) and tris(dibenzylideneacetone)dipalladium (0.68 g, 0.51 mmol) were added to a dry, argon flushed flask. Dioxane (195 mL) was added, the solution degassed with argon and the reaction was heated to 100° C. for 16 hours. The reaction was cooled to rt, filtered through celite and evaporated in vacuo. Flash chromatography (silica, 0-50% EtOAc/CH$_2$Cl$_2$) gave methyl 2chloro -6-[methyl(methylsulfonyl)amino]isonicotinate as a yellow oil: $^1$H NMR (400 MHz, CDCl$_3$) δ 7.88 (s, 1H), 7.68 (s, 1H), 3.96 (s, 3H), 3.44 (s, 3H), 3.11 (s, 3H).

Step B: Hydrolysis

To a solution of methyl 2-chloro-6-[methyl(methylsulfonyl)amino]isonicotinate (2 g, 7.18 mmol) in 1:1 THF:MeOH (60 mL) added a NaOH (9.3 mL, 9.3 mmol, 1N). The reaction mixture was stirred at rt for 0.5 h, acidified to pH 3-4 with 1N HCl, extracted with dichloromethane (×2), dried over sodium sulfate and concentrated in vacuo to provide 2-chloro-6-[methyl(methylsulfonyl)amino]isonicotinic acid as a white solid. $^1$H NMR (400 MHz, CD$_3$OD) δ 7.88 (s, 1H), 7.63 (s, 1H), 3.39 (s, 3H), 3.13 (s, 3H).

Step C: Amination

A suspension of 2-chloro-6-[methyl(methylsulfonyl) amino]isonicotinic acid (1.2 g, 4.53 mmol), Intermediate A (1.85 g, 10.55 mmol), potassium phosphate (3.18 g, 15.1 mmol), and palladium bis(tri-t-butylphosphine) (0.13 g, 0.25 mmol) in degassed DMA (10 mL) was sealed in a glass tube and heated to 130° C. for 4 hours. The reaction mixture was diluted with water and brine, acidified to pH 3-4 with 1N HCl, extracted with dichloromethane and concentrated in vacuo. The residue was taken in EtOAc, washed with aq LiCl (×3), dried on Na$_2$SO$_4$, concentrated in vacuo and purified by flash chromatography (silica, 2-7% (1% AcOH in MeOH)/ CH$_2$Cl$_2$) to provide 2-{benzyl[(2-methylcyclopropyl)methyl]amino}-6-[methyl(methylsulfonyl)amino]isonicotinic acid as an oil. $^1$H NMR (400 MHz, CDCl$_3$) δ 7.35-7.15 (m, 5H), 7.06 (s, 1H), 7.03 (s, 1H), 4.59-4.28 (m, 2H), 3.55 (A of ABX, dd, J=14.8, 5.6 Hz, 1H), 3.29 (B of ABX, dd, J=14.8, 7.2 Hz, 1H), 3.28 (s, 3H), 2.87 (s, 3H), 0.97 (d, J=6.4 Hz, 3H), 0.84-0.74 (m, 1H), 0.66-0.56 (m, 1H), 0.40-0.31 (m, 1H), 0.29-0.21 (m, 1H).

Intermediate D: 2-{methyl[(2-methylcyclopropyl) methyl]amino}-6-[methyl(methylsulfonyl)amino] isonicotinic acid (Scheme 7)

2-{methyl[(2-methylcyclopropyl)methyl]amino}-6-[methyl(methylsulfonyl)amino]isonicotinic acid was prepared from 2-chloro-6-[methyl(methylsulfonyl)amino]isonicotinic acid and N -methyl-1-(2-trans-methylcyclopropyl)methenamine using a similar procedure as described in intermediate C preparation, step C. $^1$H NMR (400 MHz, CD$_3$OD) δ 7.02 (s, 1H), 6.96 (s, 1H), 3.55 (A of ABX, dd, J=14.4, 6.0 Hz, 1H), 3.29 (B of ABX, dd, J=14.4, 7.2 Hz, 1H), 3.35 (s, 3H), 3.15 (s, 3H), 3.12 (s, 3H), 1.03 (d, J=6.0 Hz, 3H), 0.82-0.66 (m, 2H), 0.48-0.41 (m, 1H), 0.28-0.22 (m, 1H).

Intermediate E: N-(4-(bromoacetyl)-6-{methyl[(2-methylcyclopropyl)methyl]amino}pyridin-2-yl)-N-methylmethanesulfonamide (Scheme 16)

To a solution of Intermediate D (250 mg, 0.76 mmol) in THF (3 mL) cooled to −78° C. was added N-methylmorpholine (0.088 mL, 0.8 mmol) and isobutyl chloroformate dropwise (0.104 mL, 0.8 mmol), and the reaction mixture was stirred at −78° C. for 0.5 h. The reaction mixture was filtered on celite, rinsed with diethyl ether. The filtrate and rinsate was cooled to −20° C. and treated with diazomethane (3.5 mL, Et$_2$O solution prepared from 150 mL Et$_2$O, 40 mL 40% aqKOH and 13.2 g 1-methyl-3-nitro-1-nitrosoguanidine). After stirring at −20° C. for 1.5 h, the reaction mixture was allowed to warm to rt, 5 mL diazomethane solution was added and the reaction mixture was stirred at rt for 0.5 h, concentrated in vacuo (rt bath and HOAc in trap). The residue was dissolved in Et$_2$O and EtOAc, washed with water, brine, dried over sodium sulfate and concentrated in vacuo. The residue was dissolved in Et$_2$O (5 mL), cooled to −20° C., treated with 62% HBr (0.25 mL), stirred at −20° C. for 0.3 h, diluted with Et$_2$O, washed with water, sat. aq. NaHCO$_3$, brine, dried over sodium sulfate and concentrated in vacuo to provide crude N-(4-(bromoacetyl)-6-{methyl[(2-methylcyclopropyl)methyl]amino}pyridin-2-yl)-N-methylmethanesulfonamide as yellow oil. $^1$H NMR (400 MHz, CDCl$_3$) δ 6.96 (s, 1H), 6.80

(s, 1H), 4.40 (s, 2H), 3.52 (A of ABX, dd, J=14.8, 6.4 Hz, 1H), 3.36 (B of ABX, dd, J=14.8, 6.8 Hz, 1H), 3.39 (s, 3H), 3.12 (s, 3H), 3.11 (s, 3H), 1.03 (d, J=6.0 Hz, 3H), 0.78-0.62 (m, 2H), 0.44-0.38 (m, 1H), 0.31-0.26 (m, 1H).

Intermediate F: N-(4-(2-amino-1-hydroxyethyl)-6-{methyl[(2-methylcyclopropyl)methyl]amino}pyridin-2-yl)-N-methylmethanesulfonamide (Scheme 14)

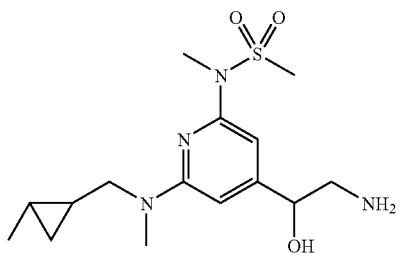

Step A: Reduction

To a solution of Intermediate D (815 mg, 2.49 mmol) in THF (10 mL) cooled to 0° C. was added BH$_3$-THF (7.5 mL, 7.5 mmol, 1M THF) and the reaction mixture was stirred at rt for 2.5 h, carefully quenched with MeOH, then 1N HCl, diluted with EtOAc, washed with 1N HCl, sat'd aq NaHCO$_3$, brine, dried over sodium sulfate, concentrated in vacuo and purified by flash chromatography (silica, 25-70% EtOAc/hexanes) to provide N-(4-(hydroxymethyl)-6-{methyl[(2-methylcyclopropyl)methyl]amino}pyridin-2-yl)-N-methylmethanesulfonamide as a thick oil. $^1$H NMR (400 MHz, CDCl$_3$) δ 6.51 (s, 1H), 6.38 (s, 1H), 4.63 (d, J=6.0 Hz, 2H), 3.50 (A of ABX, dd, J=14.4, 6.4 Hz, 1H), 3.33 (s, 3H), 3.31 (B of ABX, dd, J=14.4, 6.8 Hz, 1H), 3.10 (s, 3H), 3.07 (s, 3H), 1.84 (t, J=6.0 Hz, 1H), 1.02 (d, J=5.6 Hz, 3H), 0.77-0.60 (m, 2H), 0.42-0.35 (m, 1H), 0.27-0.21 (m, 1H).

Step B: Oxidation

To a solution of N-(4-(hydroxymethyl)-6-{methyl[(2-methylcyclopropyl)methyl]amino}pyridin-2-yl)-N-methylmethanesulfonamide (480 mg, 1.53 mmol) in dichloromethane (10 mL) and DMSO (2.5 mL) was added triethylamine (1.07 mL, 7.66 mmol) and SO$_3$-pyridine (975 mg, 6.13 mmol). The reaction mixture was stirred at rt for 0.5 h, diluted with EtOAc, washed with 1N HCl, sat'd aq NaHCO$_3$, brine, dried over sodium sulfate, concentrated in vacuo and purified by flash chromatography (silica, 25-50% EtOAc/hexanes) to provide N-(4-formyl-6-{methyl[(2-methylcyclopropyl)methyl]amino}pyridin-2-yl)-N-methylmethanesulfonamide. $^1$H NMR (400 MHz, CDCl$_3$) δ 9.94 (s, 1H), 6.92 (s, 1H), 6.72 (s, 1H), 3.53 (A of ABX, dd, J=14.8, 6.4 Hz, 1H), 3.40 (s, 3H), 3.36 (B of ABX, dd, J=14.8, 6.8 Hz, 1H), 3.15 (s, 3H), 3.13 (s, 3H), 1.04 (d, J=6.0 Hz, 3H), 0.78-0.62 (m, 2H), 0.45-0.37 (m, 1H), 0.31-0.24 (m, 1H).

Step C: Epoxidation and Epoxide Opening

To a solution of N-(4-formyl-6-{methyl[(2-methylcyclopropyl)methyl]amino}pyridin-2-yl)-N-methylmethanesulfonamide (435 mg, 1.40 mmol) in acetonitrile (5 mL) was added 5 drops water, trimethylsulfonium iodide (342 mg, 1.68 mmol) and potassium hydroxide (188 mg, 3.35 mmol). The reaction was stirred at 65° C., sealed, for 3 h, diluted with EtOAc, washed with sat'd aq NaHCO$_3$, brine, dried over sodium sulfate, and concentrated in vacuo to provide N-methyl-N-(6-{methyl[(2-methylcyclopropyl)methyl]amino}-4-oxiran-2-ylpyridin-2-yl)methanesulfonamide, used as is in the next step. A solution of N-methyl-N-(6-{methyl[(2-methylcyclopropyl)methyl]amino}-4-oxiran-2-ylpyridin-2-yl)methanesulfonamide (440 mg, 1.35 mmol) in EtOH (10 mL) and NH$_4$OH (15 mL) was stirred at 60° C., sealed, for 16 h, concentrated in vacuo and purified by flash chromatography (silica, 5-15% (10% NOH/MeOH)/CH$_2$Cl$_2$) to provide N-(4-(2-amino-1-hydroxyethyl)-6-{methyl[(2-methylcyclopropyl)methyl]amino}pyridin-2-yl)-N-methylmethanesulfonamide as a thick oil. $^1$H NMR (400 MHz, CD$_3$OD) δ 6.52 (s, 1H), 6.47 (s, 1H), 4.58 (X' of A'B'X', dd, J=7.6, 4.0 Hz, 2H), 3.54 (A of ABX, dd, J=14.4, 6.4 Hz, 1H), 3.35 (B of ABX, dd, J=14.4, 6.8 Hz, 1H), 3.30 (s, 3H), 3.13 (s, 3H), 3.08 (s, 3H), 3.86 (A' of A'B'X', dd, J=13.2, 4.0 Hz, 1H), 2.76 (B' of A'B'X', dd, J=13.2, 7.6 Hz, 1H), 1.02 (d, J=6.0 Hz, 3H), 0.80-0.65 (m, 2H), 0.46-0.39 (m, 1H), 0.25-0.18 (m, 1H).

Intermediate G: N-(tert-butoxycarbonyl)-N-(2-oxo-2-{2-{methyl[(2-methylcyclopropyl)methyl]amino}-6-[methyl(methylsulfonyl)amino]pyridin-4-yl}ethyl)-α-D-methylphenylalaninamide (Scheme 14)

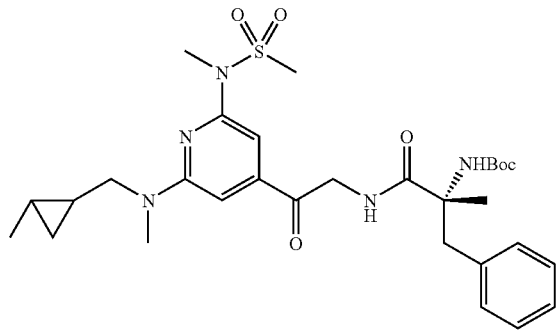

Step A: Coupling

A solution of Intermediate F (330 mg, 096 mmol), N-Boc-D-alpha-methyl phenylalanine (323 mg, 1.16 mmol), EDC (240 mg, 1.25 mmol), HOAt (157 mg, 1.16 mmol) and diisopropylethyl amine (0.34 mL, 1.93 mmol) in DMF (9 mL) was stirred at it for 16 h. The reaction mixture was diluted with EtOAc, washed with water and brine, dried over sodium sulfate, concentrated in vacuo and purified by flash chromatography (silica, 30-65% EtOAc/hexanes) to provide N-(tert-butoxycarbonyl)-N -(2-hydroxy-2-{2-{methyl[(2-methylcyclopropyl)methyl]amino}-6-[methyl(methylsulfonyl)amino]pyridin-4-yl}ethyl)-D-α-methylphenylalaninamide as a pale yellow foam, which was carried directly into the oxidation step.

Step B: Oxidation

To a solution of N-(tert-butoxycarbonyl)-N-(2-hydroxy-2-{2-{methyl[(2-methylcyclopropyl)methyl]amino}-6-[methyl(methylsulfonyl)amino]pyridin-4-yl}ethyl)-D-α-methylphenylalaninamide (458 mg, 0.76 mmol) in DCM (6 mL) and DMSO (1.5 mL) was added triethyl amine (0.53 mL, 3.79 mmol) and sulfurtrioxide-pyridine (483 mg, 3.03 mmol). The reaction mixture was stirred at rt for 1.5 h, diluted with EtOAc, washed with 10% KHSO$_4$, saturated NaHCO$_3$ and brine, dried over sodium sulfate, concentrated in vacuo and purified by flash chromatography (silica, 0-50% EtOAc/hexanes) to provide N-(tert-butoxycarbonyl)-N-(2-oxo-2-{2-{methyl[(2-methylcyclopropyl)methyl]amino}-6-[methyl(methylsulfonyl)amino]pyridin-4-yl}ethyl)-D-α-methylphenylalaninamide as an orange oil. $^1$H NMR (400

MHz, CDCl₃) δ 7.38-7.10 (m, 5H), 6.91 (s, 1H), 6.75 (s, 1H), 4.82 (br s, 1H), 4.78-4.62 (m, 2H), 3.53 (A of ABX, dd, J=14.7, 6.7 Hz, 1H), 3.43 (A of AB, d, J=14.4 Hz, 1H), 3.38 (s, 3H), 3.36 (B of ABX, dd, J=14.7, 6.6 Hz, 1H), 3.16 (s, 3H), 3.15 (B of AB, d, J=14.4 Hz, 1H), 3.13 (s, 3H), 1.49 (s, 9H), 1.46 (s, 3H), 1.04 (d, J=6.0 Hz, 3H), 0.80-0.62 (m, 2H), 0.46-0.38 (m, 1H), 0.31-0.24 (m, 1H).

Intermediate H: tert-butyl [1R-benzyl-1-methyl-3-({2-{methyl[(2-methylcyclopropyl)methyl]amino}-6-[methyethethylsulfonyl)amino]isonicotinoyl}amino)-2-oxopropyl]carbamate (Scheme 17)

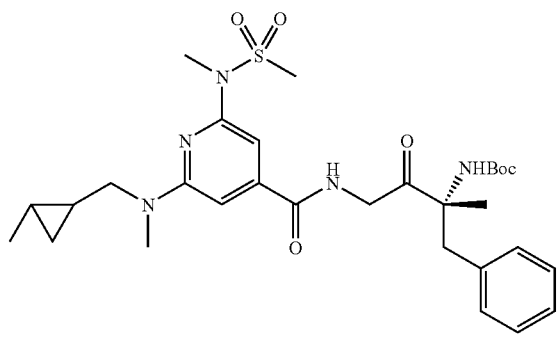

tert-butyl [1R-benzyl-1-methyl-3-({2-{methyl[(2-methylcyclopropyl)methyl]amino}-6-[methyl(methylsulfonyl)amino]isonicotinoyl}amino)-2-oxopropyl]carbamate was prepared by the coupling of Intermediate III and Intermediate D) and ensuing hydroxyl oxidation using the same procedure as described for the preparation of N-(tert-butoxycarbonyl)-N-(2-oxo-2-{2-{methyl[(2-methylcyclopropyl)methyl]amino}-6-[methyl(methylsulfonyl)amino]pyridin-4-yl}ethyl)-D-α-methylphenylalaninamide (intermediate G). ¹H NMR (400 MHz, CDCl₃) δ 7.36-7.22 (m, 3H), 7.13-7.08 (m, 2H), 6.88 (br s, 1H), 6.79 (s, 1H), 6.72 (s, 1H), 4.74 (br s, 1H), 4.68-4.58 (m, 1H), 4.44-4.34 (m, 1H), 3.53 (A of ABX, dd, J=14.0, 6.0 Hz, 1H), 3.38 (s, 3H), 3.40-3.30 (A of AB and B of ABX, m, 2H), 3.14 (s, 3H), 3.11 (s, 3H), 3.05 (B of AB, d, J=13.6 Hz, 1H), 1.49 (s, 9H), 1.32 (s, 3H), 1.04 (d, J=6.0 Hz, 3H), 0.78-0.62 (m, 2H), 0.44-0.36 (m, 1H), 0.29-0.22 (m, 1H).

Intermediate J: ethyl 2-{methyl[(2-methylcyclopropyl)methyl]amino}-6-[methyl(methylsulfonyl)amino]pyridine-4-carboximidoate (Scheme 7, 11)

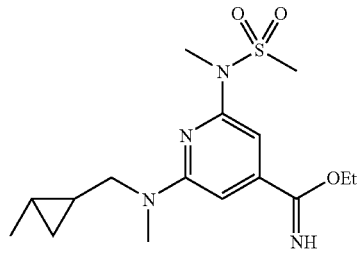

Step A: Nitrile Preparation (Scheme 7)

A suspension of Intermediate D (250 mg, 0.76 mmol), ammonium chloride (204 mg, 3.82 mmol), EDC (176 mg, 0.92 mmol), HOAt (104 mg, 0.76 mmol) and diisopropylethyl amine (0.67 mL, 3.82 mmol) in DMF (10 mL) was stirred at rt for 16 h. The reaction mixture was diluted with EtOAc, washed with water, 10% KHSO₄, saturated aq NaHCO₃, aq LiCl, dried over sodium sulfate and concentrated in vacuo. The residue was taken in THF (5 mL), treated with Burgess reagent (219 mg, 0.92 mmol) and irradiated under microwave (Smith Synthesizer) at 80° C. for 5 min, concentrated in vacuo and purified by flash chromatography (silica, 0-30% EtOAc/hexanes) to provide N-(4-cyano-6-{methyl[(2-methylcyclopropyl)methyl]amino}pyridin-2-yl)-N-methylmethanesulfonamide. ¹H NMR (400 MHz, CDCl₃) δ 6.73 (s, 1H), 6.48 (s, 1H), 3.47 (A of ABX, dd, J=14.8, 6.4 Hz, 1H), 3.37 (s, 3H), 3.33 (B of ABX, dd, J=14.8, 6.8 Hz, 1H), 3.13 (s, 3H), 3.09 (s, 3H), 1.04 (d, J=5.6 Hz, 3H), 0.78-0.62 (m, 2H), 0.45-0.37 (m, 1H), 0.32-0.25 (m, 1H).

Step B: Imidate Preparation

Through a solution of N-(4-cyano-6-{methyl[(2-methylcyclopropyl)methyl]amino}pyridin-2-yl)-N-methylmethanesulfonamide (180 mg, 0.58 mmol) in EtOH (10 mL) cooled to 0° C., was bubbled HCl(g) for 10 min. The reaction mixture was sealed, allowed to warm to rt and stirred for 3 h. Nitrogen was bubbled through the reaction mixture for 10 min and the reaction mixture was concentrated in vacuo. Trituration with diethyl ether provided ethyl 2-{methyl[(2-methylcyclopropyl)methyl]amino}-6-[methyl(methylsulfonyl)amino]pyridine-4-carboximidoate as the hydrochloride and bright yellow solid. ¹H NMR (400 MHz, CD₃OD) δ 6.96 (s, 1H), 6.88 (s, 1H), 4.63 (q, J=7.2 Hz, 2H), 3.60 (A of ABX, dd, J=14.8, 6.4 Hz, 1H), 3.44 (B of ABX, dd, J=14.8, 6.8 Hz, 1H), 3.38 (s, 3H), 3.18 (s, 3H), 3.16 (s, 3H), 1.61 (t, J=7.2 Hz, 3H), 1.03 (d, J=6.0 Hz, 3H), 0.84-0.68 (m, 2H), 0.50-0.43 (m, 1H), 0.29-0.23 (m, 1H).

Intermediate K: (2,2-difluoroethyl)[(2-methylcyclopropyl)methyl]amine

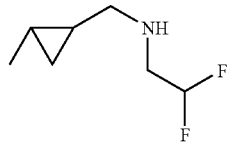

Step A: Coupling

In a 500-mL flask difluoroacetic acid (0.78 g, 8.2 mmol), N-benzyl-1-(2-trans-methylcyclopropyl)methanamine (1.3 g, 7.42 mmol) and DIPEA (4.2 g, 32.6 mmol) were dissolved in 100 mL of dichloromethane. To this solution at rt BOP (3.3 g, 7.42 mmol) was added as a solid portionwise and stirred one hour. The reaction was concentrated in vacuo and purified by flash column chromatography (silica, 0-10% ethyl acetate/hexanes) to provide 1.45 g (77%) of amide as a clear oil: ¹H NMR (400 MHz, CDCl₃) δ 7.31 (m, 5H), 6.19 (td, J=51, 20 Hz, 1H), 4.75 (m, 2H), 3.24 (m, 2H), 0.99 (t, J=5.5 Hz, 3H), 0.62 (m, 2H), 0.31 (m, 2H); LCMS [M+H]⁺=254.1.

Step B: Reduction

In a round-bottom flask N-benzyl-2,2-difluoro-N-{[-2-methylcyclopropylmethyl]-methyl}acetamide (1.45 g, 5.7 mmol) was dissolved in 75 mL anhydrous THF. To this solution was added BH₃-THF (18.9 mmol, 18.9 mL of a 1M solution in THF). The reaction was equipped with a reflux condenser and heated to reflux for 16 hours. The reaction was cooled to 0° C. and quenched with methanol followed by concentrated HCl (5 mL). The resulting mixture was stirred at ambient temperature for 16 hours. The crude mixture was then concentrated in vacuo and partitioned between 10% NaOH/ethyl acetate. The organics were dried over sodium sulfate, filtered and evaporated in vacuo. Purification by flash column chromatography (silica, 0-10% ethyl acetate/hexanes) gave 1.25 g (91%) of the amine as a clear oil: $^1$H NMR (400 MHz, CDCl$^3$) δ 7.31 (m, 5H), 5.75 (tt, 56.5, 4.5 Hz, 1H), 3.78 (d, J=13.7 Hz, 1H), 3.73 (d, J=13.7 Hz, 1H), 2.92 (td, J=15, 3.8 Hz, 2H), 2.56 (dd, J=13.2, 6.0 Hz, 1H), 2.37 (dd, J=13.2 Hz, 7.0 Hz, 1H), 1.03 (d, J=6.0 Hz, 3H), 0.54 (m, 2H), 0.25 (t, J=6.2 Hz, 2H); LCMS [M+H]$^+$=240.2.

Step C: Hydrogenation

A solution of N-benzyl-2,2-difluoro-N-[(2-methylcyclopropyl)methyl]ethanamine (1.25 g, 5.2 mmol) and hydrochloric acid (5.7 mmol, 1.44 mL of a 4M solution in dioxane) in ethanol (50 mL) was degassed with nitrogen and treated with palladium hydroxide (125 mg). The reaction was placed under a hydrogen atmosphere and stirred vigorously for 1 hour. The reaction was filtered through celite, washed with methanol and concentrated in vacuo to give (2,2-difluoroethyl)[(2-methylcyclopropyl)methyl]amine as a pale yellow oil: $^1$H NMR (400 MHz, CD$_3$OD) δ 6.35 (tt, 48, 3 Hz, 1H), 3.56 (td, J=15.6, 3.1 Hz, 2H), 3.03 (m, 2H), 1.11 (d, J=5.9 Hz, 3H), 0.83 (m, 2H), 0.60 (m, 1H), 0.50 (m, 1H).

Intermediate L: N,N-dimethyl-N'-[(2-methylcyclopropyl)methyl]propane-1,3-diamine

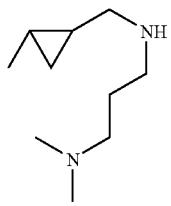

Step A: Coupling

In a 100-mL flask acrylic acid (0.17 g, 2.4 mmol), N-benzyl-1-(2-trans-methylcyclopropyl)methanamine (0.5 g, 2.4 mmol) and DIPEA (0.64 g, 4.9 mmol) were dissolved in 20 mL of dichloromethane. To this solution at rt EDC (0.68 g, 3.5 mmol) was added as a solid portionwise and stirred 15 hours. The reaction was partitioned between 1M HCl and methylene chloride. The organics were dried over sodium sulfate, filtered, concentrated in vacuo and carried into next reaction crude.

Step B: Michael Addition

In a 50-mL flask acrylamide (crude from step A) in methanol (10 mL) was treated with dimethylamine (4.5 mmol, 2.2 mL of a 2M solution in methanol). The reaction was stirred for 1 hour at ambient temperature then concentrated in vacuo. The residue was purified by flash column chromatography (2.5-15% MeOH/methylene chloride) to provide 0.47 g (75% 2-steps) of N$^1$-benzyl-N$^3$,N$^3$-dimethyl-N'-[(2-methylcyclopropyl)-methyl]-β-alaninamide as a clear oil: $^1$H NMR (400 MHz, CDCl$_3$) δ 7.24 (m, 5H), 4.68 (m, 2H), 3.21 (m, 2H), 2.67 (m, 4H), 2.34 (s, 3H), 2.24 (s, 3H), 0.97 (m, 3H), 0.58 (m, 2H), 0.29 m, 2H). LCMS [M+H]$^+$=275.4.

Step C: Reduction

In a round-bottom flask N$^1$-benzyl-N$^3$,N$^3$-dimethyl-N'-[(2-methylcyclopropyl)-methyl]-β-alaninamide (0.47 g, 1.7 mmol) was dissolved in 10 mL anhydrous THF. To this solution was added BH$_3$-THF (5.1 mmol, 5.1 mL of a 1M solution in THF). The reaction was equipped with a reflux condenser and heated to reflux for 16 hours. The reaction was cooled to 0° C. and quenched with methanol followed by concentrated HCl (5 mL). The resulting mixture was heated to reflux for 16 hours. The crude mixture was then concentrated in vacuo and partitioned between 10% NaOH/ethyl acetate. The organics were dried over sodium sulfate, filtered and evaporated in vacuo. Purification by reverse phase chromatography gave 0.42 g (49%) of N$^1$-benzyl-N$^3$,N$^3$dimethyl-N'-[(2-methylcyclopropyl)methyl]propane-1,3-diaminium bis(trifluoroacetate) as a clear oil: LCMS [M+H]$^+$=261.5.

Step D: Hydrogenation

A solution of N$^1$-benzyl-N$^3$,N$^3$-dimethyl-N$^1$-[(2-methylcyclopropyl)methyl]propane-1,3-diaminium bis(trifluoroacetate) (0.42 g, 0.86 mmol) in ethanol (50 mL) was degassed with nitrogen and treated with palladium hydroxide (75 mg). The reaction was placed under a hydrogen atmosphere and stirred vigorously for 1 hour. The reaction was filtered through celite, washed with methanol and concentrated in vacuo to give N,N-dimethyl-N'-[(2-methylcyclopropyl)methyl]propane-1,3-diaminium bis(trifluoroacetate) as a pale yellow oil.

Intermediate M: (2-fluoroethyl)[(2-methylcyclopropyl)methyl]amine

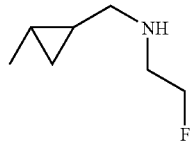

Prepared from fluoroacetic acid using a similar procedure as described in Intermediate K. $^1$H NMR (400 MHz, CDCl$_3$) δ 9.79 (bs, 1H), 4.98 (bd, J=46.3, 2H), 3.42 (m, 2H), 3.03 (bs, 2H), 1.12 (bs, 3H), 1.01 (bs, 1H), 0.87 (bs, 1H), 0.66 (bs, 1H), 0.50 (bs, 1H).

Intermediate N: (2-methoxyethyl)[(2-methylcyclopropyl)methyl]amine

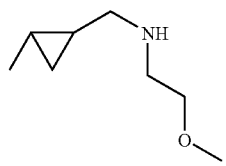

Prepared from methoxyacetic acid using a similar procedure as described in Intermediate K. $^1$H NMR (400 MHz, CDCl$_3$) δ 7.98 (bs, 1H), 3.64 (bs, 2H), 3.38 (bs, 3H), 3.27 (bs, 2H), 3.00 (bs, 2H), 1.06 (d, J=5.3 Hz, 3H), 0.79 (bs, 2H), 0.51 (m, 2H).

Intermediate O: N,N-dimethyl-N'-[(2-methylcyclopropyl)methyl]ethane-1,2-diamine

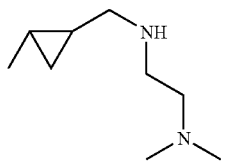

Prepared from N,N-dimethylglycine using a similar procedure as described in Intermediate K. $^1$H NMR (400 MHz, CD$_3$OD) δ 3.49 (m, 4H), 2.98 (m, 2H), 2.96 (s, 6H), 1.09 (d, J=5.8 Hz, 3H), 0.83 (m, 2H), 0.61 (m, 1H), 0.49 (m, 1H).

Intermediate P: {(1S)-[(1S,2S)-2-methylcyclopropyl]ethyl}amine

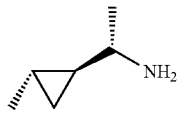

Step A. (2E)-1,1-diethoxybut-2-ene

Crotonaldehyde (23.64 mL, 285.35 mmol), triethyl orthoformate (57.02 mL, 342.42 mmol) and ammonium nitrate (2.28 g, 28.54 mmol) were combined in 60 mL EtOH. After 22 h at ambient temperature, the reaction was diluted with EtOAc (60 mL) and washed with saturated sodium bicarbonate solution (40 mL). The aqueous layer was back extracted with EtOAc (20 mL). The combined organics were washed with brine (40 mL), dried over Na$_2$SO$_4$, filtered and concentrated in vacuo to give 36.5 g (89%) of 1,1-diethoxybut-2-ene. $^1$H NMR (CDCl$_3$, 400 MHz) 5.84 (m, 1H); 5.54 (m, 1H); 4.82 (d, J=5.7 Hz, 1H); 3.64 (m, 2H); 3.49 (m, 2H); 1.73 (m, 3H); 1.21 (m, 6H).

Step B. diisopropyl (4S,5S)-2-[(1E)-prop-1-enyl]-1,3-dioxolane-4,5-dicarboxylate A solution of (2E)-1,1-diethoxybut-2-ene (32.20 g, 223.27 mmol), (−)-diisopropyl D-tartrate (64.64 mL, 245.60 mmol) and pyridinium tosylate (2.24 g, 8.93 mmol) in 100 mL benzene was heated to 95° C. to distill off the solvent and EtOH produced. After 7 h at 95° C., the reaction was cooled to rt and concentrated in vacuo. Purification by normal phase chromatography (10->30% EtOAc/hexanes) yielded 35.37 g (55%) of diisopropyl (4S,5S)-2-[(1E)-prop-1-enyl]-1,3-dioxolane-4,5-dicarboxylate as an orange oil. $^1$H NMR (CDCl$_3$, 400 MHz) 6.03 (m, 1H); 5.86 (m, 2H); 5.12 (m, 2H); 4.71 (d, J=3.84 Hz, 1H); 4.63 (d, J=3.84 Hz, 1H); 1.78 (m, 3H); 1.30 (d, J=6.23 Hz, 12H); LC/MS [M+H]$^+$=287.

Step C. diisopropyl (4S,5S)-2-[(1S,2S)-2-methylcyclopropyl]-1,3-dioxolane-4,5-dicarboxylate To a −20° C. solution of intermediate diisopropyl (4S,5S)-2-[(1E)-prop-1-enyl]-1,3-dioxolane-4,5-dicarboxylate (4.10 g, 14.32 mmol) in 60 mL hexanes was added 1M diethylzinc in hexanes (42.96 mL, 42.96 mmol). Diiodomethane (6.92 mL, 85.92 mmol) was added dropwise with vigorous stirring. After 1 h at −20° C., the reaction was refrigerated at −5° C. After 17 h at −5° C., the reaction was stirred at 0° C. for an additional 5 h and then quenched with cold saturated ammonium chloride solution (100 mL) and extracted with Et$_2$O (100 mL×3). The combined organics were washed w/aqueous sodium thiosulfate (100 mL) and brine (100 mL), filtered, dried over Na$_2$SO$_4$, filtered again and concentrated in vacuo. Purification by normal phase chromatography (10->30% EtOAc/hexanes) yielded 3.85 g (89%) of diisopropyl (4S,5S)-2-[(1S,2S)-2-methylcyclopropyl]-1,3-dioxolane-4,5-dicarboxylate as a yellow oil. 1H NMR (CDCl$_3$, 400 MHz) 5.12 (m, 2H); 4.78 (d, J=6.41 Hz, 1H); 4.66 (d, J=4.21 Hz, 1H); 4.57 (d, J=4.22 Hz, 1H); 1.30 (m, 12H); 1.09 (d, J=5.68 Hz, 3H); 0.94 (m, 2H); 0.67 (m, 1H); 0.39 (m, 1H); LC/MS [M+H]$^+$=301.

Step D. 2-methyl-N-{(1E)-[(1S,2S)-2-methylcyclopropyl]methylidene}propane-2-sulfinamide To a solution of diisopropyl (4S,5S)-2-[(1S,2S)-2-methylcyclopropyl]-1,3-dioxolane-4,5-dicarboxylate (0.450 g, 1.50 mmol) in 5 mL CH$_2$Cl$_2$/200 uL H$_2$O was added p-toluenesulfonic acid (0.071 g, 0.38 mmol). Reaction heated to reflux at 50° C. After 16 h at 50° C., the reaction was cooled to rt. Water droplets sitting at the top of the reaction were removed. Copper (II) sulfate (0.507 g, 2.85 mmol) and R-(+)-tert-butanesulfinamide (0.173 g, 1.43 mmol) were added. After 5.5 h at ambient temperature, the reaction was filtered over a pad of celite. The celite was washed with CH$_2$Cl$_2$ (200 mL) and the filtrate concentrated in vacuo. Purification by normal phase chromatography (0->50% EtOAc/hexanes) yielded 0.245 g (92%) of 2-methyl-N-{(1E)-[(1S,2S)-2-methylcyclopropyl]methylidene}propane-2-sulfinamide as a clear, colorless residue. $^1$H NMR (CDCl$_3$, 400 MHz) 7.46 (d, J=7.69 Hz, 1H); 1.62 (m, 1H); 1.25 (m, 2H); 1.10 (m, 12H); 0.82 (m, 1H); LC/MS [M+H]$^+$=188.

Step E. 2-methyl-N-{(1S)-1-[(1S,2S)-2-methylcyclopropyl]ethyl}propane-2-sulfinamide To a −78° C. solution of 2-methyl-N-{(1E)-[(1S,2S)-2-methylcyclopropyl]methylidene}propane-2-sulfinamide (0.300 g, 1.60 mmol) in 5 mL CH$_2$Cl$_2$ was added 3M methylmagnesium bromide in Et$_2$O (1.07 mL, 3.20 mmol). After 2 h at −78° C., the reaction was warmed to rt. After 1 h at ambient temperature, the reaction was quenched with saturated ammonium chloride solution (15 mL) and extracted with EtOAc (30 mL×2). The combined organics were washed with brine (15 mL), dried over Na$_2$SO$_4$, filtered and concentrated in vacuo. Purification by normal phase chromatography (0->80% EtOAc/hexanes) yielded 0.224 g (69%) of -methyl-N-{(1S)-1-[(1S,2S)-2-methylcyclopropyl]ethyl}propane-2-sulfinamide as a clear, colorless residue. 1H NMR (CDCl$_3$, 400 MHz) 2.77 (m, 1H); 1.31 (d, J=6.50 Hz, 3H); 1.21 (s, 9H); 1.03 (d, J=5.77 Hz, 3H); 0.54 (m, 3H); 0.30 (m, 1H); LC/MS [M+H]$^+$=204.

Step F. (1S)-1-[(1S,2S)-2-methylcyclopropyl]ethanaminium chloride

To a 0° C. solution of 2-methyl-N-{(1S)-1-[(1S,2S)-2-methylcyclopropyl]ethyl}propane-2-sulfinamide (0.210 g, 1.03 mmol) in 4 mL MeOH was added 2M HCl in Et$_2$O (0.52 mL, 1.03 mmol). Reaction stirred from 0° C. to rt over 18 h and then concentrated in vacuo. The resulting material was taken up in Et$_2$O (4 mL) and concentrated in vacuo twice to give (1S)-1-[(1S,2S)-2-methylcyclopropyl]ethanaminium chloride as a white solid. $^1$H NMR (CDCl$_3$, 400 MHz) 2.60 (m, 1H); 1.37 (d, J=6.59 Hz, 3H); 1.08 (d, J=6.04 Hz, 3H); 0.77 (m, 1H); 0.64 (m, 2H); 0.42 (m, 1H); LC/MS [M+H]$^+$=100.

Intermediate Q: {(1R)-1-[(1S,2S)-2-methylcyclopropyl]ethyl}amine

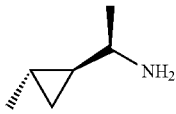

Prepared using protocol as described for intermediate P, with the modification of S-(+)-tert-butanesulfinamide being used in step D. LC/MS [M+H]⁺=100.

Intermediate R: {(1S)-1-[(1S,2S)-2-methylcyclopropyl]propyl}amine

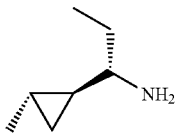

Prepared using protocol as described for intermediate P, with the modification of ethylmagnesium bromide being used in step E. LC/MS [M+H]⁺=114.

Intermediate S: (1S)-2-methyl-1-[(1S,2S)-2-methylcyclopropyl]propan-1-amine

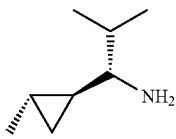

Prepared using protocol as described for intermediate P, with the modification of isopropylmagnesium bromide being used in step E. LC/MS [M+H]⁺=128.

Intermediate T: (2-{[tert-butyl(dimethyl)silyl]oxy}ethyl)[(2-methylcyclopropyl)-methyl]amine

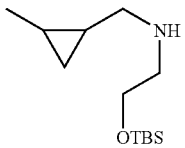

Prepared from (tert-butyl(dimethyl)silyloxy)ethyl amine using a similar procedure as described for Intermediate B. ¹H NMR (400 MHz, CD₃OD) δ 3.74 (t, J=5.3 Hz, 2H), 2.76 (m, 2H), 2.52 (m, 2H), 1.04 (d, J=6.0 Hz, 3H), 0.90 (s, 9H), 0.68 (m, 1H), 0.55 (m, 1H), 0.29 (m, 1H), 0.24 (m, 1H), 0.07 (s, 6H).

Intermediate a: 2-{(2,2-difluoroethyl)[(2-methylcyclopropyl)methyl]amino}-6-[methyl(methylsulfonyl)amino]isonicotic acid

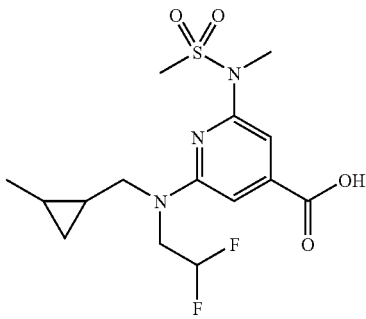

Prepared from Intermediate K using a similar procedure as described in Intermediate C. LCMS [M+H]⁺=378.3.

Intermediate b: 2-{(2-methoxyethyl)[(2-methylcyclopropyl)methyl]amino}-6-[methyl(methylsulfonyl)amino]isonicotic acid

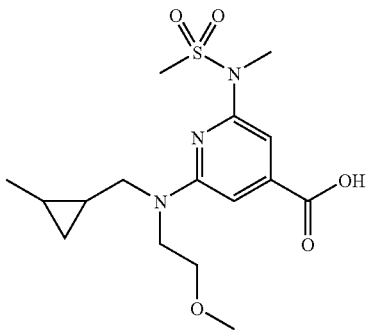

Prepared from Intermediate N using a similar procedure as described in Intermediate C. LCMS [M+H]⁺=372.3.

Intermediate c: 2-{(2,2-difluoroethyl)[(2-methylcyclopropyl)methyl]amino}-6-[(isopropylsulfonyl)(methyl)amino]isonicotinic acid

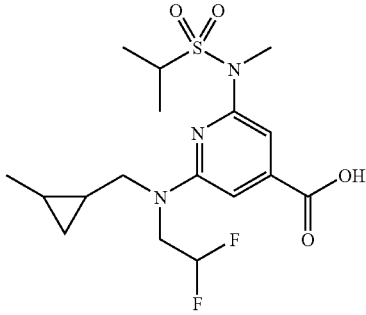

Prepared from Intermediate K and (isopropylsulfonyl)methylamine using a similar procedure as described in Intermediate C. ¹H NMR (400 MHz, CDCl₃) δ 7.09 (s, 1H), 7.01 (s, 1H), 6.08 (td, J=56.4, 4.2 Hz, 1H), 3.93 (m, 2H), 3.46 (m, 1H), 3.44 (s, 3H), 3.32 (dd, J=15.0, 6.6 Hz, 1H), 1.41 (d, J=6.8 Hz, 6H), 1.06 (d, J=5.7 Hz, 3H), 0.74 (m, 2H), 0.45 (m, 1H), 0.35 (m, 1H). LCMS [M+H]⁺=406.5.

Intermediate d: 2-{(2-fluoroethyl)[(2-methylcyclopropyl)methyl]amino}-6-[(isopropylsulfonyl)(methyl)amino]isonicotic acid

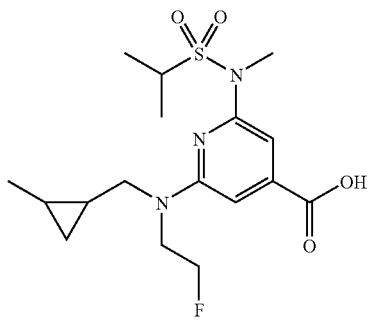

Prepared from Intermediate M and (isopropylsulfonyl)methylamine using a similar procedure as described in Intermediate C. LCMS [M+H]⁺=388.0.

Intermediate e: 2-[(isopropylsulfonyl)(methyl)amino]-6-{(2-methoxyethyl)[(2-methylcyclopropyl)methyl]amino}isonicotinic acid

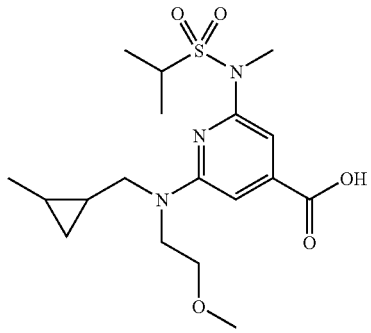

Prepared from Intermediate N and (isopropylsulfonyl)methylamine using a similar procedure as described in Intermediate C. $^1$H NMR (400 MHz, CDCl$_3$) δ 7.01 (s, 1H), 6.98 (s, 1H), 3.99 (m, 1H), 3.75 (m, 1H), 3.59 (m, 1H), 3.47 (m, 1H), 3.44 (s, 3H), 3.36 (s, 3H), 3.34 (m, 1H), 1.40 (d, J=3.3 Hz, 6H), 1.05 (d, J=5.8 Hz, 3H), 0.74 (m, 2H), 0.43 (m, 1H), 0.29 (m, 1H). LCMS [M+H]⁺=400.5.

Intermediate f: 2-{[2-(dimethylamino)ethyl][(2-methylcyclopropyl)methyl]amino}-6-[(isopropylsulfonyl)(methyl)amino]isonicotinic acid

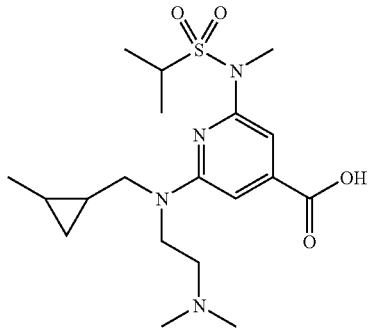

Prepared from Intermediate O and (isopropylsulfonyl)methylamine using a similar procedure as described in Intermediate C. $^1$H NMR (400 MHz, CDCl$_3$) δ 6.95 (s, 1H), 6.85 (s, 1H), 4.00 (m, 2H), 3.88 (m, 1H), 3.44 (m, 2H), 3.43 (s, 3H), 3.34 (d, J=5.9 Hz, 2H), 2.95 (bs, 6H), 1.38 (d, J=7.0 Hz, 6H), 1.03 (d, J=5.7 Hz, 3H), 0.70 (m, 2H), 0.45 (m, 1H), 0.31 (m, 1H). LCMS [M+H]⁺=413.3.

Intermediate g: 2-{[3-(dimethylamino)propyl][(2-methylcyclopropyl)methyl]amino}-6-[(isopropylsulfonyl)(methyl)amino]isonicotinic acid

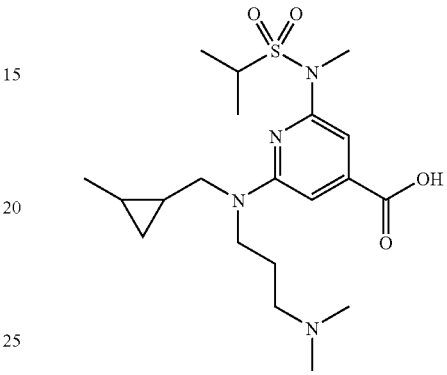

Prepared from Intermediate L and (isopropylsulfonyl)methylamine using a similar procedure as described in Intermediate C. LCMS [M+H]⁺=427.4.

Intermediate h: tert-butyl [1-(5-{2-chloro-6-[methyl(methylsulfonyl)amino]pyridin-4-yl}-1,3,4-oxadiazol-2-yl)-1R-methyl-2-phenylethyl]carbamate (Scheme 8)

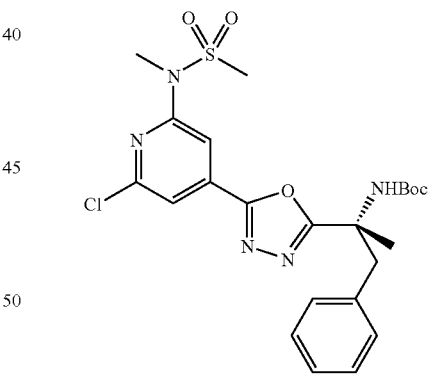

Step A. Coupling

To a solution of 2-chloro-6-[methyl(methylsulfonyl)amino)isonicotinic acid (0.200 g, 0.76 mmol) in 3 mL DMF was added triethylamine (0.13 mL, 0.91 mmol), intermediate I (0.222 g, 0.76 mmol), HOAt (0.123 g, 0.91 mmol) and EDC (0.174 g, 0.91 mmol). After 17 h at ambient temperature, the reaction was diluted with EtOAc (60 mL), washed with saturated sodium bicarbonate solution (30 mL) and brine (30 mL), dried over Na$_2$SO$_4$, filtered and concentrated in vacuo. Purification by normal phase chromatography (20->80% EtOAc/hexanes) yielded 0.544 g (99%) of acyl hydrazide as a clear, colorless residue. NMR (CDCl$_3$, 400 MHz) 7.71 (s, 1H); 7.53 (s, 1H); 7.29 (m, 3H); 7.15 (d, J=6.59 Hz, 2H); 3.50

(d, J=13.55 Hz, 1H); 3.42 (s, 3H); 3.11 (s, 3H); 3.05 (d, J=13.73 Hz, 1H); 1.47 (s, 9H); 1.43 (s, 3H); LC/MS [M−C$_4$H$_7$]$^+$=484.

Step B. Cyclodehydration

To a solution of acyl hydrazide from step A (0.550 g, 1.02 mmol) in 5 mL DCE was added Burgess reagent (0.971 g, 4.07 mmol). Reaction microwaved at 120° C. for 10 min and directly purified by normal phase chromatography (0->50% EtOAc/hexanes) to yield tert-butyl (1R)-1-(5-{2-chloro-6-[methyl(methylsulfonyl)amino]pyridin-4-yl}-1,3,4-oxadiazol-2-yl)-1-methyl-2-phenylethylcarbamate as a white foam. NMR (CDCl$_3$, 400 MHz) 7.89 (s, 1H); 7.72 (s, 1H); 7.29 (m, 3H); 7.08 (m, 2H); 3.60 (d, J=13.55 Hz, 1H); 3.46 (s, 3H); 3.38 (d, J=13.55 Hz, 1H); 3.15 (s, 3H); 3.15 (s, 3H); 1.70 (s, 3H); 1.42 (s, 9H); [M+H]$^+$=522.

Intermediate i. tert-butyl{1-[5-(2-chloro-6-{methyl[(2-methylcyclopropyl)methyl]amino}pyridin-4-yl)-1,3,4-oxadiazol-2-yl]-1R-methyl-2-phenylethyl}carbamate

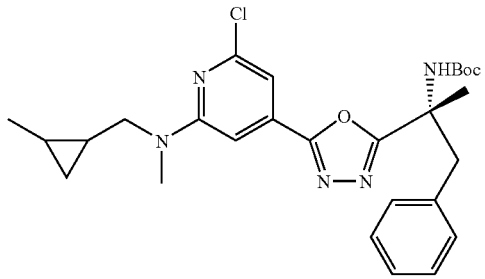

Step A: Nucleophilic Amination

A solution of 2,6-dichloroisonicotinic acid (0.25 g, 1.3 mmol), methyl-[(methylcyclopropyl)methyl]amine hydrochloride (0.53 g, 3.9 mmol) and cesium carbonate (1.25 g, 6.5 mmol) in 5 mL DMF was heated to 120° C. in a sealed tube for 72 hr. The reaction was partitioned between 1M HCl and ethyl acetate. The organics were washed with water (4×), brine, dried over sodium sulfate, filtered and evaporated in vacuo to give 0.3 g (90%) of crude 2-chloro-6-{methyl[(2-methylcyclopropyl)methyl]amino}isonicotinic acid as a brown oil: LCMS (M+H)=255.0.

Step B: Coupling

A solution of 2-chloro-6-{methyl[(2-methylcyclopropyl)methyl]amino}isonicotinic acid (0.33 g, 1.3 mmol), N-(tert-butoxycarbonyl)-D-α-methylphenylalaninhydrazamide (0.38 g, 1.3 mmol) and diisopropylethylamine (0.17 g, 1.3 mmol) in 10 mL methylene chloride was treated with BOP (0.57 g, 1.3 mmol). Upon stirring at ambient temperature for one hour the reaction was treated with additional hydrazamide (0.19 g, 0.65 mmol) and BOP (0.29 g, 0.65 mmol). After one hour, the reaction was evaporated in vacuo and purified by reverse phase LC to give 0.224 g (33%) of tert-butyl{1-benzyl-2-oxo-2-[2-(2-chloro-6-{methyl[(2-methylcyclopropyl)methyl]amino}isonicotinoyl)hydrazino]-1R-methylethyl}carbamate as an orange solid: LCMS (M+H)=530.3.

Step C: Cyclodehydration

A solution of tert-butyl{1-benzyl-2-oxo-2-[2-(2-chloro-6-{methyl[(2-methylcyclopropyl)methyl]amino} isonicotinoyl)hydrazino]-1R-methylethyl}carbamate (0.22 g, 0.42 mmol) in 2 mL THF was treated with Burgess reagent (0.22 g, 0.93 mmol). The reaction was sealed and heated to 130° C. in the microwave reactor for 5 min. An additional 2 equivalents of Burgess reagent was added and the vessel re-sealed and re-heated for 5 min. The reaction was evaporated in vacuo and purified by flash column chromatography (25-40% ethyl acetate:hexanes) to give tert-butyl{1-[5-(2-chloro-6-{methyl[(2-methylcyclopropyl)methyl]amino}pyridin-4-yl)-1,3,4-oxadiazol-2-yl]-1R-methyl-2-phenylethyl}carbamate as a yellow oil: $^1$H NMR (400 MHz, CDCl$_3$) δ 7.28 (m, 3H), 7.06 (m, 2H), 7.00 (s, 2H), 3.57 (m, 2H), 3.39 (m, 2H), 3.15 (s, 3H), 1.73 (s, 3H), 1.56 (s, 9H), 1.05 (d, J=5.7 Hz, 3H), 0.72 (m, 2H), 0.45 (m, 1H), 0.29 (m, 1H). LCMS (M+H)=512.2.

Intermediate k: tert-butyl [1-(2-{2-chloro-6-[methyl(methylsulfonyl)amino]pyridin-4-yl}-1,3-oxazol-5-yl)-1R-methyl-2-phenylethyl]carbamate

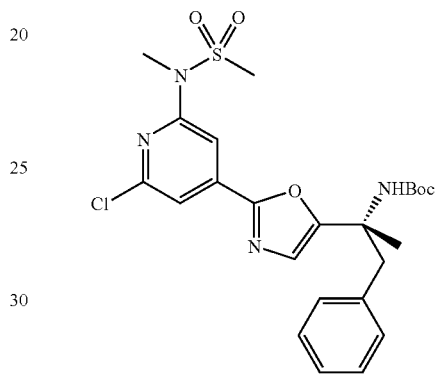

Step A. coupling

To a solution of 2-chloro-6-[methyl(methysulfonyl)amino]isonicotinic acid (1.80 g, 6.79 mmol) in 10 mL DMF was added triethylamine (1.14 mL, 8.15 mmol), intermediate IV (2.00 g, 8.15 mmol), HOAt (1.11 g, 8.15 mmol) and EDC (1.56 g, 8.15 mmol). After 3.5 h at ambient temperature, the reaction was diluted w/EtOAc (100 mL), washed with saturated sodium bicarbonate solution (50 mL) and brine (50 mL), dried over Na$_2$SO$_4$, filtered and concentrated in vacuo. Purification by normal phase chromatography (0->70% EtOAc/hexanes and 0-7% MeOH/CH$_2$Cl$_2$) yielded 3.18 g (87%) of tert-butyl (1R)-1-benzyl-3-({2-chloro-6-[methyl(methylsulfonyl)amino]isonicotinoyl}amino)-2-hydroxy-1-methylpropylcarbamate as a white solid. NMR (CDCl$_3$, 400 MHz) 7.66 (d, J=2.58 Hz, 1H); 7.50 (d, J=4.58 Hz, 1H); 7.31 (m, 3H); 7.18 (m, 2H); 4.05 (m, 1H); 3.84 (m, 1H); 3.59 (m, 1H); 3.43 (s, 3H); 3.23 (d, J=13.92 Hz, 1H); 3.09 (s, 3H); 2.68 (d, J=13.55 Hz, 1H); 1.45 (s, 9H); 1.21 (s, 3H); LC/MS [M+H]$^+$=541.

Step B. Oxidation

To a −20° C. solution of tert-butyl (1R)-1-benzyl-3-({2-chloro-6-[methyl(methylsulfonyl)amino]isonicotinoyl}amino)-2-hydroxy-1-methylpropylcarbamate (0.400 g, 0.74 mmol) in 8 mL CH$_2$Cl$_2$/4 mL DMSO was added triethylamine (0.41 mL, 2.96 mmol). After 5 min, a solution of pyridine sulfur trioxide (0.471 g, 2.96 mmol) in 3 mL DMSO was added via cannula. After 16 h at ambient temperature, the reaction was quenched with brine (10 mL) and extracted with Et$_2$O (15 mL). The aqueous layer was back extracted with Et$_2$O (10 mL×2). The combined organics were washed with 10% aqueous sodium bisulfite (10 mL), and brine (10 mL), dried over Na$_2$SO$_4$, filtered and concentrated in vacuo. Purification by normal phase chromatography (20->70% EtOAc/hexanes) yielded 0.335 g (84%) of tert-butyl (1R)-1-benzyl-3-({2-chloro-6-[methyl(methylsulfonyl)amino]isonicotinoyl}amino)-1-methyl-2-oxopropylcarbamate as a white solid. NMR (CDCl$_3$, 400 MHz) 7.69 (d, J=1.01 Hz, 1H); 7.51 (d, J=0.92 Hz, 1H); 7.31 (m, 3H); 7.12 (m, 2H); 4.62 (m, 1H); 4.41 (m, 1H); 3.44 (s, 3H); 3.11 (s, 3H); 1.48 (s, 9H); 1.31 (s, 3H); LC/MS [M−C$_4$H$_7$]$^+$=483.

Step C. Cyclodehydration

To a solution of tert-butyl (1R)-1-benzyl-3-({2-chloro-6-[methyl(methylsulfonyl)amino]isonicotinoyl}amino)-1-methyl-2-oxopropylcarbamate (0.190 g, 0.35 mmol) in 2 mL toluene was added Burgess reagent (0.504 g, 2.12 mmol). The reaction was microwaved at 130° C. for 30 min. The clear yellow, top layer of the reaction mixture was concentrated in vacuo and purified by normal phase chromatography (0->50% EtOAc/hexanes) to give tert-butyl (1R)-1-(2-{2-chloro-6-[methyl(methylsulfonyl)amino]pyridin-4-yl}-1,3-oxazol-5-yl)-1-methyl-2-phenylethylcarbamate. NMR (CDCl$_3$, 400 MHz) 7.86 (s, 1H); 7.69 (s, 1H); 7.28 (m, 3H); 7.04 (m, 3H); 3.45 (s, 3H); 3.13 (m, 4H); 1.60 (s, 3H); 1.42 (s, 9H); LC/MS [M+H]$^+$=521.

Intermediate l: N-(4-(hydrazinocarbonyl)-6-{methyl[(2-methylcyclopropyl)methyl]amino}pyridin-2-yl)-N-methylmethanesulfonamide

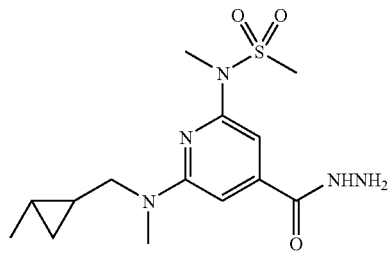

Step A; Coupling

To a solution of Intermediate D (1.95 g, 5.96 mmol) and Boc-hydrazine (0.866 g, 6.55 mmol) in 25 mL DMF was added EDC (1.37 g, 7.15 mmol) and HOAt (0.080 g, 0.596 mmol). The reaction was allowed to proceed for 15 h, then quenched by the addition of 3M LiCl and diluted with EtOAc. The layers were separated, and the aqueous layer was washed with EtOAc (2×). The combined organics were washed with 3M LiCl (2×) and brine, dried over Na$_2$SO$_4$, filtered and concentrated. The residue was purified by normal phase chromatography (15->65% EtOAc/hexanes) to afford the desired coupled adduct as a white foam. $^1$H NMR (CDCl$_3$, 400 MHz) δ 8.17 (br s, 1H), 6.74 (s, 1H), 6.70 (s, 1H), 6.23 (br s, 1H), 3.50 (dd, J=14.5, 6.4 Hz, 1H), 3.33 (s, 3H), 3.30 (dd, J=14.5, 8.3 Hz, 1H), 3.08 (s, 3H), 3.06 (s, 3H), 1.48 (s, 9H), 1.00 (d, J=5.9 Hz, 3H), 0.74-0.60 (m, 2H), 0.37 (m, 1H), 0.23 (m, 1H); LCMS [M+H]$^+$=442.

Step B; Deprotection

HCl was bubbled through a solution of product from Step A (2.50 g, 5.662 mmol) in 100 mL CH$_2$Cl$_2$ at 0° C. for 10 min. The solution went bright yellow. The reaction was warmed to rt for 30 min, then concentrated to afford a yellow solid which was used without further purification. $^1$H NMR (CDCl$_3$, 400 MHz) δ 7.55 (s, 1H), 7.35 (s, 1H), 3.44 (m, 2H), 3.34 (s, 3H), 3.22 (s, 3H), 3.15 (s, 3H), 0.92 (d, J=5.8 Hz, 3H), 0.72 (m, 1H), 0.63 (m, 1H), 0.40 (m, 1H), 0.23 (m, 1H); LCMS [M+H]$^+$=342.

Intermediate m: N-(4-(5-{1-[(diphenylmethylene)amino]ethyl}-1,3,4-oxadiazol-2-yl)-6-{methyl[(2-methylcyclopropyl)methyl]amino}pyridin-2-yl)-N-methylmethanesulfonamide

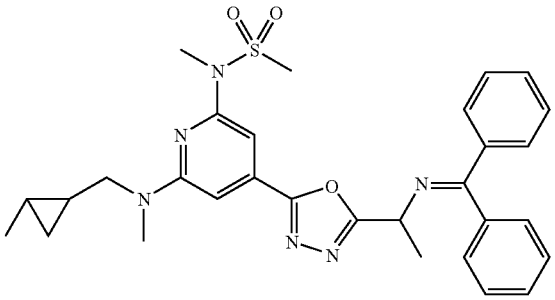

To a solution of N-(4-[5-(1-aminoethyl)-1,3,4-oxadiazol-2-yl]-6-{methyl[(2-methylcyclopropyl)methyl]amino}pyridin-2-yl)-N-methylmethanesulfonamide (0.544 g, 1.26 mmol, example 22) in 10 mL CH$_2$Cl$_2$ was added benzophenone imine (0.25 mL, 1.51 mmol). A white precipitate appeared gradually through the course of the reaction. The reaction was allowed to proceed for 15 h, when a further aliquot of benzophenone imine was added (0.160 mL, 0.894 mmol). After a further 24 h, the reaction was diluted with H$_2$O and EtOAc, and the layers were separated. The aqueous layer was washed with EtOAc(2×), the combined organics were washed with brine, dried over Na$_2$SO$_4$, filtered and concentrated. The residue was purified by normal phase chromatography (2->35% EtOAc/hexanes) to afford N-(4-(5-{1-[(diphenyl methylene)amino]ethyl}-1,3,4-oxadiazol-2-yl)-6-{methyl[(2-methylcyclopropyl)methyl]amino}pyridin-2-yl)-N-methylmethanesulfonamide as a yellow foam. $^1$H NMR (CDCl$_3$, 400 MHz) δ 7.63 (m, 4H), 7.54-7.50 (m, 4H), 7.48 (m, 2H), 7.05 (s, 1H), 6.99 (s, 1H), 4.95 (q, J=6.5 Hz, 1H), 3.52 (dd, J=14.3, 6.2 Hz, 1H), 3.38 (s, 3H), 3.34 (dd, J=14.3, 6.3 Hz, 1H), 3.14 (s, 3H), 3.12 (s, 3H), 1.67 (d, J=6.6 Hz, 3H), 1.01 (d, J=6.0 Hz, 3H), 0.74 (m, 1H), 0.65 (m, 1H), 0.40 (m, 1H), 0.25 (m, 1H); LCMS [M+H]$^+$=559.

Intermediate n: Tert-butyl ((2E)-1-benzyl-4-{2-{benzyl[(2-methylcyclopropyl)methyl]amino}-6-[methyl(methylsulfonyl)amino]pyridin-4-yl}-1-methyl-4-oxobut-2-en-1-yl)carbamate (Scheme 24)

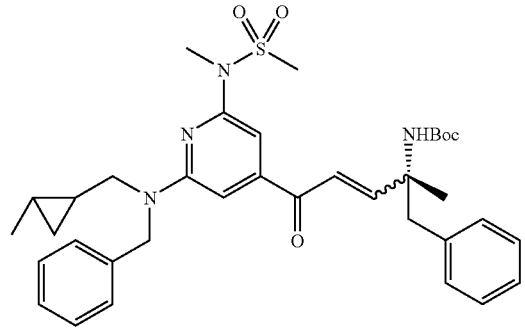

Step A: Preparation of Weinreb Amide

To a solution of intermediate C (1.0 g, 2.23 mmol) in 10 mL dichloromethane was added N,O-dimethylhydroxlamine hydrochloride (226 mg, 2.32 mmol), diisopropylethylamine (574 μL, 3.48 mmol), EDC (577 mg, 3.01 mmol), and HOAt (347 mg, 2.55 mmol). The resulting solution was stirred at rt for 16 h, then poured onto 0.3N HCl (20 mL) and extracted with ethyl acetate (3×50 mL). The combined organics were washed with aqueous sodium bicarbonate (75 mL) followed by brine (75 mL) and then dried over sodium sulfate and concentrated. Purification by automated flash chromatography (silica gel cartridge, 0-100% ethyl acetate/hexanes over 20 minutes) afforded 2-{benzyl[(2-methylcyclopropyl)methyl]amino}-6-[(isopropylsulfonyl)(methyl)amino]-N-methoxy-N-methylisonicotinamide as a yellow oil. LCMS [M+H]=475.1.

Step B: Preparation of Methyl Ketone

To a −78° C. solution of 2-{benzyl[(2-methylcyclopropyl)methyl]amino}-6-[(isopropylsulfonyl)(methyl)amino]-N-methoxy-N-methylisonicotinamide (860 mg, 1.81 mmol) from Step A in 6 mL dry THF was added methylmagnesium bromide (3.62 mL, 10.8 mmol, 3M solution in diethyl ether). The reaction mixture was allowed to slowly warm to 0° C. over 1 h, at which time it was poured onto 20 mL of sat. ammonium chloride and extracted with ethyl acetate (3×30 mL). The combined organics were washed with brine (30 mL), dried over sodium sulfate, and concentrated. Purification by automated flash chromatography (silica gel cartridge, 0-100% ethyl acetate/hexanes over 35 minutes) afforded N-(4-acetyl-6-{benzyl[(2-methylcyclopropyl)methyl]amino}pyridin-2-yl)-N-methylpropane-2-sulfonamide as a bright yellow solid. LCMS [M+H]=430.1.

Step C: Aldol Condensation

To a −78° C. solution of N-(4-acetyl-6-{benzyl[(2-methylcyclopropyl)methyl]amino}pyridin-2-yl)-N-methylpropane-2-sulfonamide (100 mg, 0.23 mmol) from Step B in 1.5 mL dry THF was added lithium bis(trimethylsilyl)amide (244 µL, 0.49 mmol, 2M solution in THF), and the resulting mixture was allowed to stir for 15 min. To this mixture was added a solution of tert-butyl (1R)-1-benzyl-1-methyl-2-oxoethylcarbamate (61 mg, 0.23 mmol, prepared according to preparation of intermediate III up to step C) dissolved in 1 mL dry THF. The solution was allowed to slowly warm to rt and then allowed to stir for an additional 16 h, at which time it was quenched with a saturated solution of ammonium chloride (15 mL) and extracted with ethyl acetate (2×25 mL). The combined organics were dried over sodium sulfate and concentrated. Purification by reverse-phase chromatography afforded tert-butyl (1R,2E)-1-benzyl-4-{2-{benzyl[(2-methylcyclopropyl)methyl]amino}-6-[(isopropylsulfonyl)(methyl)amino]pyridin-4-yl}-1-methyl-4-oxobut-2-enylcarbamate, intermediate n, as an orange oil. LCMS [M+H]=675.3.

EXAMPLE 1

N-(4-[5-(1R-amino-1-methyl-2-phenylethyl)-1,3,4-oxadiazol-2-yl]-6-{benzyl[(2-methylcyclopropyl)methyl]amino}pyridin-2-yl)-N-methylmethanesulfonamide (Scheme 8)

Step A: Coupling

To a solution of Intermediate C (100 mg, 0.25 mmol) and Intermediate I (87 mg, 0.30 mmol) in DMF (5 mL) was added HOAt (37 mg, 0.27 mmol) and EDC (57 mg, 0.30 mmol). The reaction mixture was stirred at rt for 2 h, treated with N-(tert-butoxycarbonyl)-D-α-methylphenylalaninhydrazamide (20 mg, 0.07 mmol, intermediate I), stirred at rt for 1 h, diluted with EtOAc, washed with water, aq LiCl (×3), dried over Na$_2$SO$_4$, concentrated in vacuo and purified by flash chromatography (silica, 10-50% EtOAc/hexanes) to provide tert-butyl [1R-benzyl-2-oxo-1-methyl-2-{2-{methyl[(2-methylcyclopropyl)methyl]amino}-6-[methyl(methylsulfonyl)amino]isonicotinoyl}hydrazino)ethyl]carbamate as a white foam. $^1$H NMR (400 MHz, CDCl$_3$) δ 9.35 (br s, 1H), 8.64 (br s, 1H), 7.38-7.14 (m, 10H), 6.79 (s, 2H), 4.88 (A of AB, d, J=17.2 Hz, 1H), 4.83 (B of AB, d, J=17.2 Hz, 1H), 4.66 (s, 1H), 3.60-3.48 (m, 2H), 3.36-3.24 (m, 1H), 3.28 (s, 3H), 3.07 (B of AB, d, J=14.0 Hz, 1H), 2.84 (s, 3H), 1.50 (s, 9H), 1.45 (s, 3H), 0.98 (d, J=6.0 Hz, 3H), 0.86-0.76 (m, 1H), 0.65-0.55 (m, 1H), 0.39-0.31 (m, 1H), 0.30-0.23 (m, 1H).

Step B: Cyclodehydration and Boc Removal

A solution of tert-butyl [1R-benzyl-2-oxo-1-methyl-2-(2-{2-{methyl[(2-methylcyclopropyl)methyl]amino}-6-[methyl(methylsulfonyl)amino]isonicotinoyl}hydrazino)ethyl]carbamate (140 mg, 0.21 mmol) and methoxycarbonylsulfamoyl-triethylammonium hydroxide (197 mg, 0.83 mmol, Burgess reagent) in THF (5 mL) was irradiated under microwave (Smith Synthesizer) at 120° C. for 10 min, concentrated in vacuo and purified by flash chromatography (silica, 0-30% EtOAc/hexanes) to provide tert-butyl [1-(5-{2-{benzyl[(2-methylcyclopropyl)methyl]amino}-6-[methyl(methylsulfonyl)amino]pyridin-4-yl}-1,3,4-oxadiazol-2-yl)-1-methyl-2-phenylethyl]carbamate. Boc removal by exposure to HCl (g) saturated EtOAc for 0.5 h, concentration and lyophilization from dioxane/water afforded N-(4-[5-(1-amino-1-methyl-2-phenylethyl)-1,3,4-oxadiazol-2-yl]-6-{benzyl[(2-methylcyclopropyl)methyl]amino}pyridin-2-yl)-N-methylmethanesulfonamide as the hydrochloride. $^1$H NMR (400 MHz, CD3OD) δ 7.33-7.18 (m, 8H), 7.08-7.02 (m, 3H), 6.94 (d, J=2.8 Hz, 1H), 4.98-4.82 (m, 2H), 3.74-3.66 (m, 1H), 3.48-3.36 (m, 1H), 3.41 (s, 3H), 3.34-3.26 (m, 2H), 2.96 (s, 3H), 1.82 (s, 3H), 0.98 (d, J=6.0 Hz, 3H), 0.91-0.81 (m, 1H), 0.73-0.62 (m, 1H), 0.48-0.39 (m, 1H), 0.29-0.19 (m, 1H). HRMS (ES, M+H) calcd. for C30H36N6O3S: 561.2643, found: 561.2655.

Use of the preferred enantiomer trans-S,S from Intermediate A, step B, affords the preparation of the preferred enantiopure S,S,R example.

EXAMPLE 2

N-(4-[5-(1R-amino-1-methyl-2-phenylethyl)-1,3,4-oxadiazol-2-yl]-6-{[(2-methylcyclopropyl)methyl]amino}pyridine-2-yl)-N-methylmethanesulfonamide

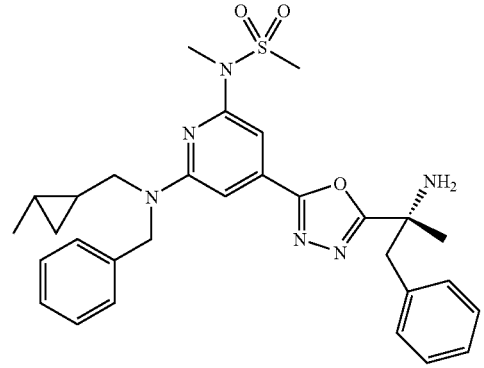

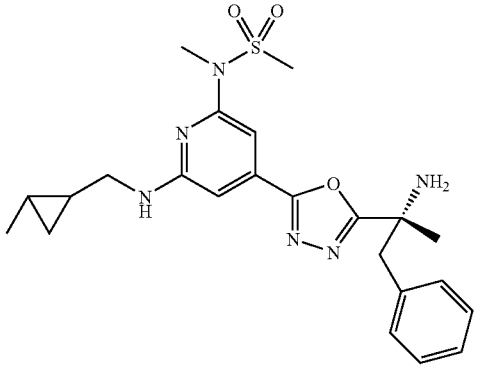

A solution of tert-butyl [1-(5-{2-{benzyl[(2-methylcyclopropyl)methyl]amino}-6-[methyl(methylsulfonyl)amino]pyridin-4-yl}-1,3,4-oxadiazol-2-yl)-1R-methyl-2-phenylethyl]carbamate (94 mg, 0.14 mmol, from Example 1) in EtOH (10 mL) and TFA (0.011 mL, 0.14 mmol) was hydrogenated over 20% Pd(OH)$_2$/C (20 mg), at 40° C., under 1 atm H$_2$, for 3 h. Filtration and concentration, followed by Boc removal (HCl(g) saturated EtOAc), concentration and trituration in Et$_2$O afforded N-(4-[5-(1R-amino-1-methyl-2-phenylethyl)-1,3,4-oxadiazol-2-yl]-6-{[(2-methylcyclopropyl)methyl]amino}pyridine-2-yl)-N-methylmethanesulfonamide hydrochloride as a pale yellow solid. $^1$H NMR (400 MHz, CD$_3$OD) δ 7.35-7.30 (m, 3H), 7.11-7.05 (m, 2H), 6.99 (d, J=1.2 Hz, 1H), 6.93 (d, J=1.2 Hz, 1H), 3.45 (br s, 2H), 3.37 (s, 3H), 3.28-3.20 (m, 2H), 3.19 (s, 3H), 1.82 (s, 3H), 1.06 (d, J=6.0 Hz, 3H), 0.90-0.80 (m, 1H), 0.73-0.65 (m, 1H), 0.47-0.41 (m, 1H), 0.31-0.24 (m, 1H). HRMS (ES, M+H) calcd. for C$_{23}$H$_{30}$N$_6$O$_3$S: 471.2173, found: 471.2175.

Use of the preferred enantiomer trans-S,S from Intermediate A, step B, affords the preparation of the preferred enantiopure S,S,R example.

EXAMPLE 3

N-(4-[5-(1R-amino-1-methyl-2-phenylethyl)-1,3,4-oxadiazol-2-yl]-6-{methyl[(2-methylcyclopropyl)methyl]amino}pyridine-2-yl)-N-methylmethanesulfonamide

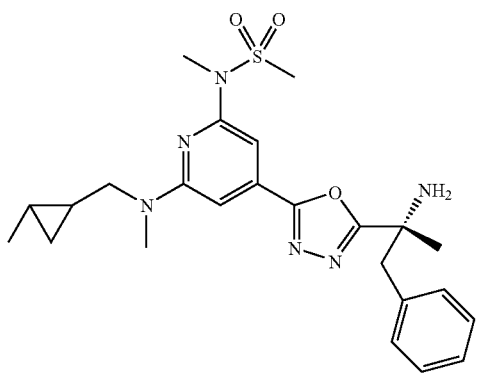

Prepared from 2-{benzyl[(2-methylcyclopropyl)methyl]amino}-6-[methyl(methylsulfonyl)amino]isonicotinic acid and N-methyl-1-(2trans -methylcyclopropyl)methenamine using a similar procedure as described in Example 1. HRMS (ES, M+H) calcd. for C$_{24}$H$_{32}$N$_6$O$_3$S: 485.2330, found: 485.2355.

Use of the preferred enantiomer trans-S,S from Intermediate A, step B, affords the preparation of the preferred enantiopure S,S,R example.

EXAMPLE 4

N-(4-[5-(1R-amino-1-methyl-2-phenylethyl)-1,3,4-oxadiazol-2-yl]-6-{benzyl[(2-methylcyclopropyl)methyl]amino}pyridin-2-yl)-N-methylpropane-2-sulfonamide

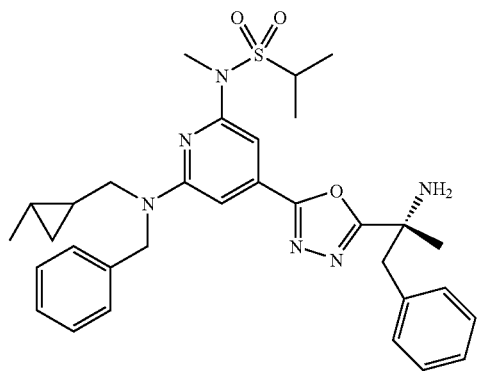

Prepared from 2-{benzyl[(2-methylcyclopropyl)methyl]amino}-6-[methyl(isopropylsulfonyl)amino]isonicotinic acid (prepared from methyl(isopropylsulfonyl)amine using a similar procedure as described in the preparation of intermediate C) and N-(tert -butoxycarbonyl)-D-α-methylphenylalaninhydrazamide using a similar procedure as described in Example 1. HRMS (ES, M+H) calcd. for C$_{32}$H$_{40}$N$_6$O$_3$S: 589.2955, found: 589.2920.

Use of the preferred enantiomer trans-S,S from Intermediate A, step B, affords the preparation of the preferred enantiopure S,S,R example.

EXAMPLE 5

N-(4-[5-(1R-amino-1-methyl-2-phenylethyl)-1,3,4-oxadiazol-2-yl]-6-{[(2-methylcyclopropyl)methyl]amino}pyridine-2-yl)-N-methylpropane-2-sulfonamide

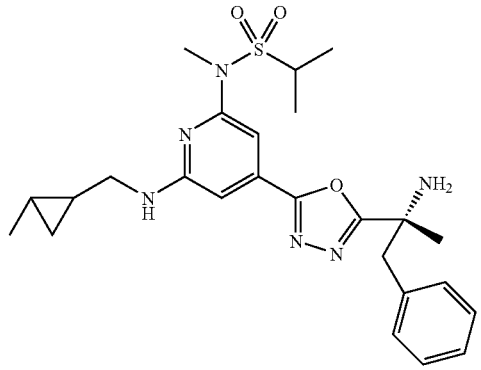

Prepared from Example 4 using a similar procedure as described in Example 2. HRMS (ES, M+H) calcd. for C$_{25}$H$_{34}$N$_6$O$_3$S: 499.2486, found: 499.2499.

Use of the preferred enantiomer trans-S,S from Intermediate A, step B, affords the preparation of the preferred enantiopure S,S,R example.

EXAMPLE 6

N-(4-[5-(1R-amino-1-methyl-2-phenylethyl)-1,3,4-oxadiazol-2-yl]-6-{(2,2-difluoroethyl)[(2-methylcyclopropyl)methyl]amino}pyridin-2-yl)-N-methylmethanesulfonamide (Scheme 8)

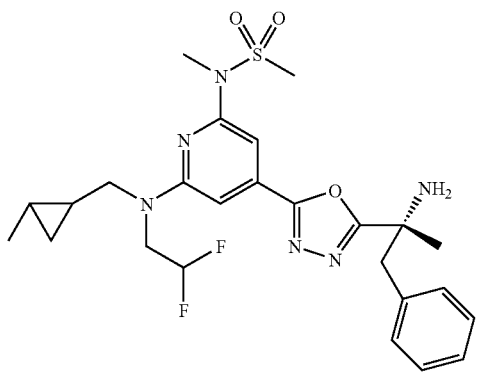

Prepared from Intermediate P using a similar procedure as described in Example 1. HRMS [M+1]⁺ calc'd=535.2298, found=535.2288.

Use of the preferred enantiomer trans-S,S from Intermediate A, step B, affords the preparation of the preferred enantiopure S,S,R example.

EXAMPLE 7

N-(4-[5-(1R-amino-1-methyl-2-phenylethyl)-1,3,4-oxadiazol-2-yl]-6-{(2-methoxyethyl)[(2-methylcyclopropyl)methyl]amino}pyridin-2-yl)-N-methylmethanesulfonamide (Scheme 8)

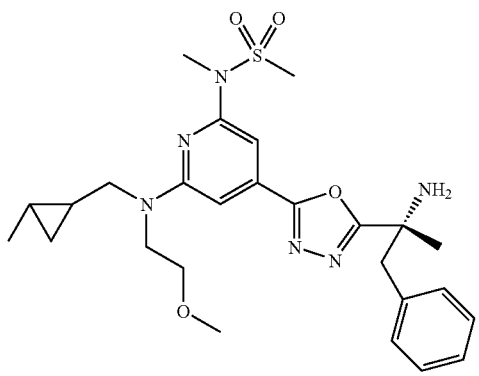

Prepared from Intermediate Q using a similar procedure as described in Example 1. HRMS [M+1]⁺ calc'd=529.2592, found=529.2591.

Use of the preferred enantiomer trans-S,S from Intermediate A, step B, affords the preparation of the preferred enantiopure S,S,R example.

EXAMPLE 8

N-(4-[5-(1R-amino-1-methyl-2-phenylethyl)-1,3,4-oxadiazol-2-yl]-6-{(2,2-difluoroethyl)[(2-methylcyclopropyl)methyl]amino}pyridin-2-yl)-N-methylpropane-2-sulfonamide (Scheme 8)

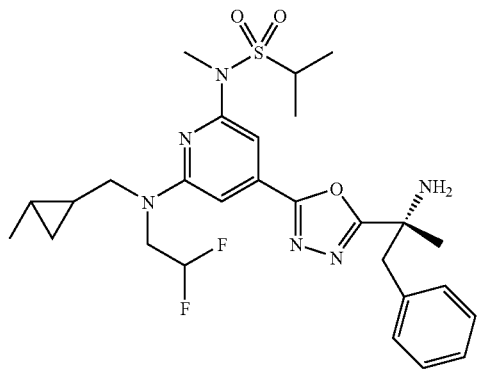

Prepared from Intermediate R using a similar procedure as described in Example 1. HRMS [M+1]+ calc'd=563.2611, found=562.2603.

Use of the preferred enantiomer trans-S,S from Intermediate A, step B, affords the preparation of the preferred enantiopure S,S,R example.

EXAMPLE 9

N-(4-[5-(1R-amino-1-methyl-2-phenylethyl)-1,3,4-oxadiazol-2-yl]-6-{(2-fluoroethyl)[(2-methylcyclopropyl)methyl]amino}pyridin-2-yl)-N-methylpropane-2-sulfonamide (Scheme 8)

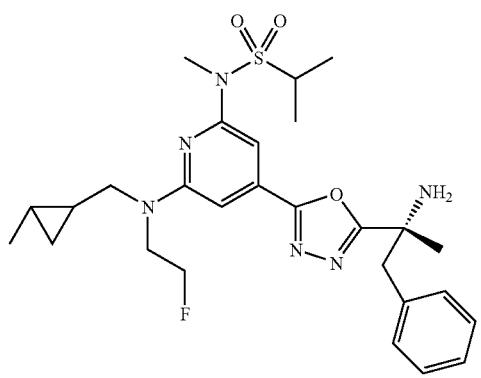

Prepared from Intermediate S using a similar procedure as described in Example 1. HRMS [M+1]⁺ calc'd=545.2705, found=545.2727.

Use of the preferred enantiomer trans-S,S from Intermediate A, step B, affords the preparation of the preferred enantiopure S,S,R example.

EXAMPLE 10

N-(4-[5-(1R-amino-1-methyl-2-phenylethyl)-1,3,4-oxadiazol-2-yl]-6-{(2-methoxyethyl)[(2-methylcyclopropyl)methyl]amino}pyridin-2-yl)-N-methylpropane-2-sulfonamide (Scheme 8)

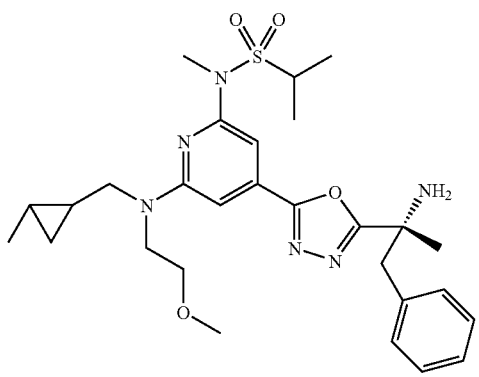

Prepared from Intermediate T using a similar procedure as described in Example 1. HRMS [M+1]+ calc'd=557.2905, found=557.2900.

Use of the preferred enantiomer trans-S,S from Intermediate A, step B, affords the preparation of the preferred enantiopure S,S,R example.

EXAMPLE 11

N-(4-[5-(1R-amino-1-methyl-2-phenylethyl)-1,3,4-oxadiazol-2-yl]-6-{[2-(dimethylamino)ethyl][(2-methylcyclopropyl)methyl]amino}pyridin-2-yl)-N-methylpropane-2-sulfonamide (Scheme 8)

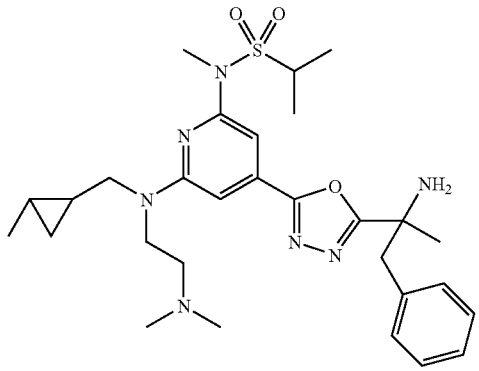

Prepared from Intermediate U using a similar procedure as described in Example 1. LCMS [M+H]+=570.4.

Use of the preferred enantiomer trans-S,S from Intermediate A, step B, affords the preparation of the preferred enantiopure S,S,R example.

EXAMPLE 12

N-(4-[5-(1R-amino-1-methyl-2-phenylethyl)-1,3,4-oxadiazol-2-yl]-6-{[3-(dimethylamino)propyl][(2-methylcyclopropyl)methyl]amino}pyridin-2-yl)-N-methylpropane-2-sulfonamide (Scheme 8)

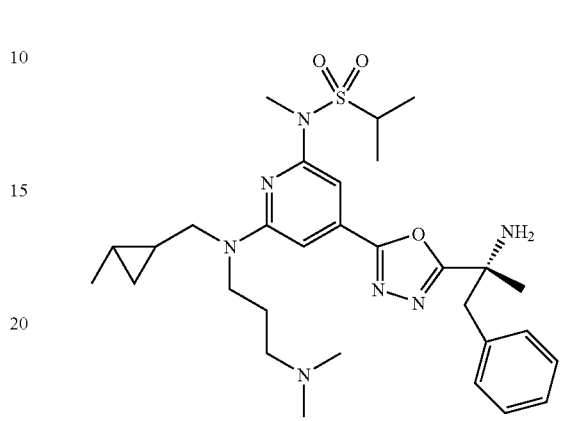

Prepared from Intermediate V using a similar procedure as described in Example 1. HRMS [M+1]+ calc'd=584.3378, found=584.3382.

Use of the preferred enantiomer trans-S,S from Intermediate A, step B, affords the preparation of the preferred enantiopure S,S,R example.

EXAMPLE 13

N-[4-[5-(1R-amino-1-methyl-2-phenylethyl)-1,3,4-oxadiazol-2-yl]-6-({1-[(1S,2S)-2-methylcyclopropyl]ethyl}amino)pyridin-2-yl]-N-methylmethanesulfonamide (Scheme 8, 2$^{nd}$ line)

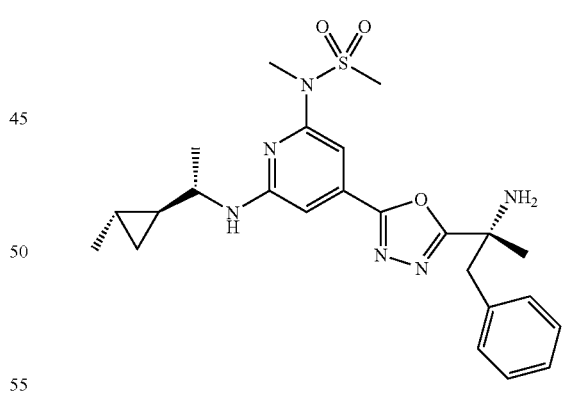

Step A. Pd Coupling

To a solution of (1S)-1-[(1S,2S)-2-methylcyclopropyl]ethanaminium chloride (intermediate P, 0.045 g, 0.33 mmol) and tert-butyl (1R)-1-(5-{2-chloro-6-[methyl(methylsulfonyl)amino]pyridin-4-yl}-1,3,4-oxadiazol-2-yl)-1R-methyl-2-phenylethylcarbamate (intermediate h, 0.173 g, 0.33 mmol) in 1 mL DMF was added $K_3PO_4$ (0.352 g, 1.66 mmol) and Pd(PtBu$_3$)$_2$ (0.025 g, 0.05 mmol). The sealed reaction was heated at 110° C. for 12 h and then diluted with EtOAc (30 mL) and filtered over a pad of celite. The celite was washed with EtOAc (100 mL). The filtrate was concentrated in vacuo and purified by normal phase chromatography (0->50% EtOAc/hexanes) followed by reverse phase LC. The resulting material was diluted with EtOAc (40 mL) and washed with saturated sodium bicarbonate solution (20 mL). The aqueous layer was back extracted with EtOAc (20 mL). The combined organics were washed with brine (40 mL), dried over Na$_2$SO$_4$, filtered and concentrated in vacuo to give 0.030 g (16%) of tert-butyl (1R)-1R-methyl-1-(5-{2-({(1S)-1-[(1S,2S)-2-methylcyclopropyl]ethyl}amino)-6-[methyl(methylsulfonyl)amino]pyridin-4-yl}-1,3,4-oxadiazol-2-yl)-2-phenylethylcarbamate as a yellow residue. NMR (CDCl$_3$, 400 MHz) 7.27 (m, 3H); 7.03 (m, 3H); 6.79 (s, 1H); 3.55 (d, J=13.46 Hz, 1H); 3.43 (m, 2H); 3.37 (s, 3H); 3.15 (s, 3H); 1.71 (s, 3H); 1.42 (s, 9H); 1.29 (d, J=6.41 Hz, 3H); 1.07 (d, J=5.77 Hz, 3H); 0.67 (m, 2H); 0.50 (m, 1H); 0.26 (m, 1H); LC/MS [M+H]$^+$=585.

Step B. Boc Removal

HCl$_{(g)}$ was bubbled through a 0° C. solution of tert-butyl (1R)-1-methyl-1-(5-{2-({(1S)-1-[(1S,2S)-2-methylcyclopropyl]ethyl}amino)-6-[methyl(methylsulfonyl)amino]pyridin-4-yl}-1,3,4-oxadiazol-2-yl)-2-phenylethylcarbamate (0.030 g, 0.05 mmol) in 1 mL CH$_2$Cl$_2$ for 5 min. After 10 min at 0° C., the reaction was then concentrated in vacuo and taken up in DMF. Purification by reverse phase LC followed by lyophilization yielded 0.008 g (27%) of (2R)-2-(5-{2-({(1S)-1-[(1S,2S)-2-methylcyclopropyl]ethyl}amino)-6-[methyl(methylsulfonyl)amino]pyridin-4-yl}-1,3,4-oxadiazol-2-yl)-1-phenylpropan-2-aminium trifluoroacetate as a white solid. NMR (CDCl$_3$, 400 MHz) 7.31 (m, 3H); 7.05 (m, 2H); 6.91 (d, J=1.1 Hz, 1H); 6.84 (d, J=1.1 Hz, 1H); 3.55 (m, 1H); 3.40 (s, 2H); 3.16 (s, 3H); 1.83 (s, 3H); 1.28 (d, J=6.4 Hz, 3H); 1.06 (d, J=5.7 Hz, 3H); 0.67 (m, 2H); 0.53 (m, 1H); 0.21 (m, 1H); LC/MS [M+H]$^+$=485.

Additional compounds wherein X is an oxadiazole were prepared as described in Table 1. References to Methods A and B refer to Scheme 8, Method A and Scheme 8, Method B, respectively.

TABLE I

Oxadiazole Examples

| Ex # | intermediate | Mode of prep |
|---|---|---|
| 14 | 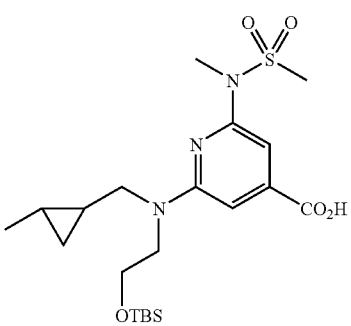 | Method A, intermediate T, w/ desyllation |
| 15 | 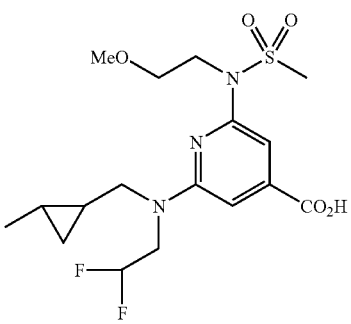 | Method A, intermediate K, 2-methoxyethyl)-methylamine, MsCl |
| 16 | 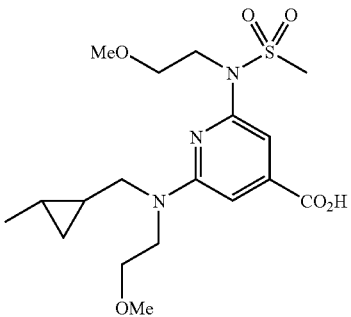 | Method A, intermediate N, 2-methoxyethyl)-methylamine, MsCl |

TABLE I-continued
| | | |
|---|---|---|
| 17 | 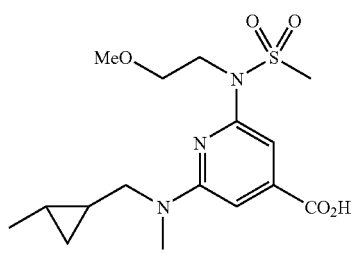 | Method A, intermediate B, 2-methoxyethyl)-methylamine, MsCl |
| 18 | 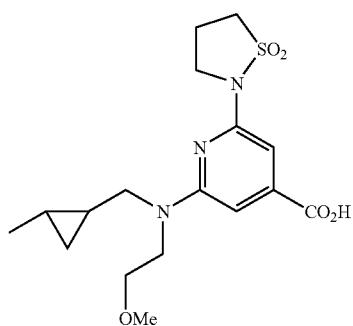 | Method A, intermediate N, isothiazolidine 1,1-dioxide |
| 19 | 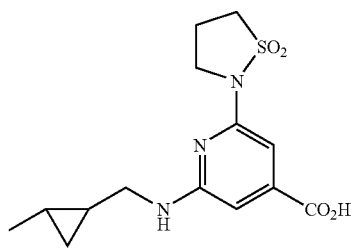 | Method A, intermediate A, isothiazolidine 1,1-dioxide, debenzylation |
| 20 | 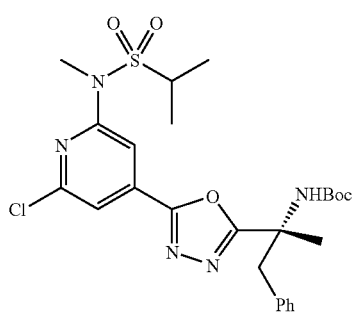 | Method B, 2-propylpyrrolidine, iPrSO$_2$Cl |
| 21 | 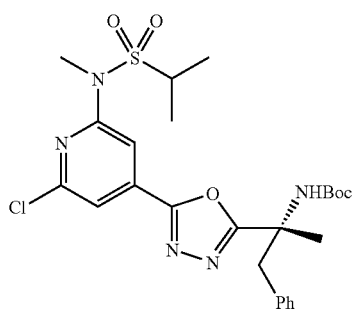 | Method B, 2-vinylpyrrolidine, iPrSO$_2$Cl |

TABLE I-continued
| | | |
|---|---|---|
| 22 | 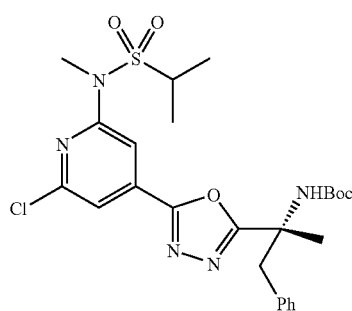 | Method B, 2-methylacetylene, iPrSO$_2$Cl |
| 23 | 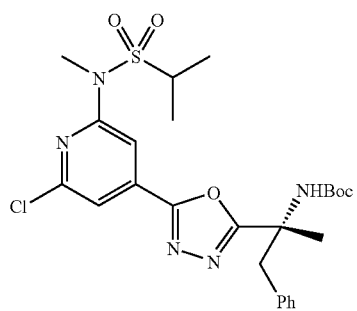 | Method B, 1-methyl-2-(2-furyl)ethylamine, iPrSO$_2$Cl |
| 24 | 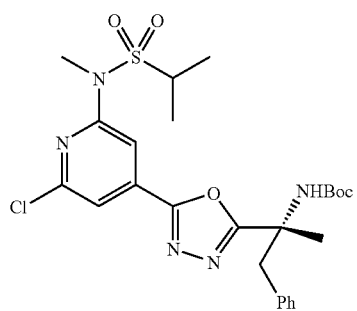 | Method B, 2-(2-furyl)ethylamine iPrSO$_2$Cl |
| 25 | 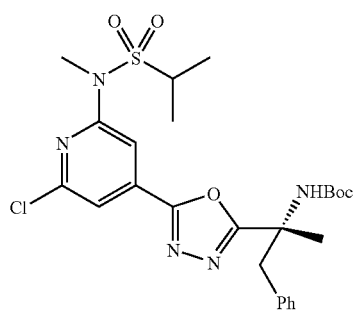 | Method B, 2-phenylpyrrolidine, iPrSO$_2$Cl |
| 26 | 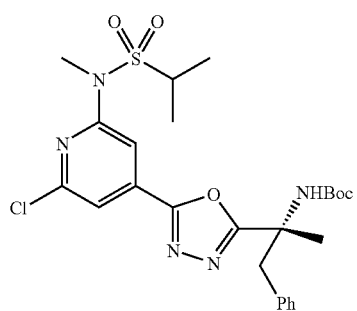 | Method B, 1-methyl-2-(2-benzofuryl)ethylamine, iPrSO$_2$Cl |

TABLE I-continued
| | | |
|---|---|---|
| 27 | 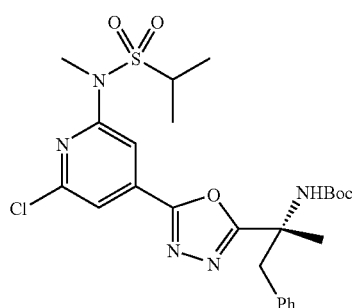 | Method B, 2-methyl-2-phenylethylamine, iPrSO$_2$Cl |
| 28 | 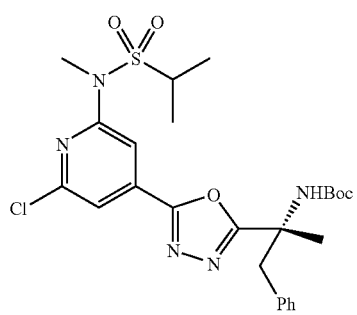 | Method B, 2-phenylethylamine, iPrSO$_2$Cl |
| 29 | 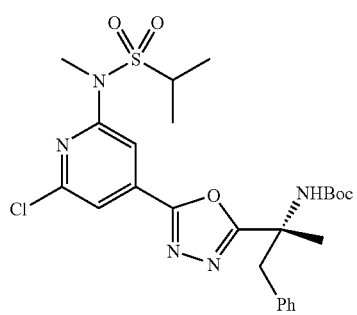 | Method B, 2-(4-chloro-furyl-2-yl)ethylamine, iPrSO$_2$Cl |
| 30 | 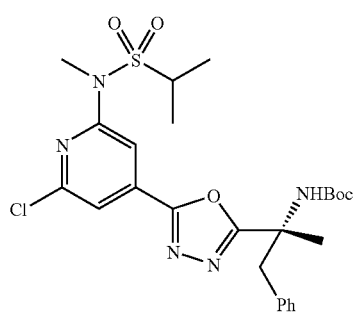 | Method B, 2-(2-methyl-propyl)pyrrolidine, iPrSO$_2$Cl |
| 31 | 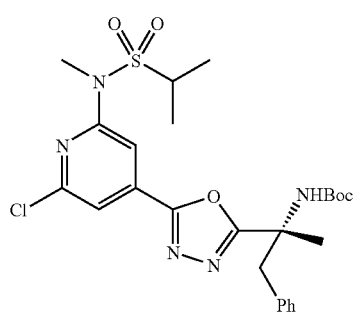 | Method B, 2-(methylacetylene)ethylamine, iPrSO$_2$Cl |

TABLE I-continued
| | | |
|---|---|---|
| 32 | 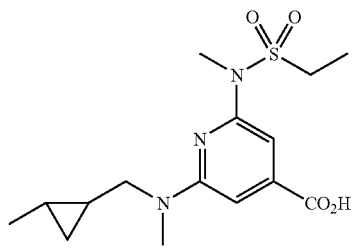 | Method A, intermediate B, EtSO$_2$Cl |
| 33 | 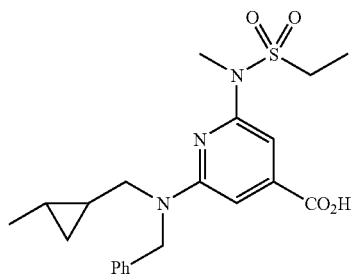 | Method A, intermediate A, debenzylation |
| 34 | 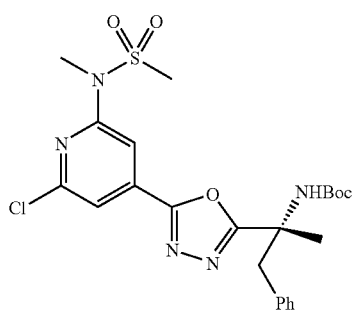 | Method B, intermediate P, see ex oxadiazole-Pd |
| 35 | 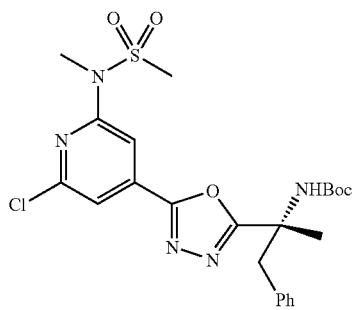 | Method B, intermediate Q |
| 36 | 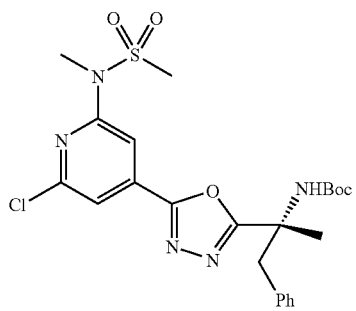 | Method B, intermediate S |

TABLE I-continued

| | | |
|---|---|---|
| 37 | [structure] | Method B, intermediate R |
| 38 | [structure] | Intermediate i, methanesulfonamide, Pd coupling |

| Ex # | Structure | ES M + 1 |
|---|---|---|
| 14 | [structure] | 515 |
| 15 | [structure] | 579 |
| 16 | [structure] | 573 |

TABLE I-continued
| | | |
|---|---|---|
| 17 | 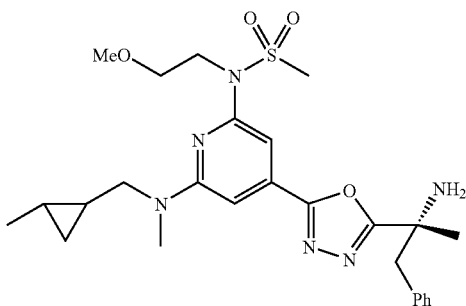 | 529 |
| 18 | 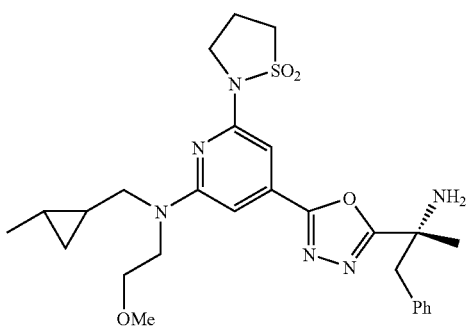 | 541 |
| 19 | 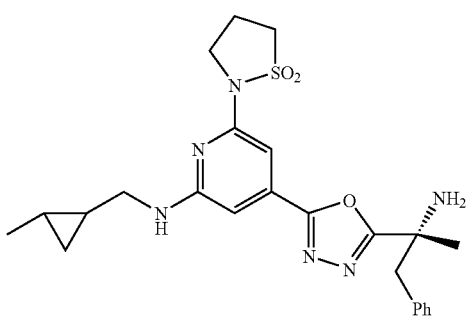 | 483 |
| 20 | 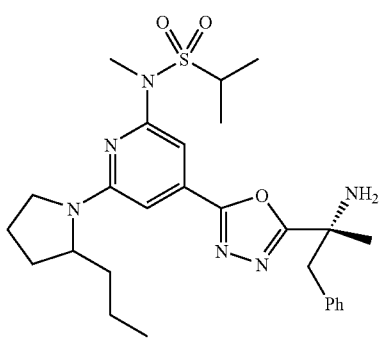 | 527 |
| 21 | 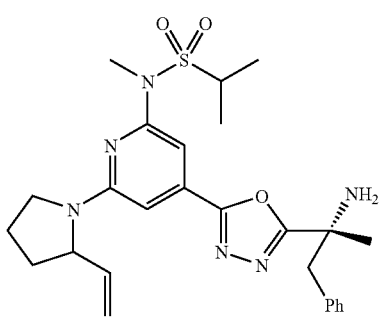 | 511 |

TABLE I-continued
| | | |
|---|---|---|
| 22 | 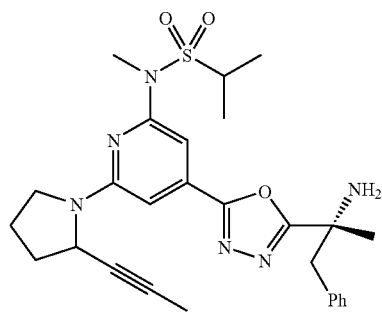 | 523 |
| 23 | 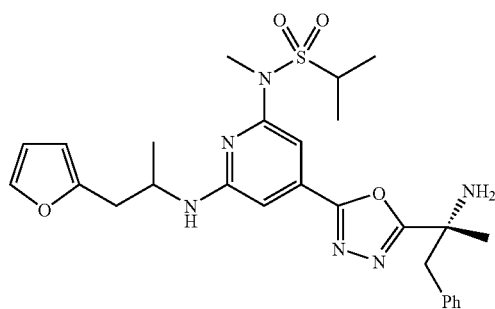 | 539 |
| 24 | 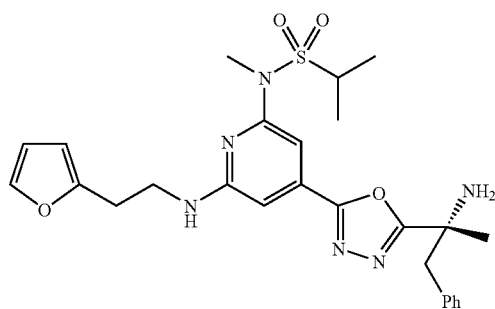 | 525 |
| 25 | 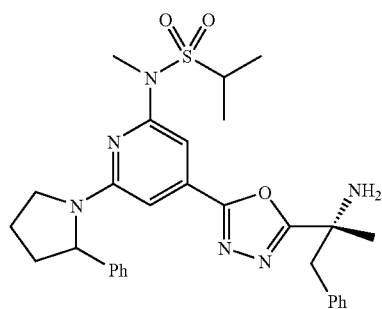 | 561 |
| 26 | 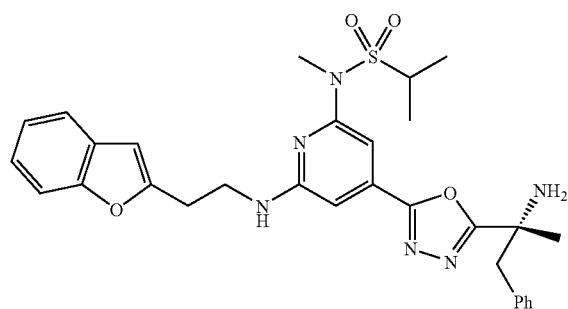 | 575 |

TABLE I-continued
| | | |
|---|---|---|
| 27 | 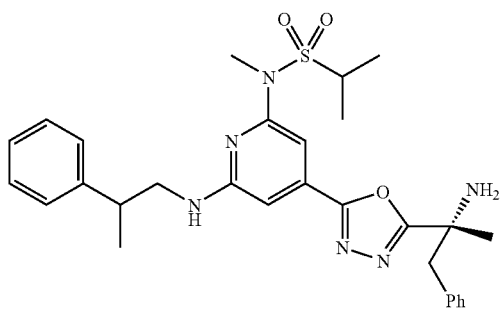 | 549 |
| 28 | 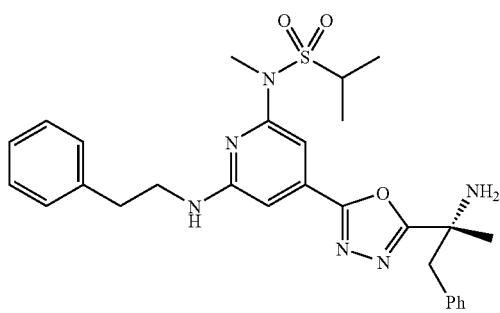 | 535 |
| 29 | 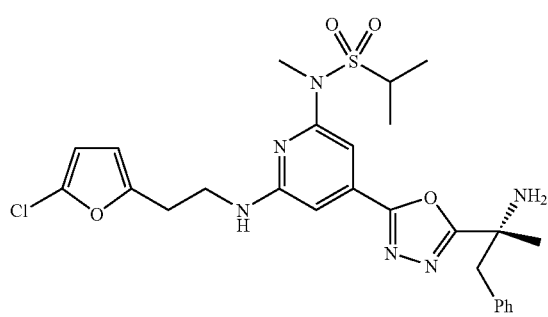 | 560 |
| 30 | 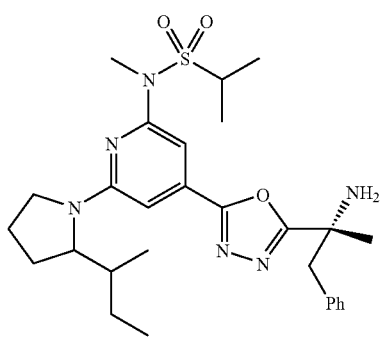 | 541 |
| 31 | 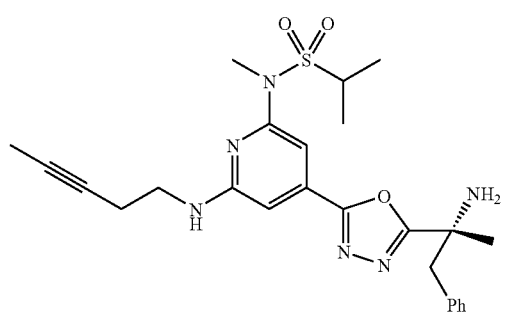 | 497 |

TABLE I-continued
| | | |
|---|---|---|
| 32 | 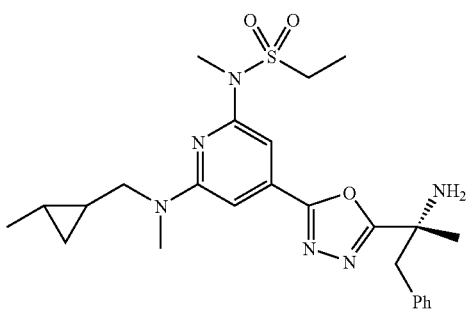 | 499 |
| 33 | 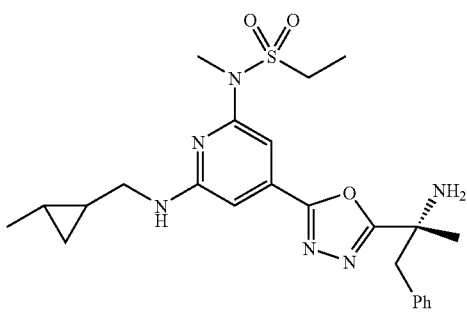 | 485 |
| 34 | 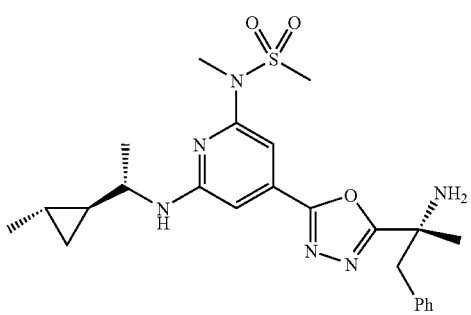 | 485 |
| 35 | 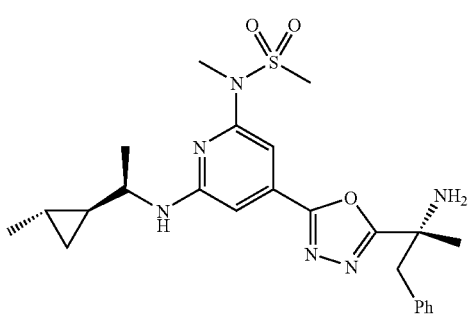 | 485 |
| 36 | 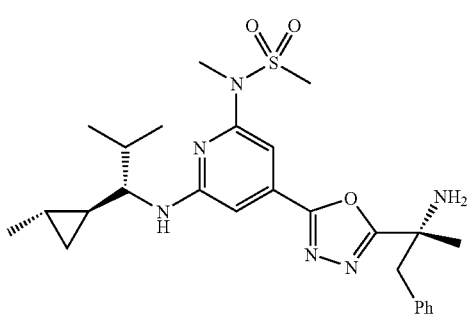 | 513 |

TABLE I-continued

37 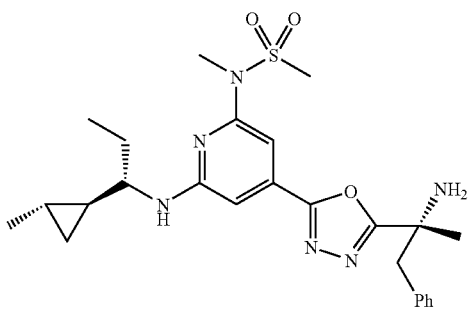 499

38 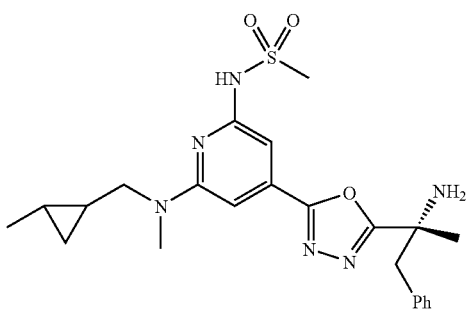 471

EXAMPLE 39

N-(4-[2-(1R-amino-1-methyl-2-phenylethyl)-1,3-oxazol-5-yl]-6-{methyl[(2-methylcyclopropyl)methyl]amino}pyridin-2-yl)-N-methylmethanesulfonamide (Scheme 16)

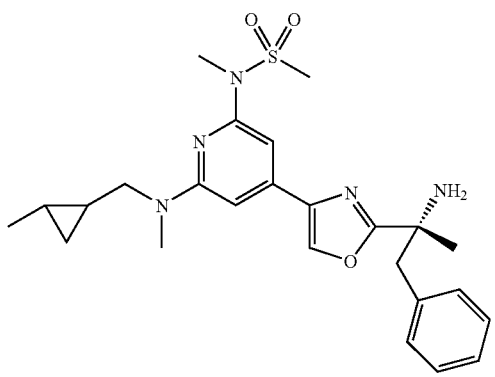

A solution of Intermediate E (100 mg, 0.25 mmol) and Intermediate II (103 mg, 0.37 mmol) in DMF (0.5 mL) was heated at 120° C. for 1 h. The crude product was purified by preparative HPLC (5->95% $CH_3CN/H_2O$, 0.1% added TFA, C18 PRO YMC 20×150 mm) to afford tert-butyl [1R-methyl-1-(4-{2-{methyl[(2-methylcyclopropyl)methyl]amino}-6-[methyl(methylsulfonyl)amino]pyridin-4-yl}-1,3-oxazol-2-yl)-2-phenylethyl]carbamate. Boc removal (HCl(g) saturated EtOAc), concentration and purification by preparative HPLC (5->95% $CH_3CN/H_2O$, 0.1% added TFA, C18 PRO YMC 20×150 mm) afforded N-(4-[2-(1R-amino-1-methyl-2-phenylethyl)-1,3-oxazol-5-yl]-6-{methyl[(2-methylcyclopropyl)methyl]amino}pyridin-2-yl)-N-methylmethanesulfonamide as a TFA salt. $^1$H NMR (400 MHz, $CD_3OD$) δ 8.58 (s, 1H), 7.32-7.26 (m, 3H), 7.02-6.96 (m, 2H), 6.92 (d, J=0.8 Hz, 1H), 6.84 (d, J=0.8 Hz, 1H), 3.62-3.53 (m, 1H), 3.43-3.26 (m, 3H), 3.33 (s, 3H), 3.14 (s, 3H), 3.11 (s, 3H), 1.81 (s, 3H), 1.03 (d, J=6.0 Hz, 3H), 0.81-0.66 (m, 2H), 0.48-0.41 (m, 1H), 0.27-0.21 (m, 1H). HRMS (ES, M+H) calcd. for $C_{25}H_{33}N_5O_3S$: 484.2377, found: 484.2400.

Use of the preferred enantiomer trans-S,S from Intermediate A, step B, affords the preparation of the preferred enantiopure S,S,R example.

EXAMPLE 40

N-(4-[2-(1R-amino-1-methyl-2-phenylethyl)-1,3-oxazol-5-yl]-6-{methyl[(2-methylcyclopropyl)methyl]amino}pyridin-2-yl)-N-methylmethanesulfonamide (Scheme 14)

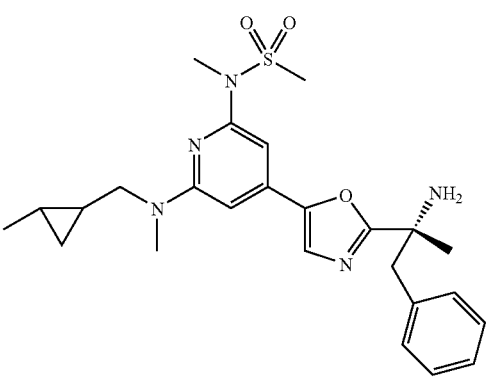

A solution of Intermediate G (25 mg, 0.04 mmol) and Burgess reagent (40 mg, 0.17 mmol) in THF (0.5 mL) was irradiated under microwave (Smith Synthesizer) at 80° C. for 25 min, concentrated under a flow on $N_2$ and purified by flash chromatography (silica, 0-40% EtOAc/hexanes). Boc removal with HCl (1 mL, 4 mmol, 4M in dioxane) followed by lyophilization provided N-(4-[2-(1R-amino-1-methyl-2-phenylethyl)-1,3-oxazol-5-yl]-6-{methyl[(2-methylcyclopropyl)methyl]amino}pyridin-2-yl)-N-methylmethanesulfonamide as a TFA salt. $^1$H NMR (400 MHz, $CD_3OD$) δ 7.84 (s, 1H), 7.32-7.26 (m, 3H), 7.04-6.97 (m, 2H), 6.92 (s, 1H), 6.81 (s, 1H), 3.70-3.57 (m, 1H), 3.50-3.36 (m, 1H), 3.42 (s, 2H), 3.38 (s, 3H), 3.18 (s, 6H), 1.84 (s, 3H), 1.04 (d, J=6.0 Hz, 3H), 0.84-0.706 (m, 2H), 0.54-0.44 (m, 1H), 0.34-0.26 (m, 1H). HRMS (ES, M+H) calcd. for $C_{25}H_{33}N_5O_3S$: 484.2377, found: 484.2390.

Use of the preferred enantiomer trans-S,S from Intermediate A, step B, affords the preparation of the preferred enantiopure S,S,R example.

EXAMPLE 41

N-(4-[2-(1R-amino-1-methyl-2-phenylethyl)-1,3thiazol-5-yl]-6-{methyl[(2-methylcyclopropyl)methyl]amino}pyridin-2-yl)-N-methylmethanesulfonamide (Scheme 14)

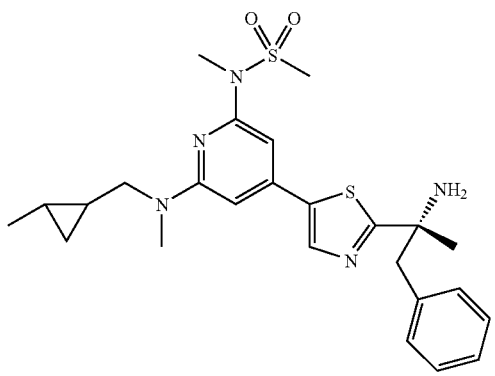

A solution of Intermediate G (50 mg, 0.08 mmol) and Lawson's reagent (134 mg, 0.33 mmol) in acetonitrile (0.8 mL) was irradiated under microwave (Smith Synthesizer) at 85° C. for 15 min and at 90° C. for 15 min (Boc was also removed in the same reaction), concentrated under a flow on $N_2$ and purified by preparative HPLC (5->95% $CH_3CN/H_2O$, 0.1% added TFA, C18 PRO YMC 20×150 mm) to provide N-(4-[2-(1R-amino-1-methyl-2-phenylethyl)-1,3-thiazol-5-yl]-6-{methyl[(2-methylcyclopropyl)methyl]amino}pyridin-2-yl)-N-methylmethanesulfonamide as a TFA salt. MS (ES, M+H) 500.

Use of the preferred enantiomer trans-S,S from Intermediate A, step B, affords the preparation of the preferred enantiopure S,S,R example.

EXAMPLE 42

N-(4-[2-(1R-amino-1-methyl-2-phenylethyl)-1,3imidazol-5-yl]-6-{methyl[(2-methylcyclopropyl)methyl]amino}pyridin-2-yl)-N-methylmethanesulfonamide (Scheme 14)

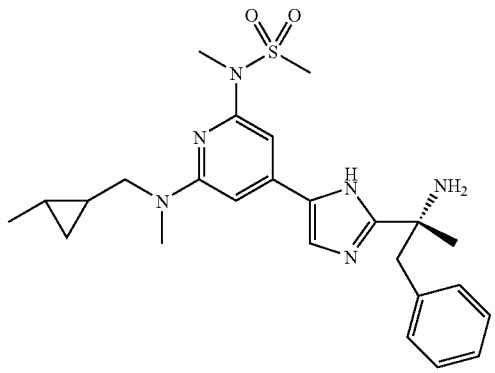

A mixture of Intermediate G (50 mg, 0.08 mmol) and ammonium acetate (64 mg, 0.83 mmol) was melted at 150° C. for 15 min (partial loss of Boc). The reaction mixture was allowed to cool to rt, diluted with saturated $NaHCO_3$, extracted with EtOAc (×3). The combined organic layer was washed with brine, dried over $Na_2SO_4$ and concentrated in vacuo. Boc removal with TFA in DCM (5 mL, 10% TFA in DCM), concentration in vacuo, purification by preparative HPLC (5->95% $CH_3CN/H_2O$, 0.1% added TFA, C18 PRO YMC 20×150 mm) and lyophilization provided N-(4-[2-(1R-amino-1-methyl-2-phenylethyl)-1,3-imidazol-5-yl]-6-{methyl[(2-methylcyclopropyl)methyl]amino}pyridin-2-yl)-N-methylmethanesulfonamide as a TFA salt. $^1$H NMR (400 MHz, $CD_3OD$) δ 7.76 (s, 1H), 7.29-7.21 (m, 3H), 7.06 (s, 2H), 6.92-6.86 (m, 2H), 3.66-3.56 (m, 1H), 3.48-3.35 (m, 1H), 3.41 (A of AB, d, J=13.6 Hz, 1H), 3.34 (s, 3H), 3.26 (B of AB, d, J=13.6 Hz, 1H), 3.18 (s, 3H), 3.16 (s, 3H), 1.74 (s, 3H), 1.04 (d, J=5.7 Hz, 3H), 0.85-0.70 (m, 2H), 0.51-0.45 (m, 1H), 0.31-0.25 (m, 1H). HRMS (ES, M+H) calcd. for $C_{25}H_{34}N_6O_2S$: 483.2537, found: 483.2548.

Use of the preferred enantiomer trans-S,S from Intermediate A, step B, affords the preparation of the preferred enantiopure S,S,R example.

EXAMPLE 43

N-(4-[5-(1R-amino-1-methyl-2-phenylethyl)-1,3-oxazol-2-yl]-6-{methyl[(2-methylcyclopropyl)methyl]amino}pyridin-2-yl)-N-methylmethanesulfonamide (Scheme 17)

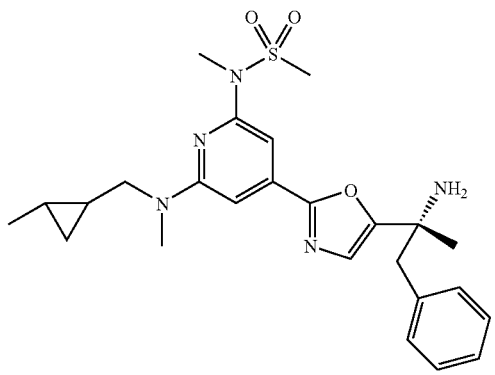

Example 43 was prepared from Intermediate H, using a similar procedure as described for the preparation of Example 7. ¹H NMR (400 MHz, CD₃OD) δ 7.32-7.26 (m, 3H), 7.22 (s, 1H), 7.14 (s, 1H), 7.06-6.99 (m, 3H), 3.62 (A of ABX, dd, J=14.4, 6.2 Hz, 1H), 3.45 (A of AB, d, J=13.7 Hz, 1H), 3.43 (B of ABX, dd, J=14.4, 2.3 Hz, 1H), 3.39 (s, 3H), 3.26 (B of AB, d, J=13.7 Hz, H), 3.18 (s, 3H), 3.16 (s, 3H), 1.73 (s, 3H), 1.04 (d, J=6.2 Hz, 3H), 0.86-0.70 (m, 2H), 0.52-0.44 (m, 1H), 0.30-0.24 (m, 1H). HRMS (ES, M+H) calcd. for $C_{25}H_{33}N_5O_3S$: 484.2377, found: 484.2374.

Use of the preferred enantiomer trans-S,S from Intermediate A, step B, affords the preparation of the preferred enantiopure S,S,R example.

EXAMPLE 44

N-[4-[5-(1R-amino-1-methyl-2-phenylethyl)-1,3oxazol-2-yl]-6-({1-[(1S,2S)-2-methylcyclopropyl]ethyl}amino)pyridin-2-yl]-N-methylmethanesulfonamide

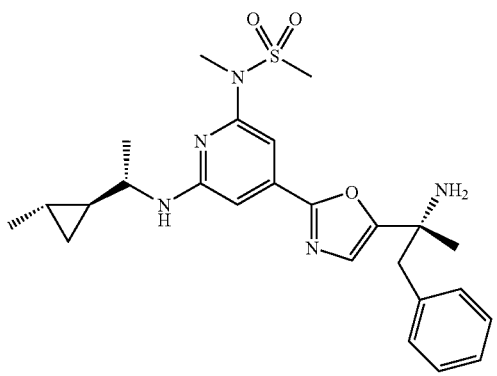

Step A. Pd Coupling

To a solution of (1S)-1-[(1S,2S)-2-methylcyclopropyl]ethanaminium chloride (intermediate P, 0.039 g, 0.29 mmol) and tert-butyl (1R)-1-(2-{2-chloro-6-[methyl(methylsulfonyl)amino]pyridin-4-yl}-1,3-oxazol-5-yl)-1-methyl-2-phenylethylcarbamate (intermediate k, 0.050 g, 0.10 mmol) in 1 mL DMF was added $K_3PO_4$ (0.122 g, 0.58 mmol) and Pd(PtBu₃)₂ (0.007 g, 0.01 mmol). After 16 h at ambient temperature, the sealed reaction was heated at 110° C. for 8.5 h and then filtered over a pad of celite. The celite was washed with EtOAc (60 mL). The filtrate was concentrated in vacuo and the resulting residue taken up in DMF and purified by reverse phase LC. The resulting material was diluted with EtOAc (40 mL) and washed with saturated sodium bicarbonate solution (20 mL). The aqueous layer was back extracted with EtOAc (20 mL). The combined organics were washed with brine (20 mL), dried over $Na_2SO_4$, filtered and concentrated in vacuo to give 0.028 g (50%) of tert-butyl (1R)-1-methyl-1-(2-{2-({(1S)-1-[(1S,2S)-2-methylcyclopropyl]ethyl}amino)-6-[methyl(methylsulfonyl)amino]pyridin-4-yl}-1,3-oxazol-5-yl)-2-phenylethylcarbamate as a yellow residue. (CDCl₃, 400 MHz) 7.28 (m 3H); 7.06 (d, J=0.91 Hz, 1H); 7.03 (m, 2H); 6.93 (s, 1H); 6.76 (s, 1H); 3.50 (m, 1H); 3.36 (m, 4H); 14 (m, 4H); 1.60 (s, 3H); 1.42 (s, 9H); LC/MS [M+H]⁺=584.

Step B. Boc Removal $HCl_{(g)}$ was bubbled through a 0° C. solution of tert-butyl (1R)-1-methyl-1-(2-{2-({(1S)-1-[(1S,2S)-2-methylcyclopropyl]ethyl}amino)-6-[methyl(methylsulfonyl)amino]pyridin-4-yl}-1,3-oxazol-5-yl)-2-phenylethylcarbamate (0.028 g, 0.05 mmol) in 1 mL $CH_2Cl_2$ for 5 min. After 10 min at 0° C., the reaction was concentrated in vacuo and taken up in DMF. Purification by reverse phase LC followed by lyophilization yielded (2R)-2-(2-{2-({(1S)-1-[(1S,2S)-2-methylcyclopropyl]ethyl}amino)-6-[methyl(methylsulfonyl)amino]pyridin-4-yl}-1,3-oxazol-5-yl)-1-phenylpropan-2-aminium as a white solid. (CDCl₃, 400 MHz) 7.27 (m, 3H); 7.19 (s, 1H); 7.01 (m, 3H); 6.89 (d, J=0.92 Hz, 1H); 3.53 (m, 1H); 3.45 (d, J=13.37 Hz, 1H); 3.33 (s, 3H); 3.24 d, J=13.55 Hz, 1H); 3.14 (s, 3H); 1.71 (s, 3H); 1.27 (d, J=6.41 Hz, 3H); 1.94 (d, J=5.67 Hz, 3H); 0.66 (m, 2H); 0.53 (m, 1H); 0.20 (m, 1H); LC/MS [M+H]⁺=484.

Additional oxazole derivatives were prepared as described below in Table 3.

TABLE 3

Oxazole Derivatives

| Ex. # | intermediate | Mode of prep | structure | ES M + 1 |
|---|---|---|---|---|
| 45 | (structure) | See ex 10 | (structure) | 560 |

TABLE 3-continued

Oxazole Derivatives

| Ex. # | intermediate | Mode of prep | structure | ES M + 1 |
|---|---|---|---|---|
| 46 | | Ex 42, debenzylation | 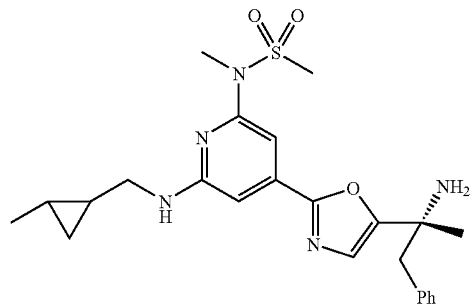 | 470 |
| 47 | | See ex 42 | 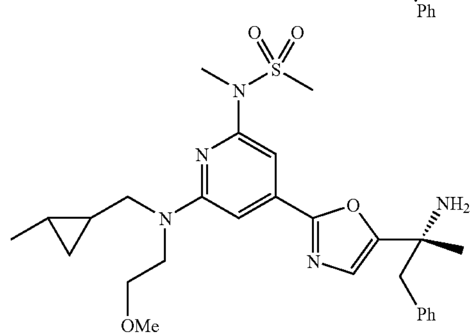 | 528 |
| 48 | Intermediate k | intermediate Q, see Ex. 43 | 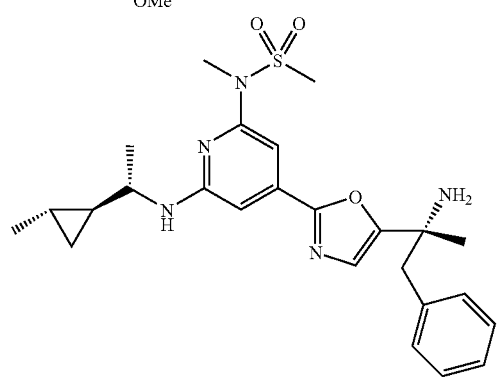 | 484 |

EXAMPLE 49

N-(4-[5-(1R-amino-1-methyl-2-phenylethyl)-1,3thiazol-2-yl]-6-{methyl[(2-methylcyclopropyl)methyl]amino}pyridin-2-yl)-N-methylmethanesulfonamide (Scheme 17)

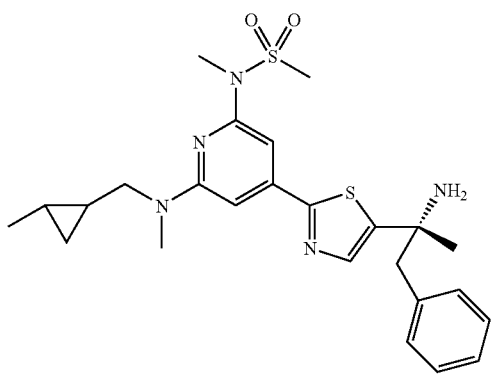

Example 49 was prepared from Intermediate H, using a similar procedure as described for the preparation of Example 8. 1H NMR (400 MHz, CD$_3$OD) δ 7.55 (s, 1H), 7.26-7.20 (m, 3H), 7.05-7.00 (m, 2H), 6.99 (d, J=1.2 Hz, 1H), 6.90 (d, J=1.2 Hz, 1H), 3.59 (A of ABX, dd, J=14.4, 6.4 Hz, 1H), 3.42 (B of ABX, dd, J=14.4, 6.8 Hz, 1H), 3.37 (s, 3H), 3.17 (s, 3H), 3.15 (s, 3H), 3.09 (s, 2H), 1.60 (s, 3H), 1.04 (d, J=6.0 Hz, 3H), 0.85-0.68 (m, 2H), 0.50-0.42 (m, 1H), 0.29-0.21 (m, 1H). HRMS (ES, M+H) calcd. for C$_{25}$H$_{33}$N$_5$O$_2$S$_2$: 500.2149, found: 500.2149.

Use of the preferred enantiomer trans-S,S from Intermediate A, step B, affords the preparation of the preferred enantiopure S,S,R example.

EXAMPLE 50

N-(4-[5-(1R-amino-1-methyl-2-phenylethyl)-4H-1,2,4-triazol-3-yl]-6-{methyl[(2-methylcyclopropyl)methyl]amino}pyridin-2-yl)-N-methylmethanesulfonamide (Scheme 11)

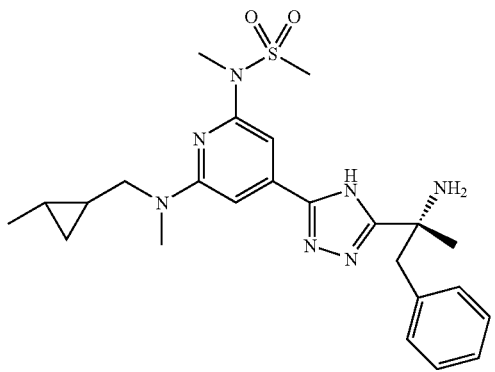

A solution of Intermediate I (17 mg, 0.06 mmol), Intermediate J (20 mg, 0.05 mmol) and diisopropylethyl amine (0.013 mL, 0.08 mmol) in EtOH (1 mL) was sealed and heated to 150° C. for 2 days. The reaction mixture was concentrated in vacuo and purified preparative HPLC (5->95% CH$_3$CN/H$_2$O, 0.1% added TFA, C18 PRO YMC 20×150 nm n) to provide N-(4-[5-(1R-amino-1-methyl-2-phenylethyl)-4H-1,2,4-triazol-3-yl]-6-{methyl[(2-methylcyclopropyl)methyl]amino}pyridin -2-yl)-N-methylmethanesulfonamide as the TFA salt. $^1$H NMR (400 MHz, CD$_3$OD) δ 7.30-7.22 (m, 3H), 7.13 (s, 1H), 7.04 (s, 1H), 7.02-6.96 (m, 2H), 3.65-3.56 (m, 1H), 3.48-3.42 (m, 1H), 3.38 (s, 3H), 3.36 (s, 2H), 3.18 (s, 3H), 3.17 (s, 3H), 1.78 (s, 3H), 1.04 (d, J=6.0 Hz, 3H), 0.86-0.70 (m, 2H), 0.52-0.44 (m, 1H), 0.30-0.23 (m, 1H).

Use of the preferred enantiomer trans-S,S from Intermediate A, step B, affords the preparation of the preferred enantiopure S,S,R example.

EXAMPLE 51

N-(4-[5-(1-aminoethyl)-1,3,4-oxadiazol-2-yl]-6-{methyl[(2-methylcyclopropyl)methyl]amino}pyridin-2-yl)-N-methylmethanesulfonamide (Alt. Scheme 8)

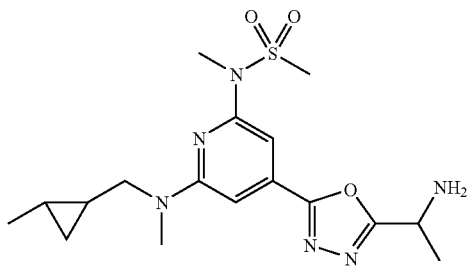

Step A: Coupling

To a solution of Intermediate I (0.610 g, 1.614 mmol) and N-Boc-alanine (0.336 g, 1.78 mmol) in 10 mL DMF was added Hunig's base (0.564 mL, 3.23 mmol), EDC (0.371 g, 1.94 mmol) and HOAt (0.025 g, 0.161 mmol). After 15 h, the reaction was diluted with 3M LiCl and EtOAc, and the layers were separated. The aqueous layer was washed with EtOAc (2×), the combined organics were washed with 3M LiCl (2×) and brine, dried over Na$_2$SO$_4$, filtered and concentrated. The residue was purified by normal phase chromatography (35->90% EtOAc/hexanes) to afford the desired coupled adduct as a yellow foam. $^1$H NMR (CDCl$_3$, 400 MHz) δ 9.11 (br s, 1H), 8.97 (br s, 1H), 8.00 (s, 1H), 6.76 (s, 1H), 6.69 (s, 1H), 5.09 (d, J=7.5 Hz, 1H), 3.47 (dd, J=14.5, 6.2, 1H), 3.32 (s, 3H), 3.29 (dd, J=14.5, 7.0 Hz, 1H), 3.07 (s, 3H), 2.93 (s, 3H), 1.43 (s, 9H), 1.41 (d, J=7.5 Hz, 3H), 1.00 (d, J=5.7 Hz, 3H), 0.68 (m, 1H), 0.62 (m, 1H), 0.36 (m, 1H), 0.23 (m, 1H); LCMS [M+H]$^+$=513.

Step B: Dehydration

To a solution of product from Step A (0.763 g, 1.49 mmol) in 7 mL 1,2-dichloroethane was added Burgess reagent (1.42 g, 5.95 mmol). The slurry was microwaved at 120° C. for 10 min, then poured directly on top of a silica gel column for normal phase purification (10->55% EtOAc/hexanes). The desired product was obtained as a yellow foam. $^1$H NMR (CDCl$_3$, 400 MHz) δ 7.01 (s, 1H), 6.93 (s, 1H), 5.12 (m, 1H), 3.52 (dd, J=14.5, 6.3 Hz, 1H), 3.38 (s, 3H), 3.33 (dd, J=14.5, 7.0 Hz, 1H), 3.15 (s, 3H), 3.11 (s, 3H), 1.63 (d, J=6.8 Hz, 3H), 1.44 (s, 9H), 1.01 (d, J=4.9 Hz, 3H), 0.73 (m, 1H), 0.67 (m, 1H), 0.41 (m, 1H), 0.26 (m, 1H); LCMS [M+H]$^+$=495.

Step C: Deprotection

HCl was bubbled through a solution of product from Step B (0.532 g, 1.08 mmol) in 15 mL EtOAc at 0° C. for 5 min. The bright yellow solution was warmed to rt for 1 h, then concentrated to afford N-(4-[5-(1-aminoethyl)-1,3,4-oxadiazol-2-yl]-6-{methyl[(2-methylcyclopropyl)methyl]amino}pyridin-2-yl)-N-methylmethanesulfonamide as a yellow foam which was used without further purification. $^1$H NMR (d$_4$-MeOH, 400 MHz) δ 7.15 (s, 1H), 7.05 (s, 1H), 4.95 (q, J=7.0 Hz, 1H), 3.61 (dd, J=14.5, 8.1 Hz, 1H), 3.43 (dd, J=14.5, 6.9 Hz, 1H), 3.38 (s, 3H), 3.16 (s, 3H), 3.15 (s, 3H), 1.79 (d, J=7.0 Hz, 3H), 1.01 (d, J=5.8 Hz, 3H), 0.82-0.75 (m, 2H), 0.47 (m, 1H), 0.25 (m, 1H); LCMS [M+H]$^+$=395.

Use of the preferred enantiomer trans-S,S from Intermediate A, step B, affords the preparation of the preferred enantiopure S,S,R example.

EXAMPLE 52

N-(4-[5-(1-amino-1-methyl-2-pyridin-4-ylethyl)-1,3,4-oxadiazol-2-yl]-6-{[(2-methylcyclopropyl)methyl]amino}pyridin-2-yl)-N-methylmethanesulfonamide (Alt. Scheme 8)

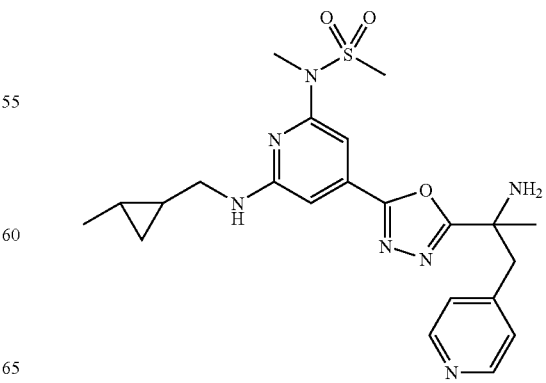

N-(4-[5-(1-amino-1-methyl-2-pyridin-4-ylethyl)-1,3,4-oxadiazol-2-yl]-6-{[(2-methylcyclopropyl)methyl]amino}pyridin-2-yl)-N-methylmethanesulfonamide was prepared from Intermediate III and intermediate 1 using a procedure similar to that described in Example 70. $^1$H NMR (d$_4$-MeOH) δ 8.77 (d, J=6.0 Hz, 2H), 7.78 (d, J=6.4 Hz, 2H), 6.96 (d, J=11.7 Hz, 2H), 3.78 (app ABX, J$_{AB}$, J$_{AX}$, J$_{BX}$=13.5 Hz, 2H), 3.37 (s, 3H), 3.24 (d, J=6.8 Hz, 2H), 3.16 (s, 3H), 1.94 (s, 3H), 1.06 (d, J=6.0, 3H), 0.87-0.81 (m, 1H), 0.72-0.66 (m, 1H), 0.43 (dt, J=8.7, 4.6 Hz, 1H), 0.26 (dt, J=8.6, 4.8 Hz, 1H). HRMS (ES, M+H) calcd for C$_{22}$H$_{29}$N$_7$O$_3$S: 472.2126, found: 472.2163.

Use of the preferred enantiomer trans-S,S from Intermediate A, step B, affords the preparation of the preferred enantiopure S,S,R example.

TABLE IV

Oxadiazole Derivates

| Ex # | intermediate | Mode of prep |
|---|---|---|
| 53 | 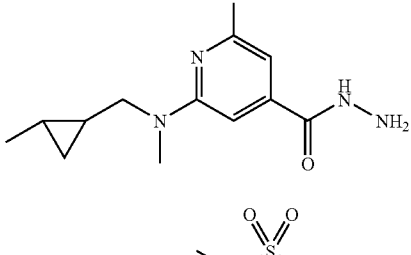 | See ex 51 |
| 54 | 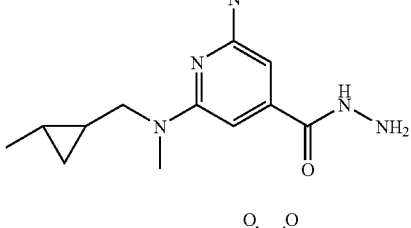 | See ex 51 |
| 55 | 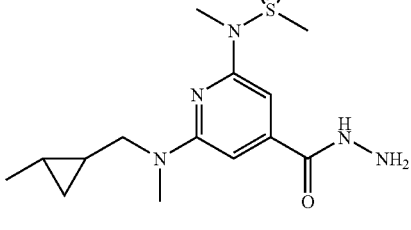 | See ex 51 |
| 56 | 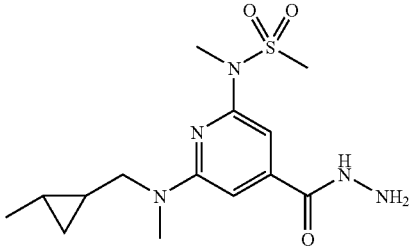 | See ex 51 |
| 57 | 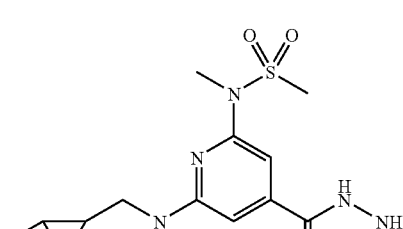 | See ex 51 |

TABLE IV-continued
| | | |
|---|---|---|
| 58 | 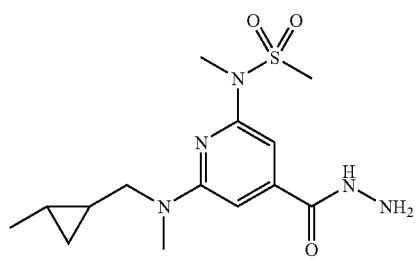 | See ex 51 |
| 59 | 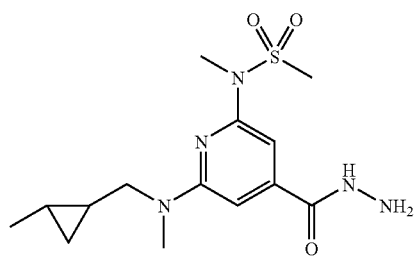 | See ex 51 |
| 60 | 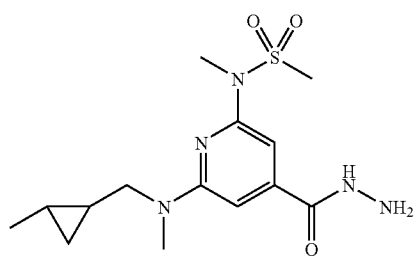 | See ex 51 |
| 61 | 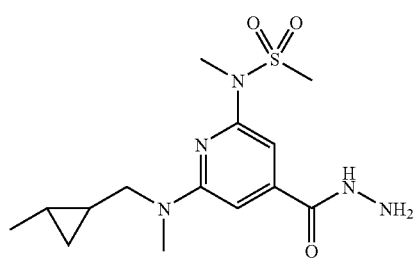 | See ex 51 |
| 62 | 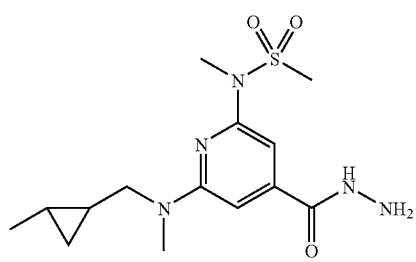 | See ex 51 |
| 63 | 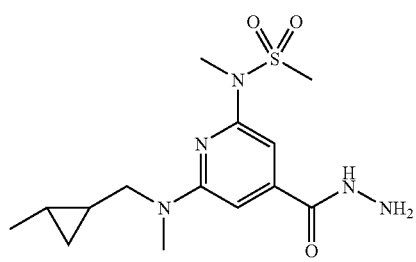 | See ex 51 |

TABLE IV-continued
| | | |
|---|---|---|
| 64 | 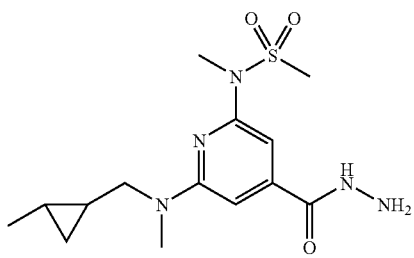 | Intermediate IV, See ex 51 |
| 65 | 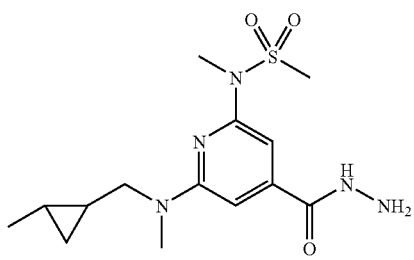 | See ex 51 |
| 66 | 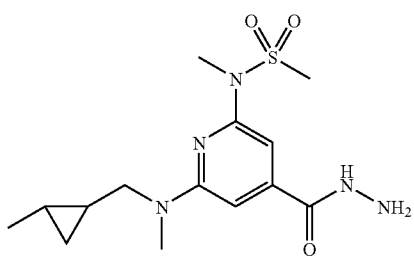 | See ex 51 |
| 67 | 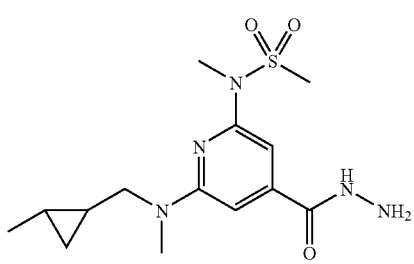 | See ex 51 |
| 68 | 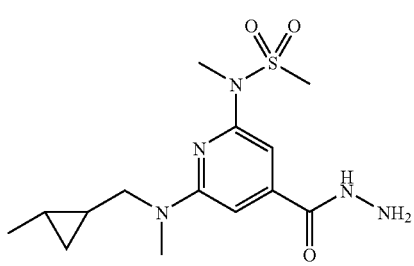 | See ex 51 |
| 69 | 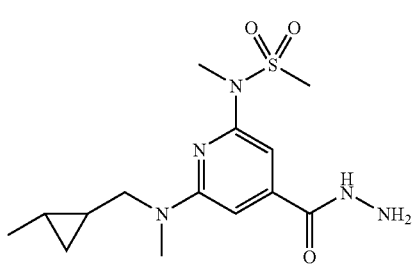 | See ex 51 |

TABLE IV-continued
| 70 | 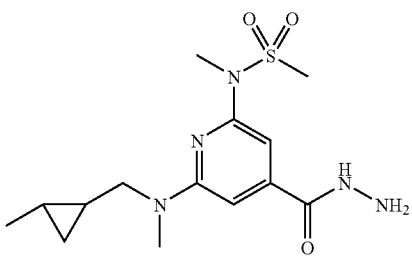 | See ex 51 |
| --- | --- | --- |
| 71 | 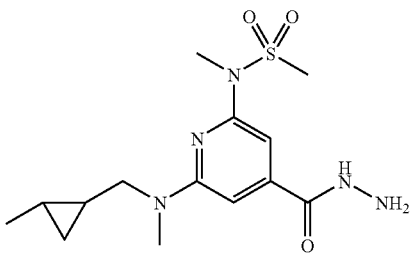 | See ex 51 |
| 72 | 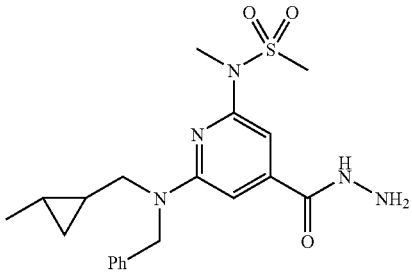 | See ex 51 |
| 73 | See ex 71 | Debenzylation |
| 74 | 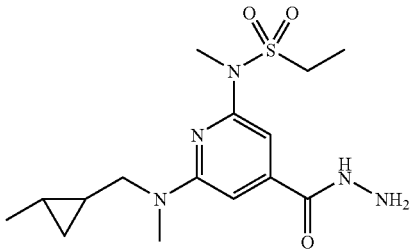 | See ex 51 |
| 75 | 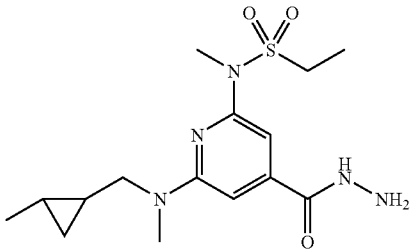 | See ex 51 |
| 76 | 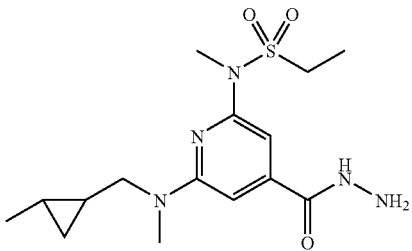 | See ex 51 |

TABLE IV-continued
| 77 | 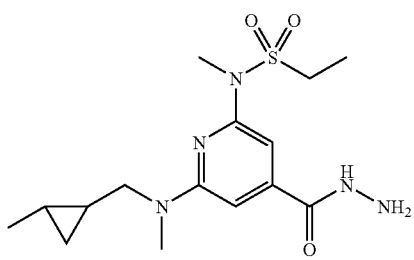 | See ex 51 |
| --- | --- | --- |
| 78 | 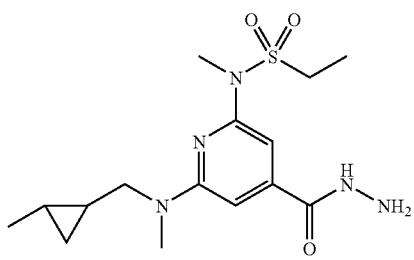 | See ex 51 |
| 79 | 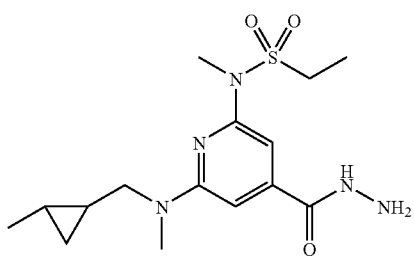 | See ex 51 |
| 80 | 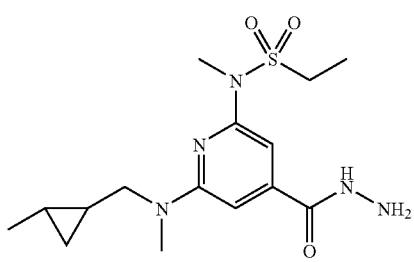 | See ex 51 |
| 81 | 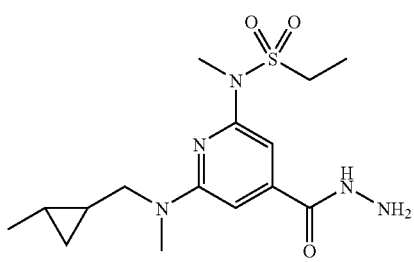 | See ex 51 |
| 82 | 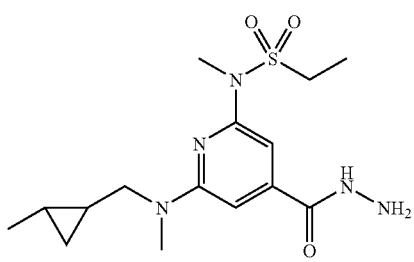 | See ex 51 |

TABLE IV-continued
| | | |
|---|---|---|
| 83 | 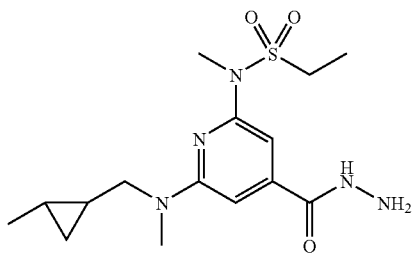 | See ex 51 |
| 84 | 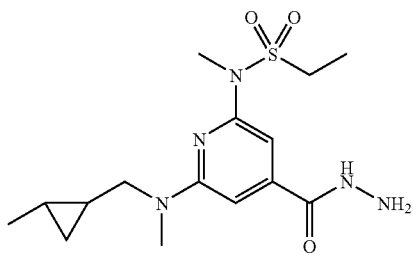 | See ex 51 |
| 85 | 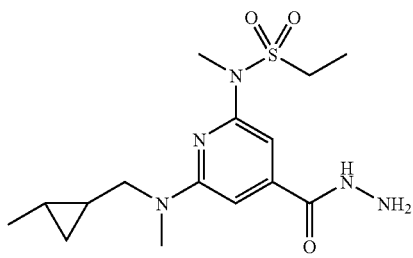 | See ex 51 |
| 86 | 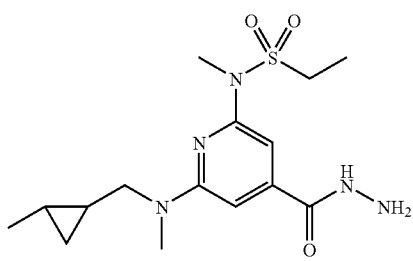 | See ex 51 |
| Ex # | Structure | ES M + 1 |
|---|---|---|
| 53 | 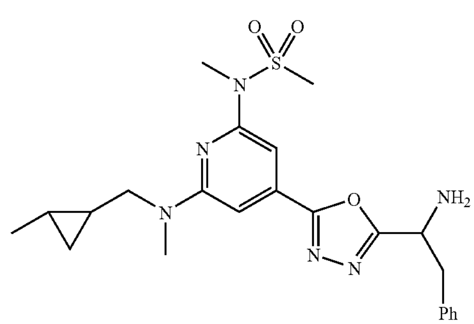 | 471 |

TABLE IV-continued
| | | |
|---|---|---|
| 54 | 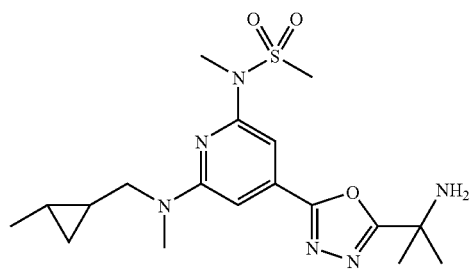 | 409 |
| 55 | 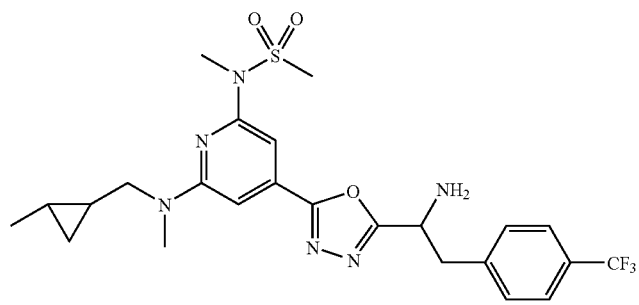 | 539 |
| 56 | 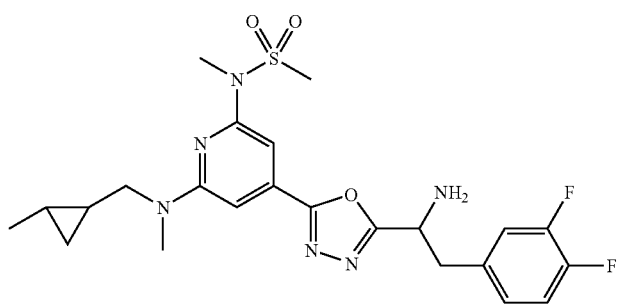 | 507 |
| 57 | 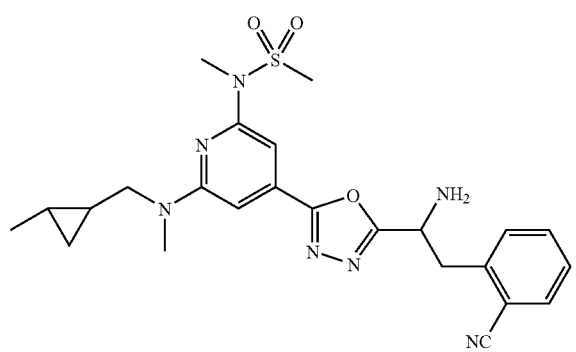 | 496 |
| 58 | 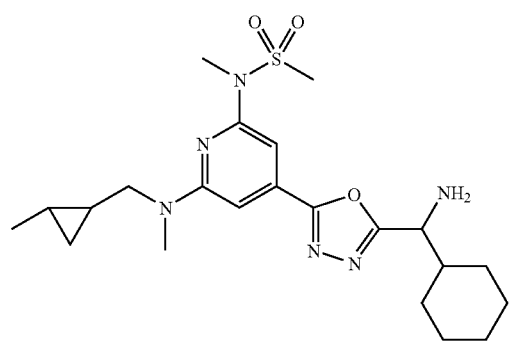 | 463 |

TABLE IV-continued
| | | |
|---|---|---|
| 59 | 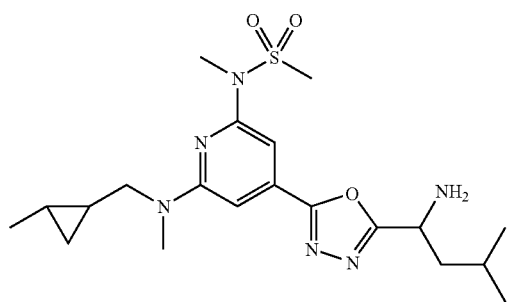 | 437 |
| 60 | 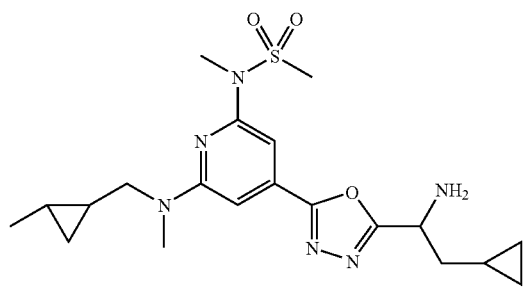 | 435 |
| 61 | 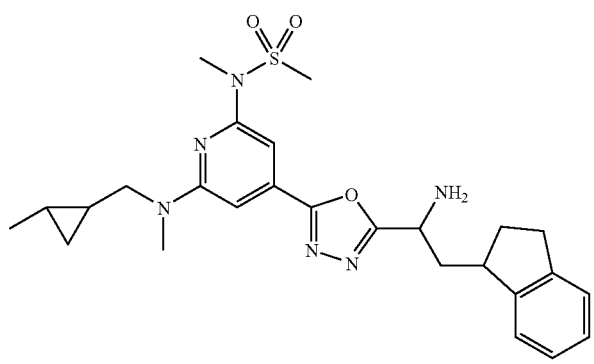 | 497 |
| 62 | 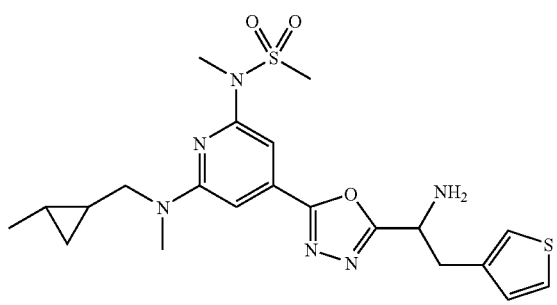 | 477 |
| 63 | 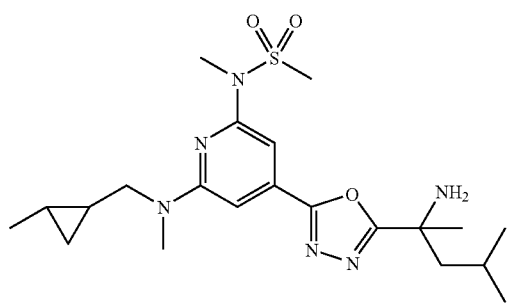 | 451 |

TABLE IV-continued
| 64 | 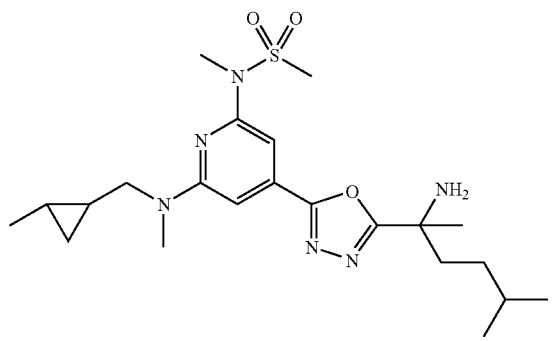 | 465 |
| 65 | 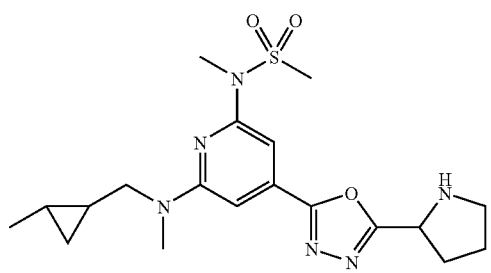 | 421 |
| 66 | 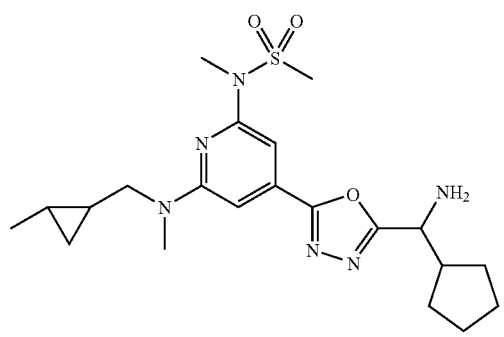 | 449 |
| 67 | 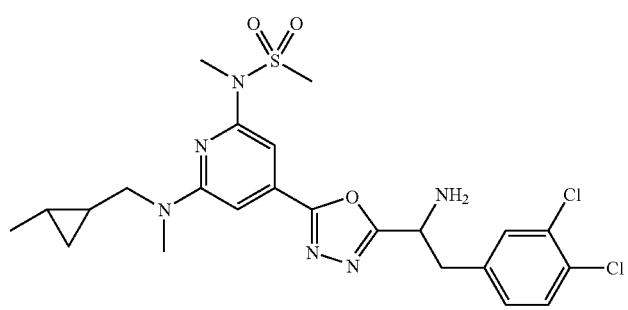 | 539 |
| 68 | 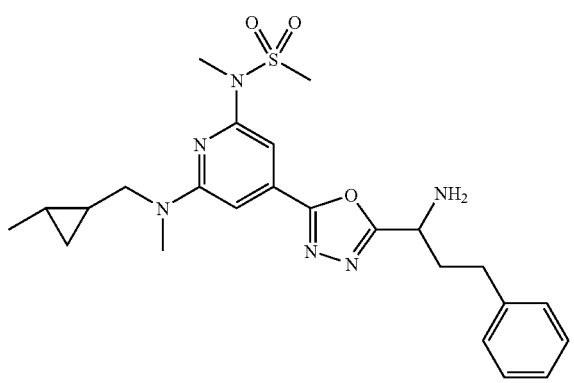 | 485 |

TABLE IV-continued
| | | |
|---|---|---|
| 69 | 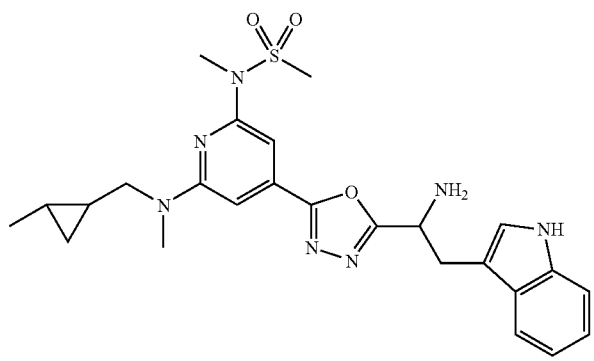 | 510 |
| 70 | 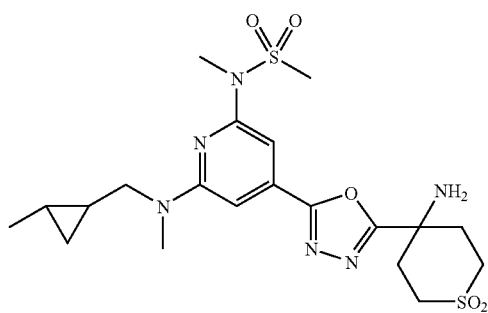 | 499 |
| 71 | 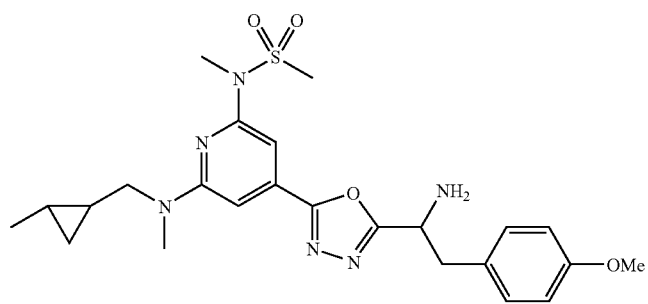 | 515 |
| 72 | 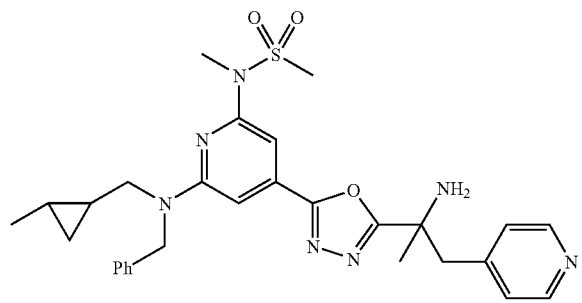 | 562 |
| 73 | 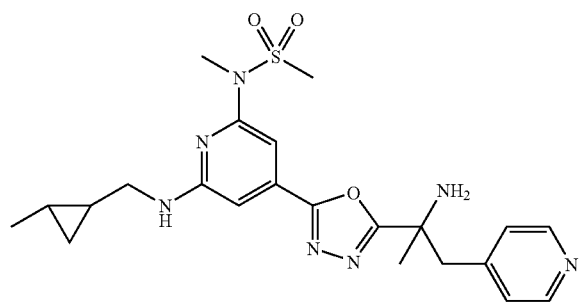 | 472 |

TABLE IV-continued
| 74 | 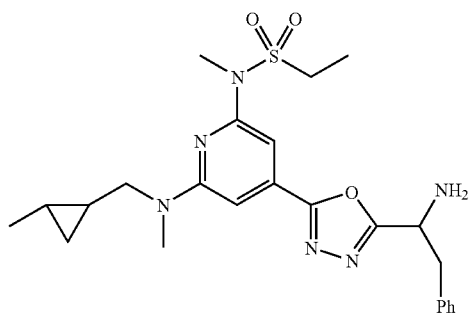 | 485 |
| 75 | 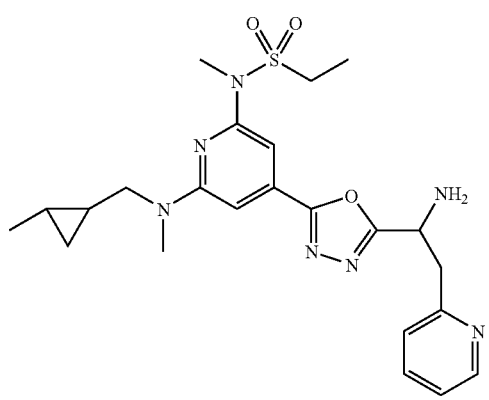 | 486 |
| 76 | 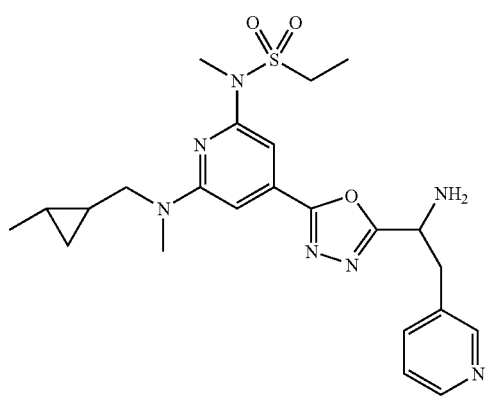 | 486 |
| 77 | 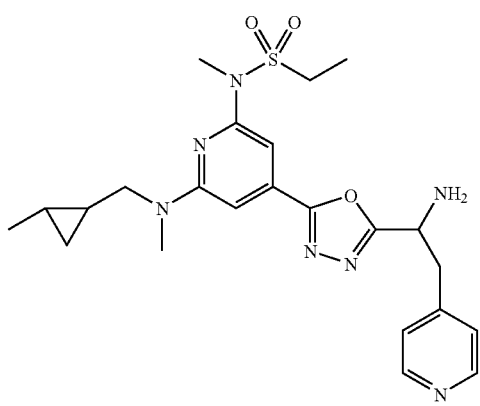 | 486 |

TABLE IV-continued
| 78 | 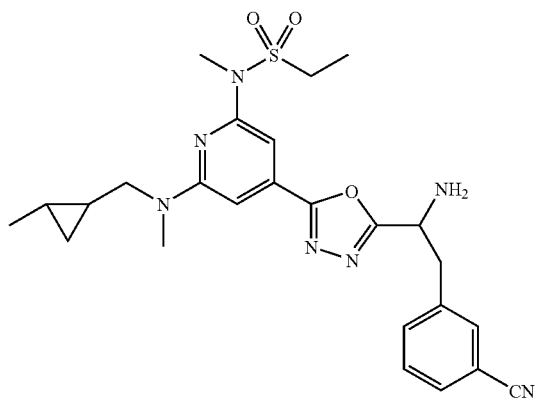 | 510 |
| 79 | 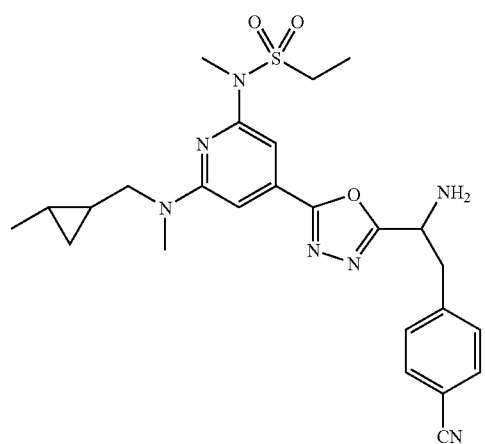 | 510 |
| 80 | 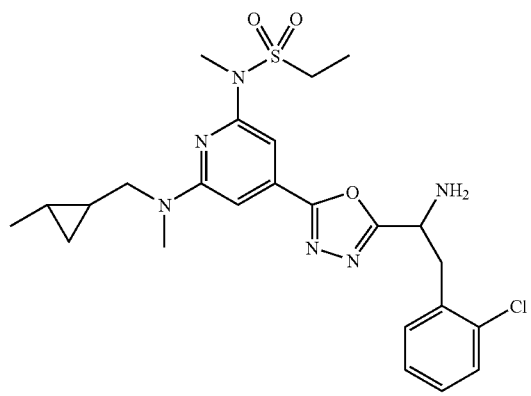 | 519 |
| 81 | 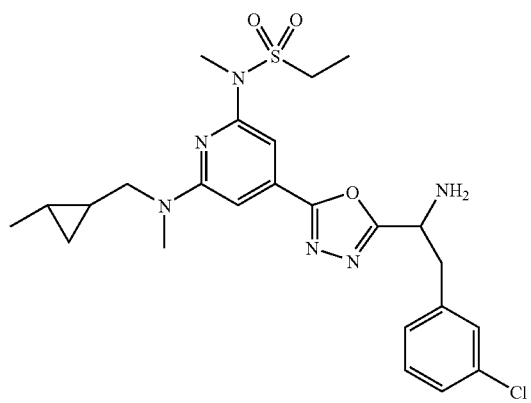 | 519 |

TABLE IV-continued
| 82 | 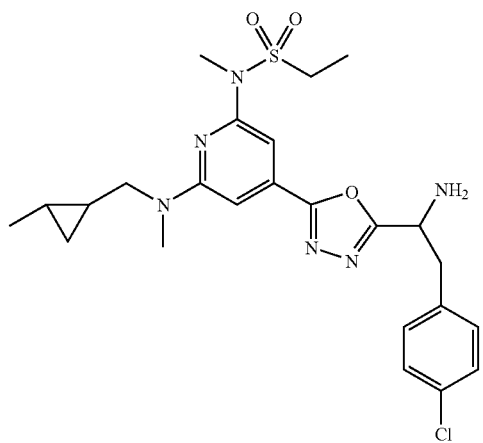 | 519 |
| 83 | 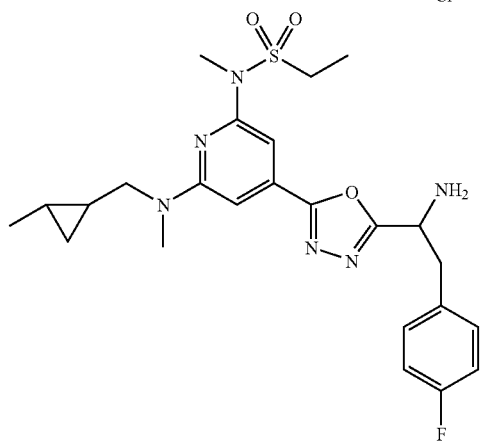 | 503 |
| 84 | 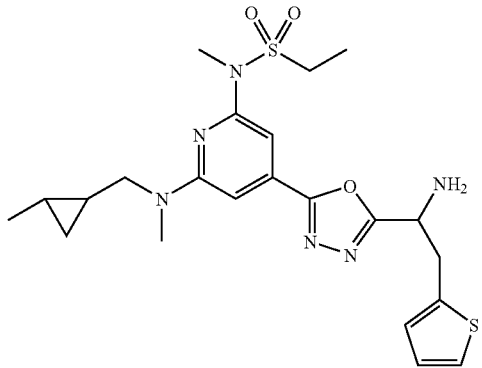 | 491 |
| 85 | 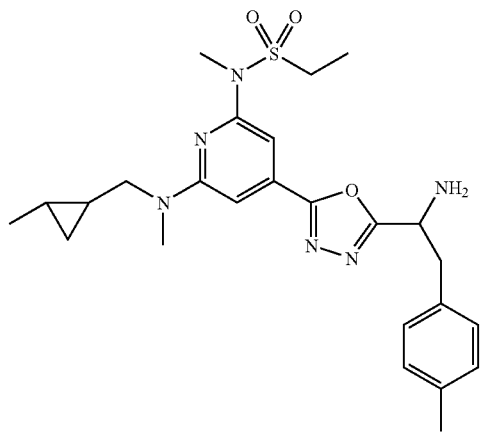 | 499 |

TABLE IV-continued

86 | 492

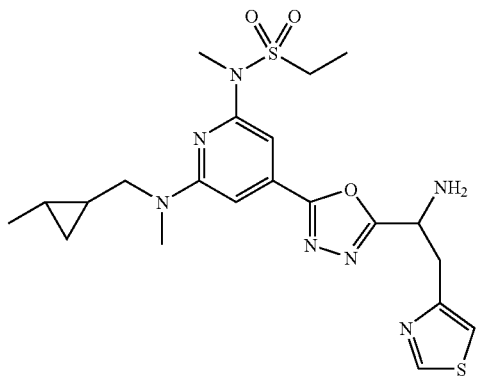

EXAMPLE 87

N-(4-[5-(1-amino-1-methyl-2-(4-fluorophenyl)lethyl)-1,3,4-oxadiazol-2-yl]-6-{methyl[(2-methylcyclopropyl)methyl]amino}pyridine-2-yl)-N-methyl-methanesulfonamide (Alt. Scheme 8, 2$^{nd}$ line)

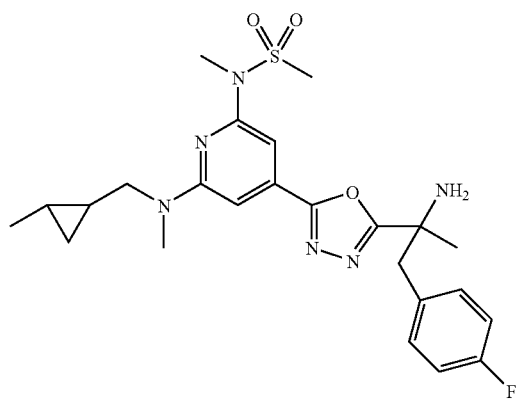

To a solution of Intermediate m (0.051 g, 0.091 mmol) in 0.80 mL DMF at 0° C. was added 1M NaHMDS in THF (0.13 mL, 1.30 mmol), and the reaction turned deep blue. After 5 min, 4-fluorobenzyl bromide as a 1M solution in DMF (0.180 mL, 0.180 mmol) was added via syringe, and the reaction went yellow when the addition was complete. After 30 min, 0.125 mL H$_2$O and 0.025 mL 1H HCl was added. After 1.5 h, 0.125 mL 1N HCl was added, and the reaction was allowed to proceed for 15 h, then loaded onto an SCX ion exchange cartridge, which was eluted with MeOH, followed by 2M NH$_3$ in MeOH. Impure desired product was isolated from the basic fractions, which was further purified by preparative HPLC (5->95% CH$_3$CN/H$_2$O over 30 min, 0.1% added TFA, C18 PRO YMC 20×150 mm) to afford N-(4-{5-[1-amino-2-(4-fluorophenyl)-1-methylethyl]-1,3,4-oxadiazol-2-yl}-6-{methyl[(2-methylcyclopropyl)methyl]amino}pyridin-2-yl)-N-methylmethanesulfonamide as a flocculent yellow solid after lyophilization. $^1$H NMR (d$_4$-MeOH, 400 MHz) δ 7.12-7.03 (m, 5H), 6.91 (s, 1H), 3.59 (dd, J=14.8, 6.2 Hz, 1H), 3.43-3.39 (m, 3H), 3.31 (s, 3H), 3.16 (s, 3H), 3.15 (s, 3H), 1.84 (s, 3H), 1.02 (d, J=6.0 Hz, 3H), 0.80-0.70 (m, 2H), 0.46 (m, 1H), 0.26 (m, 1H); High resolution mass spec (FT/ICR) calc M+H=503.2235 found 503.2279. Use of the preferred enantiomer trans-S,S from Intermediate A, step B, affords the preparation of the preferred enantiopure S,S,R example.

Additional oxadiazole derivatives were prepared as described below in Table 5.

TABLE 5

Oxadiazole Derivatives

| Ex # | intermediate | Mode of prep |
|---|---|---|
| 88 | 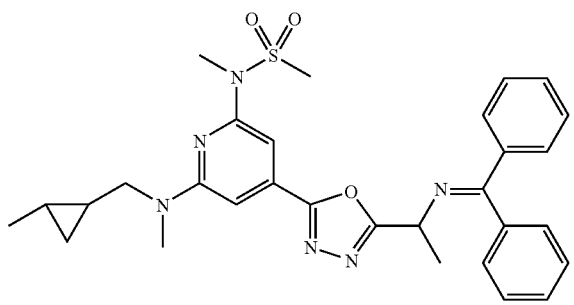 | Ex 87 |

TABLE 5-continued
| | | |
|---|---|---|
| 88 | 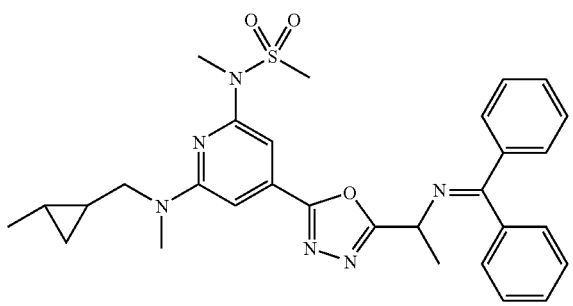 | Ex 87, tert-butyl [4-(bromomethyl)pyridin-2-yl]carbamate, Boc removal |
| 90 | 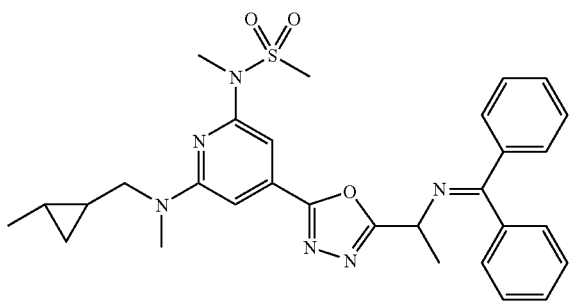 | Ex 87, (1-bromoethyl)benzene |
| Ex # | structure | ES M + 1 |
|---|---|---|
| 88 | | 501 |
| 88 | | 501 |
| 90 | 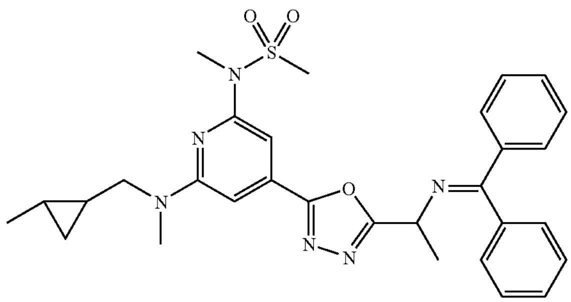 | 499 |

EXAMPLE 91

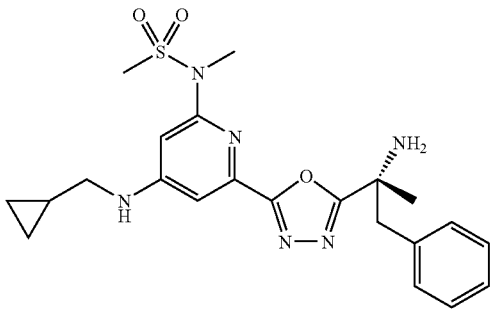

Step A:

4-Amino 2,6-dichloropyridine (2.0 g, 12.2 mmol) was suspended in toluene (50 mL) to which was added benzaldehyde (6.24 mL, 30.7 mmol). The reaction was heated to reflux for 12 h and water was collected using a Dean-Stark apparatus. The solvent was then removed in vacuo. The residue was dissolved in ethanol (25 mL) and heated to 50° C. NaBH$_4$ (1.86 g, 61 mmol) was added portionwise. The reaction was then heated to 75° C. for 2 h. The solvent was removed in vacuo, water (100 mL) was added and the solution was extracted with EtOAc (3×100 mL). The combined organic layer were washed with brine (1×100 mL), dried over MgSO$_4$, filtered, and concentrated. Purification by silica gel chromatography (20% EtOAc/Hex) afforded the benzyl aniline (2.93 g, 94%).

LCMS [M+H]=253.1

$^1$H NMR (CDCl$_3$) δ 7.40-7.14 (m, 5H), 6.46 (s, 2H), 4.35 (d, J=5.5 Hz, 2H)

Step B:

To a solution of the aniline from step A (0.079 g, 0.31 mmol) was added bromomethylcyclopropane (0.05 g, 0.37 mmol) followed by NaH (60% dispersion, 0.014 g, 0.37 mmol). The solution was stirred at rt for 30 min, then quenched with H$_2$O. The solution was extracted with EtOAc (3×30 mL) after which the combined organic layers were dried over MgSO$_4$, filtered and concentrated. Purification by silica gel chromatography (15% EtOAc/Hex) affored the cyclopropyl methyl aniline (0.078 g, 81%).

LCMS [M+H]=307.1

$^1$HNMR (CDCl$_3$) δ 7.36-7.13 (m, 5H), 6.51 (s, 2H), 4.64 (s, 2H), 3.29 (d, J=6.6 Hz, 2H), 1.08-1.6 (m, 1H), 0.60-0.55 (m, 2H), 0.24-0.21 (m, 2H)

Step C:

A dioxane solution (2 mL) of dichloropyridine from step B (0.078 g, 0.25 mmol), N-methyl methyl sulfonamide (0.033 g, 0.30 mmol), K$_3$PO$_4$ (0.075 g, 0.35 mmol), and Xanphos (0.01 g, 0.17 mmol) was degassed via argon purge for 15 min. Pd$_2$(dba)$_3$ (0.005 g, 0.05 mmol) was added and the solution was heated to 100° C. for 12 h. The solution was cooled and diluted with H$_2$O (30 mL). The solution was extracted with EtOAc (3×30 mL) and the combined organic layers were dried over MgSO$_4$, filtered, and concentrated. Purification by silica gel chromatography (20% EtOAc/Hex) affored the desired sulfonamide (0.034 g, 35%).

LCMS [M+H]=380.3

$^1$H NMR (CDCl$_3$) δ 7.35-7.19 (m, 3H), 7.16 (d, J=7.1 Hz, 2H), 6.68 (s, 1H), 6.46 (s, 1H), 4.62 (s, 2H), 3.31 (d, J=6.5 Hz, 2H), 3.29 (s, 3H), 2.93 (s, 3H), 1.12-1.08 (m, 1H), 0.58-0.55 (m, 2H), 0.24-0.21 (m, 2H).

Step D: To a solution of the sulfonamide from step C in DMF (4 mL) was added zinc cyanide (0.17 g, 1.45 mmol) followed by Pd(PPh$_3$)$_4$ (0.017 g, 0.15 mmol). The solution was heated to 85° C. for 48 h. The reaction mixture was diluted with H$_2$O (30 mL) and extracted with EtOAc (3, ×30 mL). The combined organic layers were washed with brine (1×50 mL), dried over MgSO$_4$, filtered, and concentrated. Purification by silica gel chromatography (30% EtOAc/Hex) afforded the cyanopyridine (0.27 g, 81%).

LCMS [M+H]=371.1

$^1$H NMR (CDCl$_3$) δ 7.36-7.26 (m, 3 H), 7.15 (d, J=7.2 Hz, 2H), 6.87 (s, 1H), 6.82 (s, 1H), 4.68 (s, 2H), 3.36 (d, J=6.5 Hz, 2H), 3.30 (s, 3H), 2.92 (s, 3H), 1.12-1.09 (m, 1H), 0.61 (d, J=7.6 Hz, 2H), 0.27 (d, J=4.9 Hz, 2H).

Step E: To a solution of the cyanopyridine from step D (0.15 g, 0.41 mmol) in 9:1 EtOH/H$_2$O (10 mL) was added solid KOH (0.26 g, 4.1 mmol). The solution was heated to 85° C. for 16 h. The solution was cooled, acidified with 1N HCl, and extracted with EtOAc (3×30 mL). The combined organics layers were washed with brine (1×50 mL), dried over MgSO$_4$, filtered and concentrated. The residue was used without further purification. To a solution of the carboxylic acid in DCM (5 mL) was added hydrazinylphenylalanine (0.16 g, 0.59 mmol), DIPEA (0.023 g, 1.78 mmol) and BOP reagent (0.25 g, 0.59 mmol). The reaction was stirred at rt for 1 h followed by purification by silica gel chromatography (5% MeOH/chloroform) to afford the diketohydrazine (0.30 g, 77%)

LCMS [M+H]=665.1

$^1$H NMR (CDCl$_3$) δ 7.41-7.16 (m, 11H), 6.83 (s, 1H), 4.72 (s, 2H), 3.57 (d, J=14 Hz, 1H), 3.39 (d, J=6.6 Hz, 2H), 3.35 (s, 3H), 3.10 (d, J=14 Hz, 1H), 2.91 (s, 3H), 1.50 (s, 9H), 1.45 (s, 3H), 1.13-1.10 (m, 1H), 0.59-0.55 (m, 2H), 0.25 (d, J=5.0 Hz, 2H).

Step F: To a 1,2-dichloroethane solution (3 mL) of the diketohydrazine from step E (0.30 g, 0.46 mmol) was added burgess reagent (0.33 g, 1.4 mmol). The solution was microwaved at 120° C. for 8 min. Purification by silica gel chromatography afforded the desired oxadiazole (0.29 g, 62%)

LCMS [M+H]=647.1

$^1$H NMR (CDCl$_3$) δ 7.39-7.04 (m, 11H), 6.75 (s, 1H), 4.73 (s, 2H), 3.54-3.48 (m, 2H), 3.41 (d, J=6.6 Hz, 2H), 3.34 (s, 3H), 3.03 (s, 3H), 1.72 (br s, 3H), 1.41 (br s, 9H), 1.24-1.13 (m, 1H), 0.60 (q, J=7.9 Hz, 2H), 0.26 (q, J=5.3 Hz, 2H).

Step G: To a methanol (5 mL) solution of the oxadiazole from step F (0.027 g, 0.05 mmol) was added TFA (1.5 mL) followed by a catalytic amount of Pd(OH)$_2$. The solution was the placed under a H$_2$ atmosphere via a balloon for 20 min. The solution was filtered through celite and concentrated in vacuo to afford the fully deprotected amino pyridine.

LCMS [M+H]=457.1

$^1$H NMR (CD$_3$OD) δ 7.31-7.21 (m, 3H), 7.21 (s, 1H). 7.08 (m, 2H), 6.69 (s, 1H), 3.46 (d, J=4.8 Hz, 2H), 3.36 (s, 3H), 3.17 (s, 3H), 3.08 (d, J=7.0 Hz, 2H), 1.87 (s, 3H), 1.14-1.08 (m, 1H), 0.59 (d, J=7.0 Hz, 2H), 0.30 (d, J=5.1 Hz, 2H).

EXAMPLE 92

N-(4-{5-[(1R)-1-amino-1-methyl-2-phenylethyl]-1H-pyrazol-3-yl}-6-{benzyl[(2-methylcyclopropyl)methyl]amino}pyridin-2-yl)-N-methylpropane-2-sulfonamide

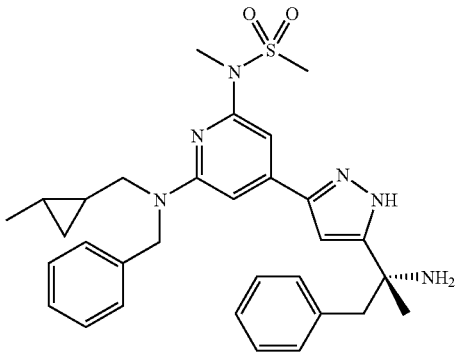

To a solution of Intermediate n (62 mg, 0.09 mmol) in 0.5 mL DMF was added anhydrous hydrazine (14 µL, 0.46 mmol). The resulting mixture was heated at 90° C. for 18 h and then cooled to rt. To this was added 2 mL water and 3 mL ethyl acetate. The organic layer was isolated, washed with brine, dried over sodium sulfate, and concentrated to dryness. Purification by reverse-phase chromatography yielded tert-butyl (1R)-1-(3-{2-{benzyl[(2-methylcyclopropyl)methyl]amino}-6-[(isopropylsulfonyl)(methyl)amino]pyridin-4-yl}-1H-pyrazol-5-yl)-1-methyl-2-phenylethylcarbamate, which was dissolved in 1 mL 20% TFA in dichloromethane. After 1 hour, the solution was concentrated to afford titled example, N-(4-{5-[(1R)-1-amino-1-methyl-2-phenylethyl]-1H-pyrazol-3-yl}-6-{benzyl[(2-methylcyclopropyl)methyl]amino}pyridin-2-yl)-N-methylpropane-2-sulfonamide. $^1$H NMR (400 MHz, d$_4$-MeOH) δ 7.31-7.19 (m, 9H), 7.01-6.99 (m, 2H), 6.76 (s, 1H), 6.71 (s, 1H), 6.61 (s, 1H), 4.96-4.76 (m, 2H), 3.81-3.74 (m, 1H), 3.69-3.63 (m, 1H) 3.39 (s, 3H), 3.35-3.22 (m, 4H), 1.70 (s, 3H), 1.14 (d, J=6.8 Hz, 6H), 0.94 (d, J=6 Hz, 3H), 0.87-0.84 (m, 1H), 0.66-0.60 (m, 1H), 0.42-0.38 (m, 1H), 0.26-0.21 (m, 1H); LCMS [M+H]=587.2.

Use of the preferred enantiomer trans-S,S from Intermediate A, step B, affords the preparation of the preferred enantiopure S,S,R example.

EXAMPLE 93

N-(4-{6-[(1R)-1-amino-1-methyl-2-phenylethyl]pyrimidin-4-yl}-6-{benzyl[(2-methylcyclopropyl)methyl]amino}pyridin-2-yl)-N-methylpropane-2-sulfonamide

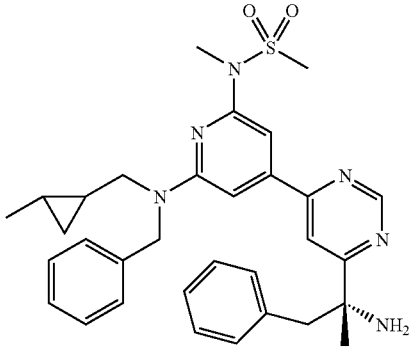

Step A: Condensation

A suspension of 69 mg (1.01 mmol) sodium ethoxide in 1 mL DMA was added dropwise to a solution of 81 mg (1.01 mmol) formamidine hydrochloride in 1 mL DMA and the mixture was stirred vigorously for 5 min. A solution of Intermediate n (68 mg, 0.10 mmol) in 1 mL DMA was added dropwise to the first mixture, and the resulting mixture was heated to 110° C. 30 min. and then allowed to cool to rt. Water (10 mL) was added and the mixture extracted with ethyl acetate (3×15 mL). The combined organics were washed with 3M aq. LiCl (3×25 mL), washed with brine (25 mL), dried over sodium sulfate, and concentrated. Purification by reverse phase chromatography afforded tert-butyl (1R)-1-(6-{2-{benzyl[(2-methylcyclopropyl)methyl]amino}-6-[(isopropylsulfonyl)(methyl)amino]pyridin-4-yl}-3,4-dihydropyrimidin-4-yl)-1-methyl-2-phenylethylcarbamate as a yellow oil. LCMS [M+H]=701.3

Step B: Oxidation and Deprotection

To a solution of tert-butyl (1R)-1-(6-{2-{benzyl[(2-methylcyclopropyl)methyl]amino}-6-[(isopropylsulfonyl)(methyl)amino]pyridin-4-yl}-3,4-dihydropyrimidin-4-yl)-1-methyl-2-phenylethylcarbamate from Step A above (49 mg, 0.07 mmol) in 2 mL toluene was added dichlorodicyanoquinone (24 mg, 0.11 mmol). The resulting solution was heated at 120 degrees for 30 min., then cooled to it and concentrated to dryness. Purification by reverse phase chromatography yielded tert-butyl (1R)-1-(6-{2-{benzyl[(2-methylcyclopropyl)methyl]amino}-6-[(isopropylsulfonyl)(methyl)amino]pyridin-4-yl}pyrimidin-4-yl)-1-methyl-2-phenylethylcarbamate, which was taken up in 1 mL 20% TFA in dichloromethane. The mixture was allowed to sit for 1 hour, and was concentrated to afford the title compound N-(4-{6-[(1R)-1-amino-1-methyl-2-phenylethyl]pyrimidin-4-yl}-6-{benzyl[(2-methylcyclopropyl)methyl]amino}pyridin-2-yl)-N-methylpropane-2-sulfonamide. $^1$H NMR (400 MHz, d$_4$-MeOH) δ 9.29 (s, 1H), 7.66-7.65 (m, 1H), 7.31-7.21 (m, 8H), 7.02-7.01 (m, 2H), 6.96-6.93 (m, 2H), 4.98-4.60 (m, 2H), 3.83-3.66 (m, 2H), 3.38 (s, 3H), 3.35-3.25 (m, 4H), 1.81 (s, 3H), 1.16 (d, J=6.8 Hz), 0.96 (dd, J=6 Hz, J=1.8 Hz, 3H) 0.90-0.82 (m, 1H), 0.70-0.62 (m, 1H), 0.45-0.40 (m, 1H), 0.28-0.24 (m, 1H); LCMS [M+H]=599.1.

Use of the preferred enantiomer trans-S,S from Intermediate A, step B, affords the preparation of the preferred enantiopure S,S,R example.

EXAMPLE 94

N-{2-{5-[(1R)-1-amino-1-methyl-2-phenylethyl]-1,3,4-oxadiazol-2-yl}-6-[(cyclopropylmethyl)(methyl)amino]pyridin-4-yl}-N-methylmethanesulfonamide

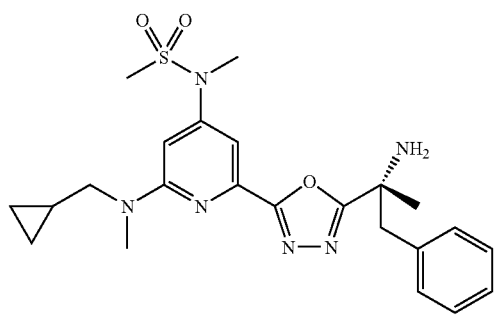

Step A: A solution containing 6.52 g (40.0 mmol) of 4-amino-2,6-dichloropyridine in 200 mL of pyridine was treated with 22.8 g (200 mmol) methanesulfonyl chloride and heated at 60° C. over 72 h. The reaction mixture was cooled and the solvent was evaporated. The resulting residue was redissolved in 200 mL of dichloromethane and washed with NaHCO$_3$ (50 mL), water (3×50 mL) and brine (50 mL). The organic phase was dried over MgSO$_4$, filtered, and concentrated. Purification by silica gel chromatography (20% EtOAc/hexanes) afforded the desired sulfonamide (5.30 g, 55%) along with 3.44 g (27%) of the unwanted bis sulfonamide.

LCMS [M+H]=241.1

Step B: A solution containing 5.00 g (20.7 mmol) of the sulfonamide from step A in 12.5 g (176 mmol) of cyclopropylamine was heated at 125° C. in a sealed tube. After 72 h the reaction mixture was cooled and evaporated to leave a brown residue that was purified by silica gel chromatography (60% EtOAc/hexanes) to give the desired aminopyridine (3.42 g, 60%).

LCMS [M+H]=276.1

Step C: To a 0° C. solution containing 1.00 g (3.62 mmol) of the aminopyridine from step B and 1.13 g (7.98 mmol) of methyl iodide in 15 mL of DMF was added 191 mg (7.98 mmol) of sodium hydride. The solution was stirred to rt over 17 h and quenched with 5 mL of water. The reaction mixture was diluted with 100 mL of ether and washed with water (6×10 mL) then brine (10 mL). The organic phase was dried over MgSO$_4$, filtered, and concentrated. Purification by silica gel chromatography (30% EtOAc/Hex) afforded the methylated aminopyridine (1.00 g, 91%).

LCMS [M+H]=304.1

Step D: To a solution containing 1.00 g (3.29 mmol) of the chloropyridine from step C in 15 mL of DMF was added zinc cyanide (773 mg, 6.58 mmol) followed by Pd(PPh$_3$)$_4$ (761 mg, 0.658 mmol). The solution was heated to 90° C. for 24 h before the reaction mixture was cooled and diluted with ether (100 mL) then washed with H$_2$O (6×10 mL). The organic phase was dried over MgSO$_4$, filtered, and concentrated. Purification by silica gel chromatography (30% EtOAc/Hex) afforded the desired cyanopyridine (2.66 g, 81%).

LCMS [M+H]=295.2

Step E: To a solution of the cyanopyridine from step D (150 mg, 0.51 mmol) in 9:1 EtOH/H$_2$O (10 mL) was added solid KOH (286 mg, 5.1 mmol). The solution was heated to 85° C. for 16 h. The reaction mixture was cooled, acidified with 3N HCl, and extracted with EtOAc (3×30 mL). The combined organics layers were washed with brine (1×50 mL), dried over MgSO$_4$, filtered and concentrated. The residue was used without further purification. To a solution of the carboxylic acid in DCM (5 mL) was added hydrazide intermediate I (140 mg, 0.48 mmol), DIPEA (186 mg, 1.43 mmol) and BOP reagent (212 mg, 0.48 mmol). The reaction was stirred at rt for 1 h and loaded directly onto a silica column (50% EtOAc/hexanes) to afford the desired hydrazide (150 mg, 53%)

LCMS [M+H]=589.1

Step F: To a 1,2-dichloroethane solution (3 mL) of the hydrazide from step E (150 mg, 0.255 mmol) was added Burgess reagent (182 mg, 0.764 mmol). The solution was microwaved at 140° C. for 8 min. Purification by silica gel chromatography afforded the desired oxadiazole (90 mg, 62%).

LCMS [M+H]=571.1

$^1$H NMR (CDCl$_3$) δ 7.29-7.19 (m, 5H), 7.05 (m, 2H), 6.79 (s, 1H), 5.23 (bs, 1H), 3.54-3.41 (m, 4H), 3.38 (s, 3H), 3.17 (s, 3H), 2.92 (s, 3H), 1.76 (m, 3H), 1.41 (br s, 9H), 1.24-1.13 (m, 1H), 0.50 (m, 2H), 0.26 (m, 2H).

Step G: To a DCM (5 mL) solution of the oxadiazole from step F (50 mg, 0.083 mmol) was added TFA (1.5 mL). The solution was stirred for 30 min and concentrated. Trituration with ether afforded 50 mg (100%) of the desired compound as its TFA salt.

LCMS [M+H]=471.1

$^1$H NMR (CD$_3$OD) δ 7.41 (s, 1H), 7.37-7.25 (m, 3H), 7.05 (m, 2H), 6.75 (s, 1H), 3.54-3.41 (m, 4H), 3.38 (s, 3H), 3.17 (s, 3H), 2.94 (s, 3H), 1.86 (m, 3H), 1.24-1.13 (m, 1H), 0.50 (m, 2H), 0.26 (m, 2H).

The following abbreviations are used throughout the text:

Me: methyl

Bu: butyl i-Bu: isobutyl t-Bu: tert butyl

Et: ethyl

Pr: propyl i-Pr: isopropyl

Ar: aryl

Ph: phenyl

Py: pryridine

Ac: acetyl

EDC: ethyl-3-(3-dimethylaminopropyl)-carbodiimide

HOAt: 1-hydroxy-7-azabenzotriazole

HOBt: 1-hydroxybenzotriazole

DMF: N,N'-dimethyl formamide

THF: tetrahydrofuran

DMSO: dimethylsulfoxide

EDTA: ethylene diamine tetraacetic acid

Boc: tert-butyloxy carbonyl

BOP: Benzotriazol-1-yloxy-tris(dimethylamino)phosphonium hexafluorophosphate

CHAPS: 3-[(3-cholamidopropyl)dimethylammonio]-2-hydroxy-1-propanesulfonate

TEA: triethylamine

TFA: trifluoroacetic acid

NaHMDS: sodium hexamethyldisilazide

NCS: N-chloro succinimide

DCE: dichloroethane

DIPEA: diisopropylethylamine

DCM: dichloromethane

DIC: N,N'-diisopropylcarbodiimide

DCA: 1,2-dichloroethene

DMA: N,N-dimethylacetamide aq: aqueous rt: room temperature

HPLC: high performance liquid chromatography

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

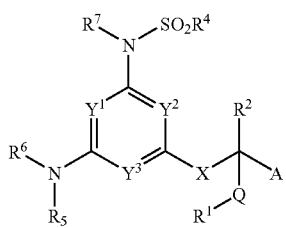

wherein:

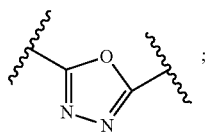

X is
$Y^1$ is N and $Y^2$ and $Y^3$ are each CH;
A is selected from the group consisting of
  (1) hydrogen,
  (2) —$C_{1-10}$ alkyl, and
  (3) —$C_{2-10}$ alkenyl,
  wherein said alkyl or alkenyl is unsubstituted or substituted with one or more
    (a) halo,
    (b) —$C_{3-12}$ cycloalkyl,
    (c) —OH,
    (d) —CN,
    (e) —O—$C_{1-10}$ alkyl,
    (f) phenyl, or
    and said phenyl is unsubstituted or substituted with one or more
      (i) halo,
      (ii) —OH,
      (iii) —CN,
      (iv) —O—$C_{1-10}$ alkyl,
      (v) —$C_{1-10}$ alkyl, or
      (vi) —$C_{3-12}$ cycloalkyl;
Q is —$C_{0-3}$ alkyl, wherein said alkyl is unsubstituted or substituted with one or more
  (1) halo,
  (2) —$C_{3-12}$ cycloalkyl,
  (3) —OH,
  (4) —CN,
  (5) —O—$C_{1-10}$ alkyl, and
  (6) —$C_{1-10}$ alkyl;
$R^1$ is (1) aryl selected from the group consisting of phenyl and napthyl,
  (3) —$C_{1-10}$ alkyl, and
  (4) $C_{3-8}$ cycloalkyl, said cycloalkyl optionally fused to a $C_{6-10}$ aryl group,
  wherein said alkyl, cycloalkyl, or aryl is unsubstituted or substituted with one or more
    (a) halo,
    (b) —$C_{1-10}$ alkyl, wherein said alkyl is unsubstituted or substituted with halogen,
    (c) —OH,
    (d) —CN,
    (e) —O—$C_{1-10}$ alkyl,
    (f) —$C_{3-12}$ cycloalkyl, or
    (g) —$NR^8R^9$;
$R^2$ is selected from the group consisting of
  (1) —OH, and
  (2) —$NR^8R^9$, wherein $R^8$ and $R^9$ are selected from the group consisting of
    (a) hydrogen,
    (b) $C_{1-10}$ alkyl, and
    (c) $C_{0-6}$ alkyl-$C_{6-10}$ aryl,
$R^4$ is selected from the group consisting of
  (1)—$C_{1-10}$ alkyl, or
  (2) —$C_{3-12}$ cycloalkyl,
  wherein said alkyl and cycloalkyl is unsubstituted or substituted with one or more
    (a) halo,
    (b) —OH,
    (c) —CN,
    (d) —O—$C_{1-10\ alkyl}$,
    (e) —$C_{1-10}$ alkyl,
    (f) —$C_{3-12}$ cycloalkyl,
    (g) aryl selected from the group consisting of phenyl and napthyl, or
    and said aryl is unsubstituted or substituted with one or more
      (i) halo,
      (ii) —OH,
      (iii) —CN,
      (iv) —O—$C_{1-10}$ alkyl,
      (v) —$C_{3-12}$ cycloalkyl, or
      (vi) —$C_{1-10}$ alkyl;
$R^7$ is selected from the group consisting of
  (1) hydrogen,
  (2) —$C_{1-10}$ alkyl,
  (3) aryl selected from the group consisting of phenyl and naphthyl;
  wherein said alkyl or aryl is unsubstituted or substituted with one or more
    (a) halo,
    (b) —OH,
    (c) —CN,
    (d) —O—$C_{1-10}$ alkyl,
    (e) —$C_{3-12}$ cycloalkyl,
    (f) aryl selected from the group consisting of phenyl and napthyl, or
    wherein said cycloalkyl, or aryl is unsubstituted or substituted with one or more
      (i) halo,
      (ii) —OH,
      (iii) —CN,
      (iv) —O—$C_{1-10}$ alkyl,
      (v) —$C_{3-12}$ cycloalkyl, or
      (vi) aryl selected from the group consisting of phenyl and napthyl;

$R^5$ and $R^6$ are independently selected from the group consisting of
(1) hydrogen,
(2) —$C_{1-10}$ alkyl,
(3) —$C_{2-10}$ alkenyl,
(4) —$C_{2-10}$ alkynyl, and
(5) —$C_{1-10}$ alkyl-$C_{3-12}$ cycloalkyl,
wherein said alkyl, cycloalkyl, alkenyl or alkynyl is unsubstituted or substituted with one or more
(a) halo,
(b) —OH,
(c) —CN,
(d) —$C_{1-10}$ alkyl
(e) —$C_{3-12}$ cycloalkyl,
(f) —O—$C_{1-10}$ alkyl,
(h) phenyl, or
(i) —$NR^8R^9$;
and n is 0, 1, 2, 3 or 4;
or a pharmaceutically acceptable salt thereof, or an individual enantiomer or diastereomer of said compound or said salt.

2. The compound of claim 1 wherein $R^1$ is phenyl and Q is $CH_2$.

3. The compound of claim 1 wherein $R^2$ is —$NR^8R^9$.

4. The compound of claim 1 wherein A is $C_{1-6}$ alkyl.

5. The compound of claim 1 wherein $R^4$ and $R^7$ are $C_{1-10}$ alkyl.

6. The compound of claim 1 which is a compound of formula (II)

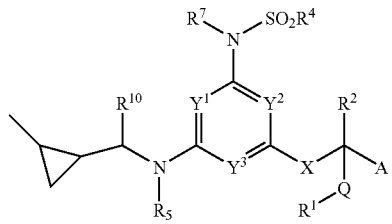

(II)

wherein A, X, $Y^1$, $Y^2$, $Y^3$, Q, $R^1$, $R^2$, $R^4$, $R^5$, and $R^7$, are as defined in claim 1, and $R^{10}$ is selected from the group consisting of H and $C_1$-$C_6$ alkyl, or a pharmaceutically acceptable salt thereof, or an individual enantiomer or diastereomer of said compound or said salt.

7. The compound of claim 6, wherein $R^1$ is phenyl and Q is $CH_2$.

8. The compound of claim 6, wherein $R^2$ is $NR^8R^9$.

9. The compound of claim 6, wherein $R^5$ is hydrogen or $C_{1-10}$ alkyl, wherein said $C_{1-10}$ alkyl is substituted or unsubstituted with one or more:
(1) halo,
(2) —OH,
(3) —CN,
(4) phenyl,
(5) —$OC_{1-10}$ alkyl, or
(6) —$NR^8R^9$.

10. The compound of claim 9, wherein $R^5$ is $C_{1-10}$ alkyl, wherein said $C_{1-10}$ alkyl is substituted or unsubstituted with one or more halo.

11. The compound of claim 1 which is selected from the group consisting of

1

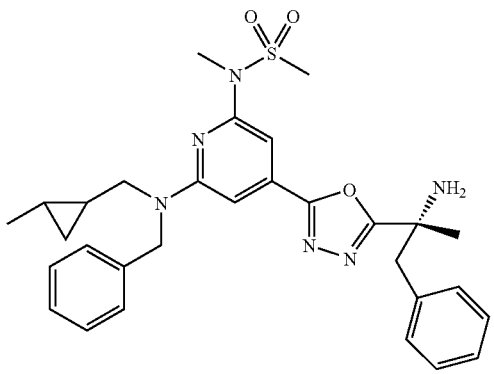

2

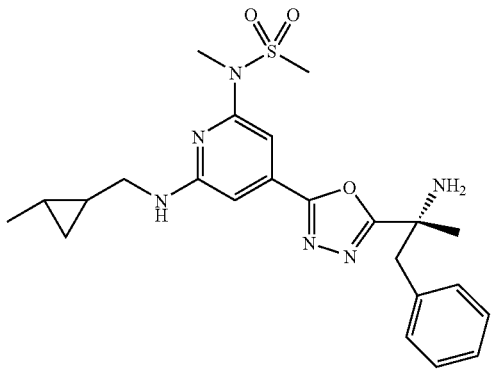

3 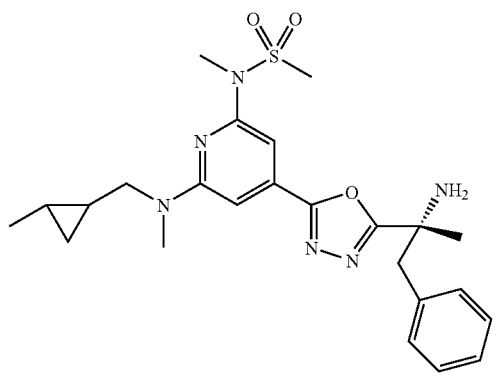
4 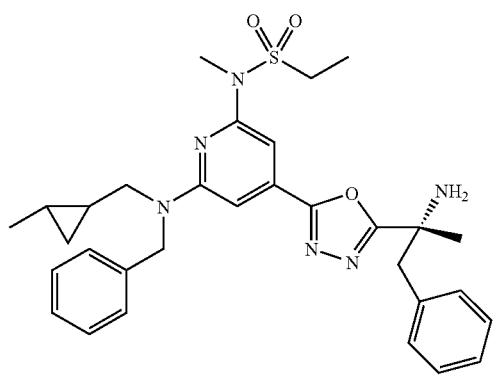
5 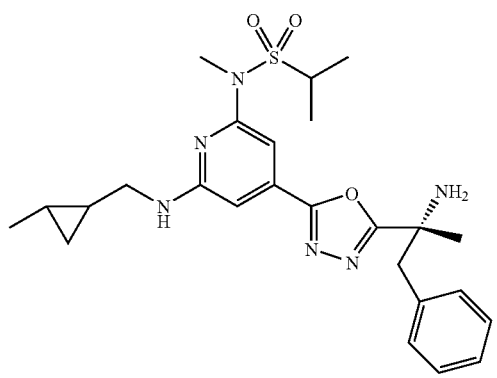
6 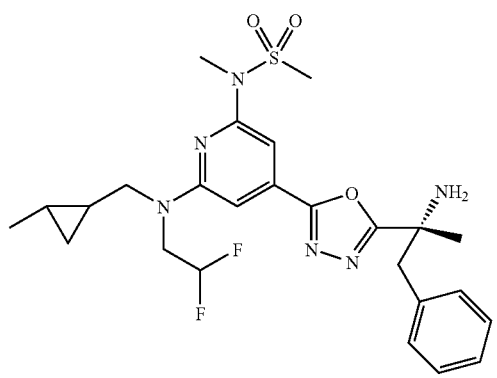

7 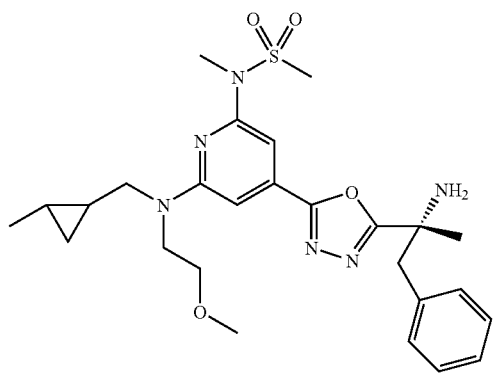
8 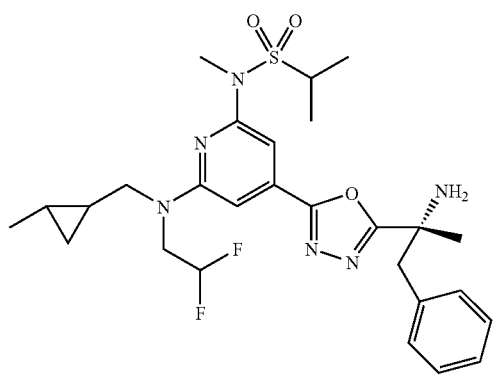
9 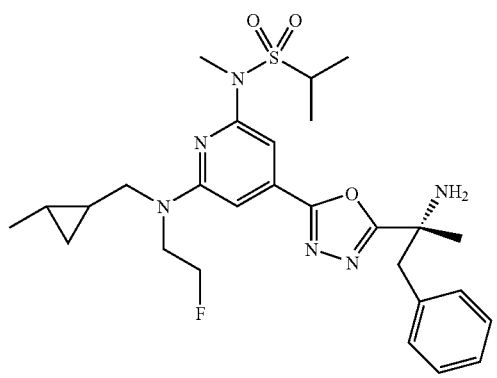
10 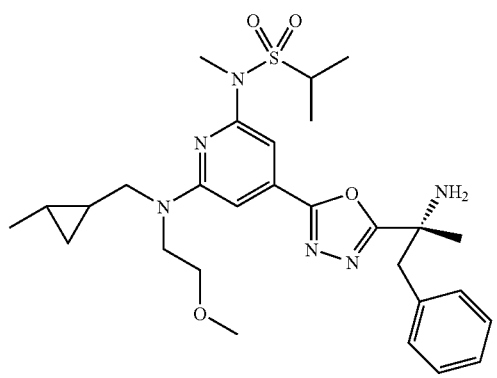

11 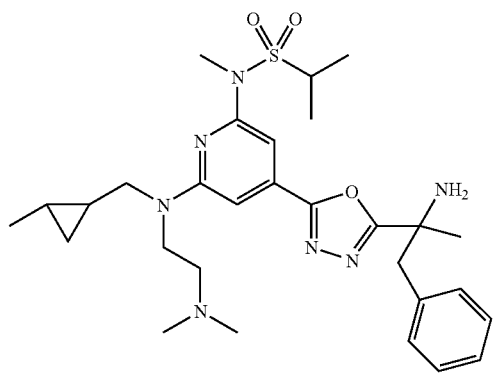
12 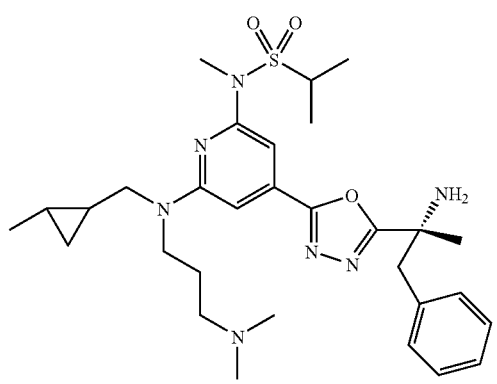
13 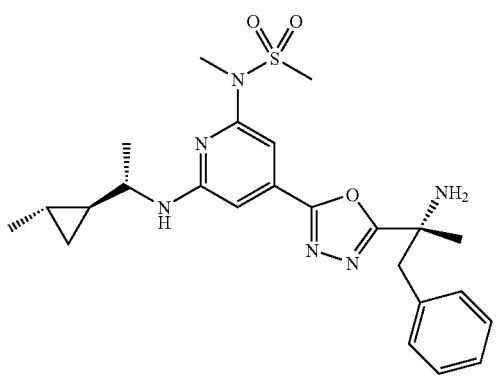
14 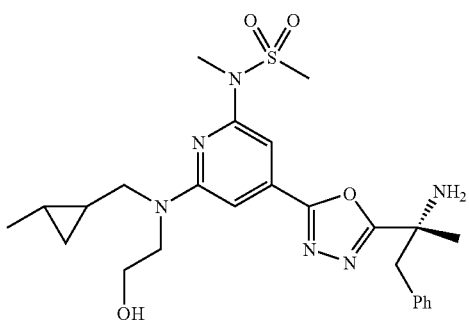

-continued
| | |
|---|---|
| 15 | 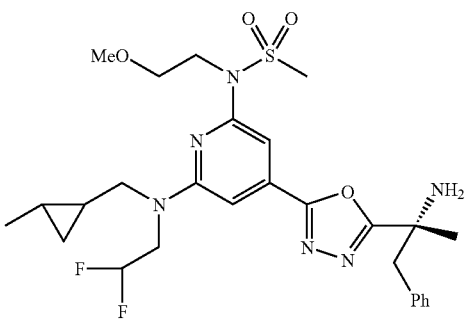 |
| 16 | 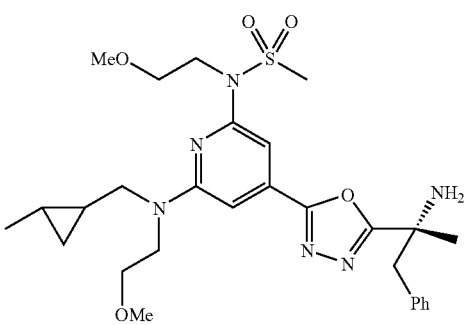 |
| 17 | 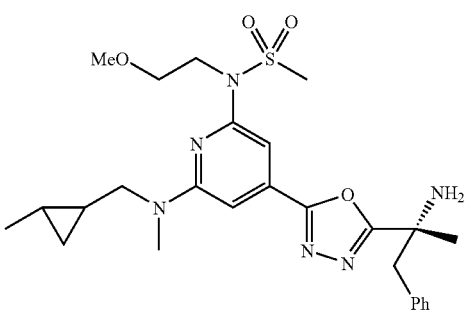 |
| 18 | 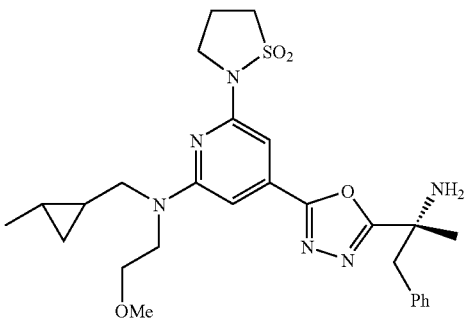 |
| 19 | 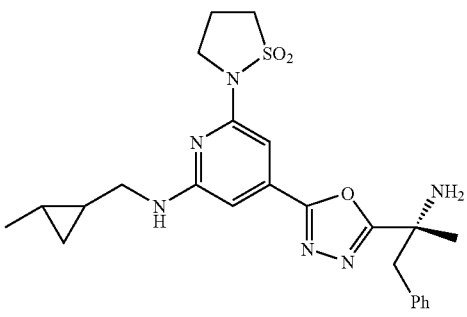 |

27 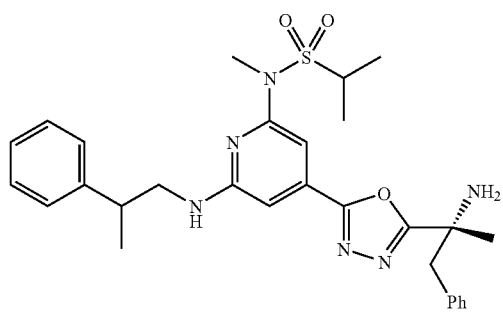
28 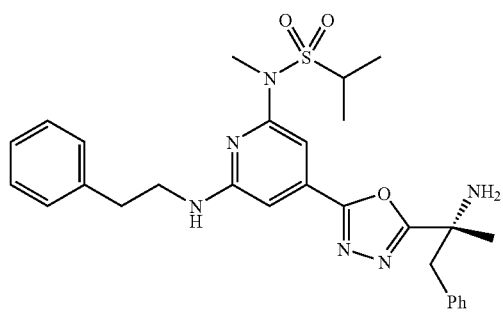
31 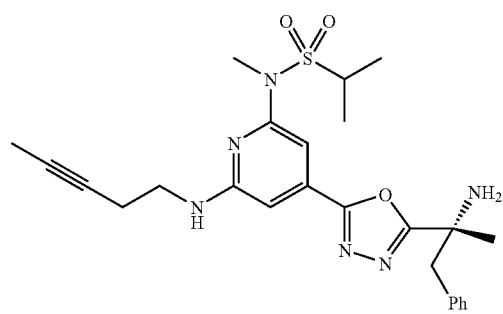
32 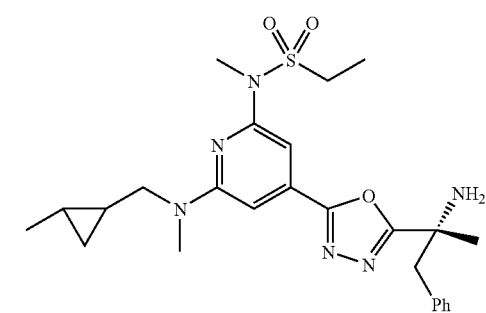
33 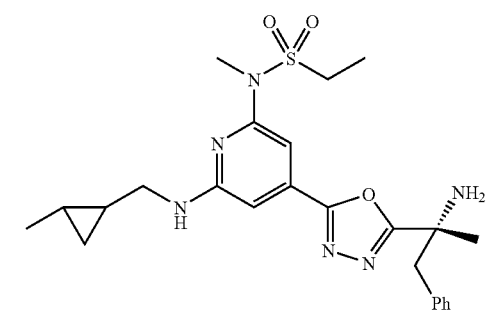

| | |
|---|---|
| 34 | 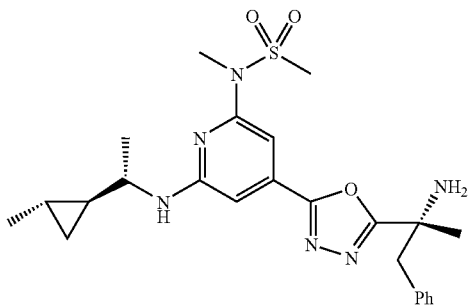 |
| 35 | 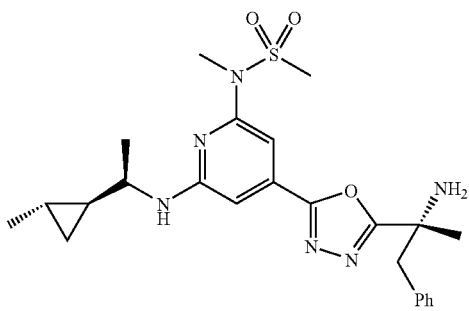 |
| 36 | 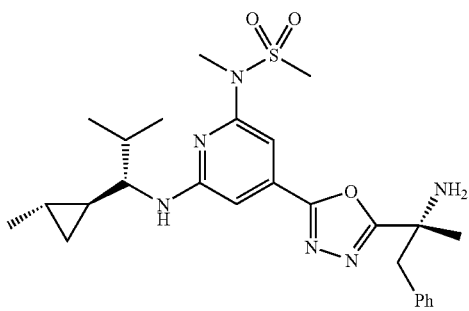 |
| 37 | 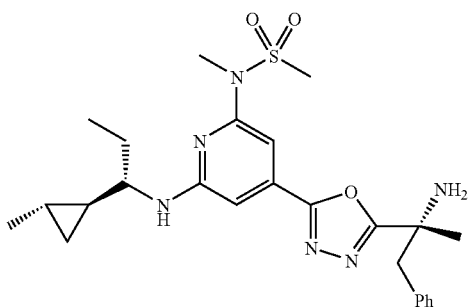 |
| 38 | 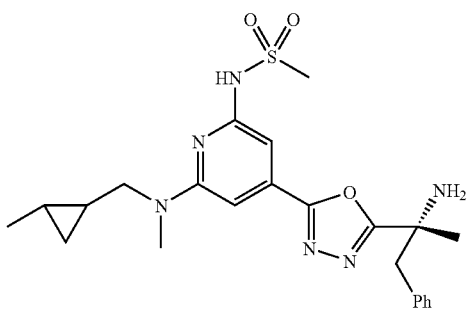 |

51 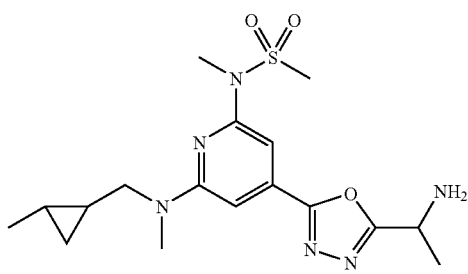
53 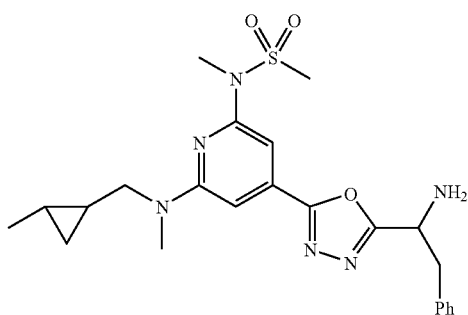
54 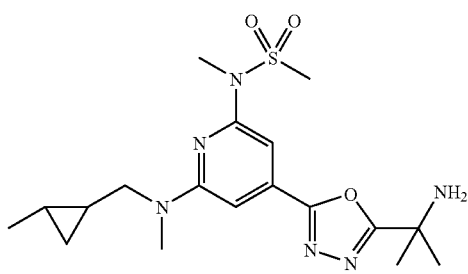
55 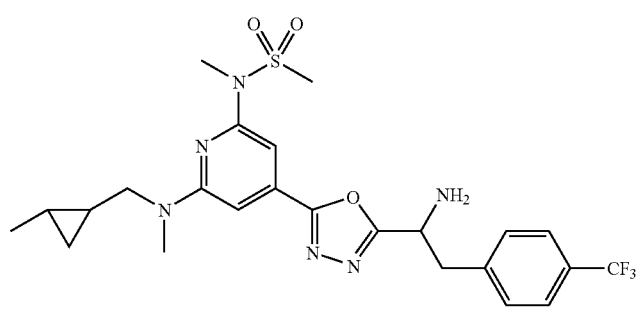
56 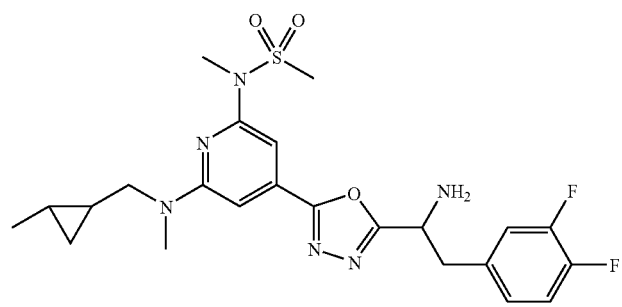

-continued
57
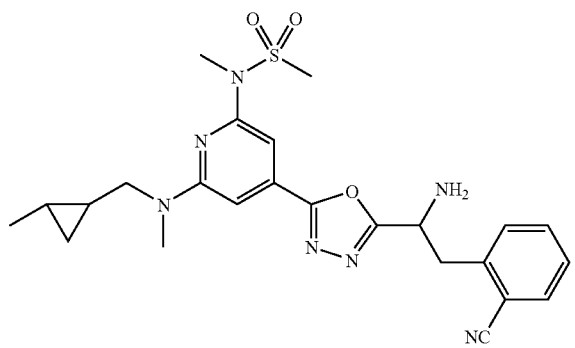
58
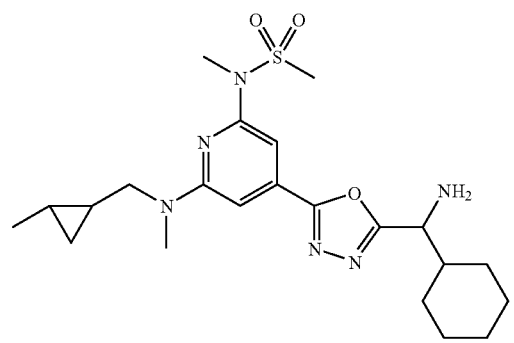
59
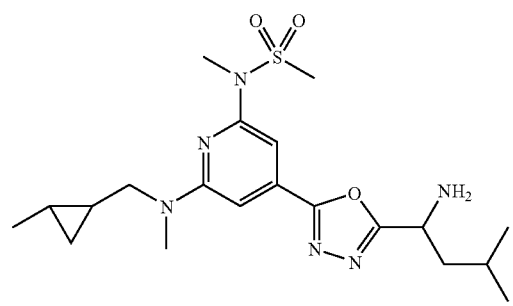
60
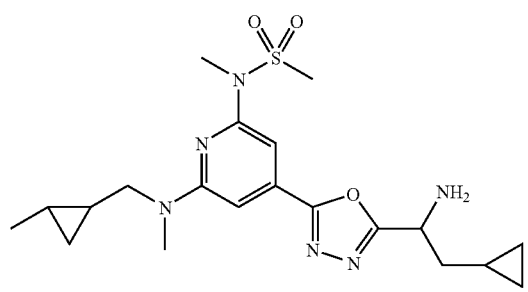
61
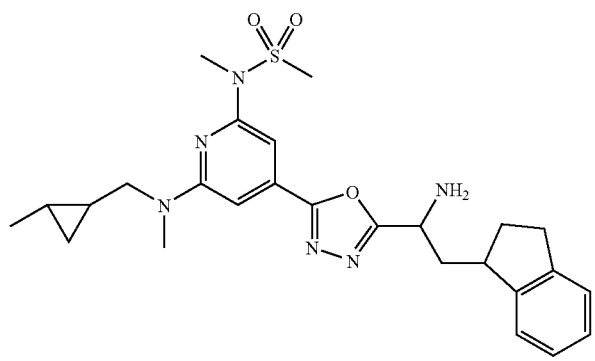

63 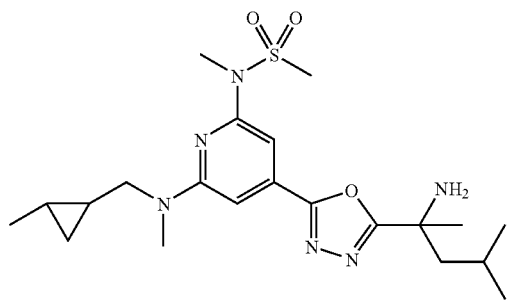
64 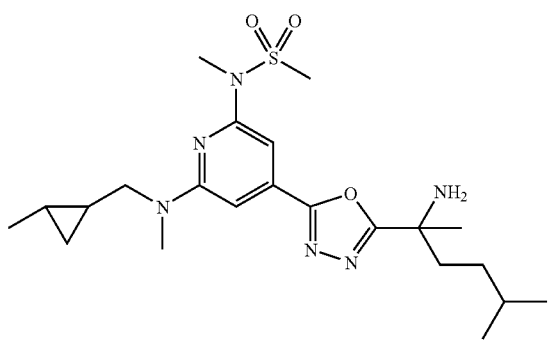
66 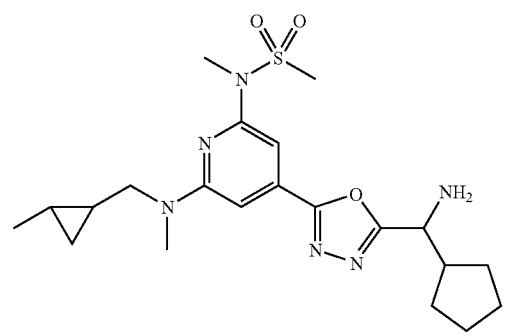
67 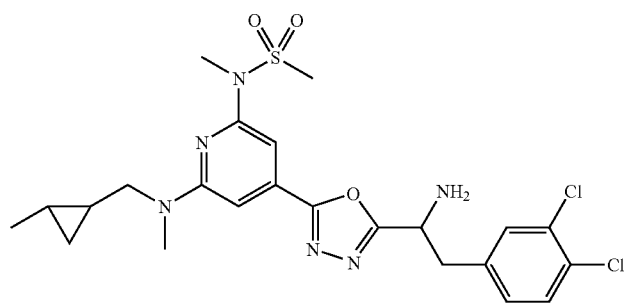

68 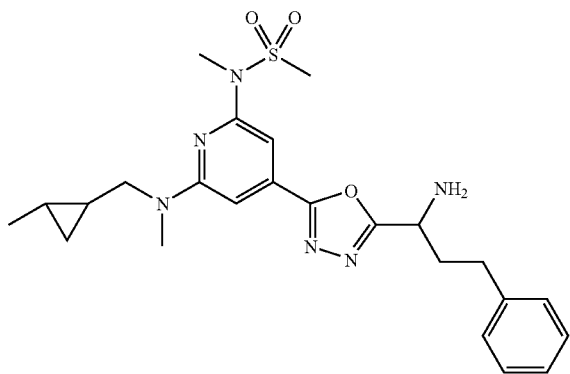
71 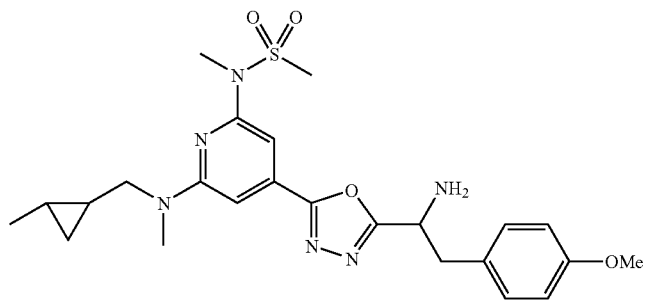
74 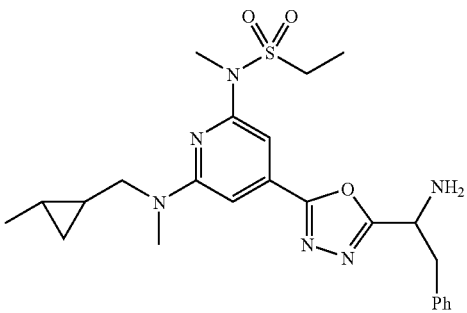
78 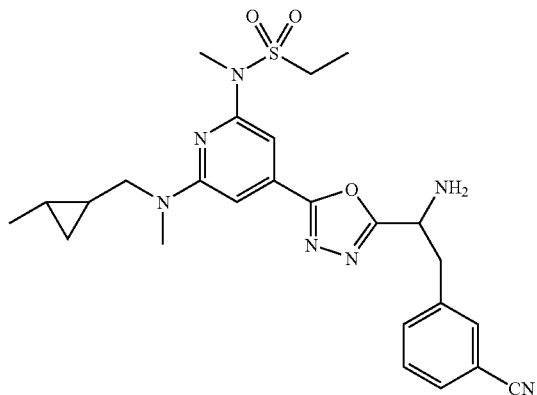

79 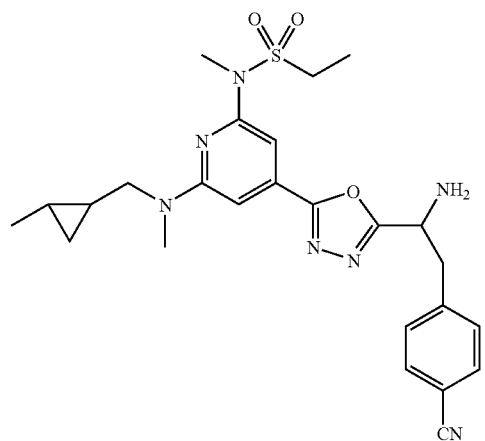
80 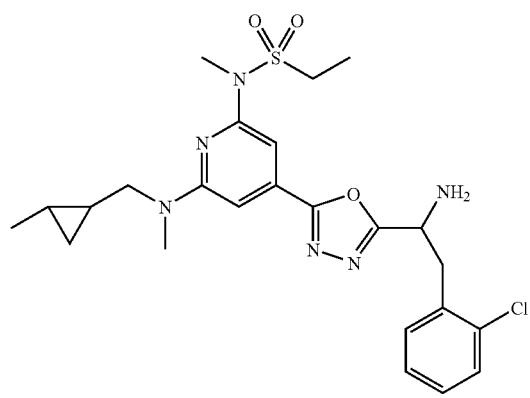
81 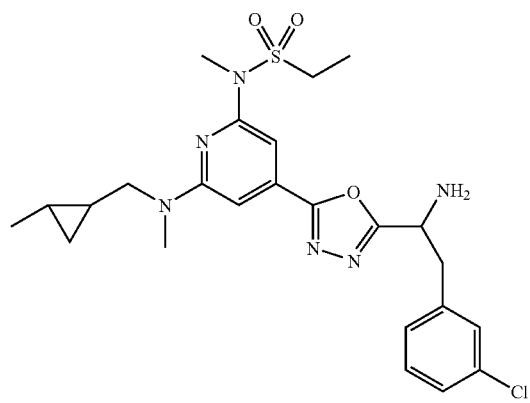

82
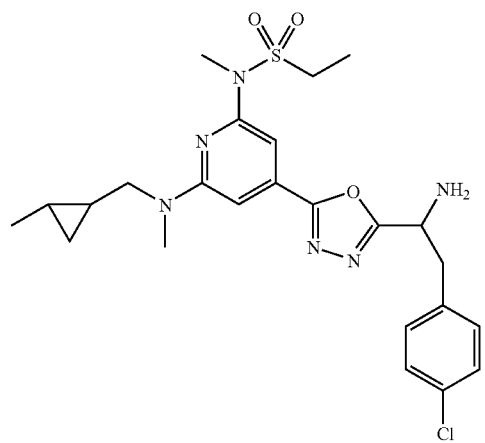
83
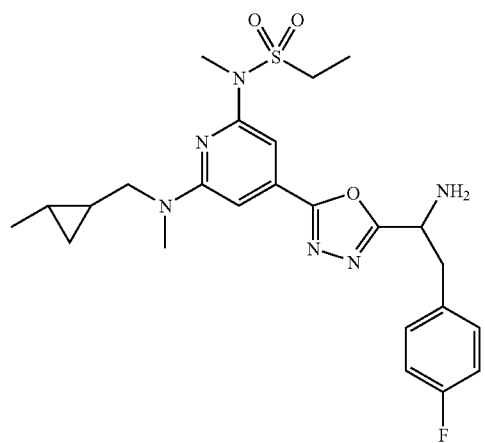
85
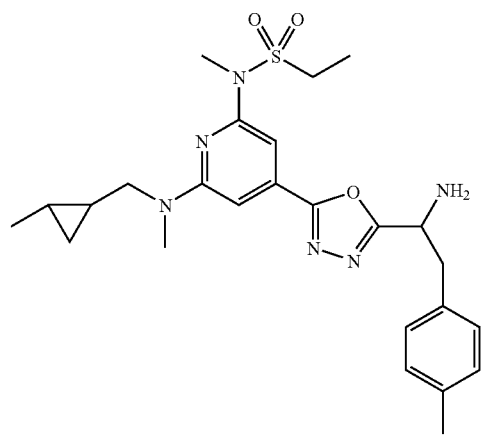

87 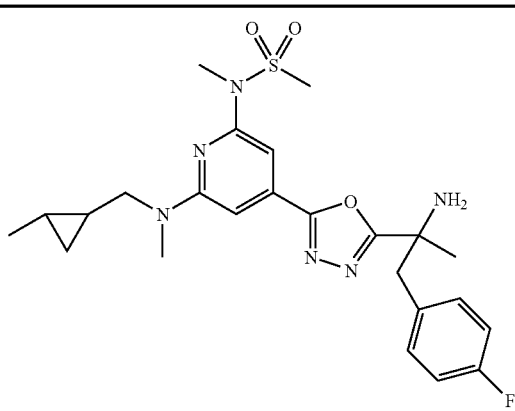
90 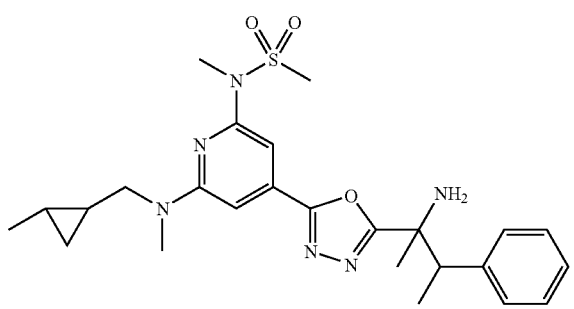
and pharmaceutically acceptable salts thereof.
12. The pharmaceutical composition comprising a therapeutically effective amount of a compound of claim 1 or a pharmaceutically acceptable salt thereof and a pharmaceutically acceptable carrier.
* * * * *